United States Patent
Karas et al.

(10) Patent No.: US 10,137,141 B2
(45) Date of Patent: Nov. 27, 2018

(54) TREATMENT REGIMEN TIACUMICIN COMPOUND

(71) Applicant: Astellas Pharma Europe Ltd., Chertsey, Surrey (GB)

(72) Inventors: Andreas Johannis Karas, Surrey (GB); Christopher Mark Longshaw, Surrey (GB)

(73) Assignee: Astellas Pharma Europe Ltd., Chertsey, Surrey (GB)

( * ) Notice: Subject to any disclaimer, the term of this patent is extended or adjusted under 35 U.S.C. 154(b) by 0 days.

(21) Appl. No.: 15/309,992

(22) PCT Filed: May 11, 2015

(86) PCT No.: PCT/EP2015/000965
§ 371 (c)(1),
(2) Date: Nov. 9, 2016

(87) PCT Pub. No.: WO2015/169451
PCT Pub. Date: Nov. 12, 2015

(65) Prior Publication Data
US 2017/0143750 A1 May 25, 2017

(30) Foreign Application Priority Data

May 9, 2014 (EP) .................... 14075031

(51) Int. Cl.
*A61K 31/7048* (2006.01)
*A61K 9/28* (2006.01)

(52) U.S. Cl.
CPC ............ *A61K 31/7048* (2013.01); *A61K 9/28* (2013.01)

(58) Field of Classification Search
CPC .............................. A61K 31/7048; A61K 9/28
See application file for complete search history.

(56) References Cited

U.S. PATENT DOCUMENTS

| | | | |
|---|---|---|---|
| 4,918,174 A | 4/1990 | McAlpine et al. | |
| 5,583,115 A | 12/1996 | McAlpine et al. | |
| 5,767,096 A | 6/1998 | Hochlowski et al. | |
| 2008/0176927 A1* | 7/2008 | Sanghvi ............... | A61K 9/2013 514/450 |

FOREIGN PATENT DOCUMENTS

| | | |
|---|---|---|
| CN | 102030791 A | 4/2011 |
| CN | 102219815 A | 10/2011 |
| WO | 2004/014295 A2 | 2/2004 |
| WO | 2005/112990 A2 | 12/2005 |
| WO | 2006/085838 A1 | 8/2006 |
| WO | 2008/091554 A1 | 7/2008 |
| WO | 2013/138748 A1 | 9/2013 |
| WO | 2014/111254 A1 | 7/2014 |

OTHER PUBLICATIONS

Chilton et al. Conference Paper, Sep. 2013, "Comparison of Extended Duration fidaxomicin dosing regimens for treatment of Clostridium difficile infection (CDI) in an in vitro gut model," retrieved from the internet on Nov. 26, 2017, pp. 1-2.*
Soriano et al.,Abstract and Poster, "The Use of a Fidaxomicin Taper/Pulsed Chaser as Effective Salvage Therapy for Vancomycin-Refractory, Recurrent Clostridium difficile Infections," retrieved from the internet on Nov. 25, 2017, pp. 1-2.*
Baines et al., "Effects of piperacillin/tazobactam on Clostridium difficile growth and toxin production in a human gut model," Journal of Antimicrobial Chemotherapy, 55: 974-982 (2005).
Chilton et al., "Efficacy of alternative fidaxomicin dosing regimens for treatment of simulated Clostridium difficile infection in an in vitro human gut model," Journal of Antimicrobial Chemotherapy, 70: 2598-2607 (2015).
Chilton et al., "Efficacy of tapered fidaxomicin dosing regimens to treat simulated Clostridium difficile infection (CDI) in an in vitro gut model," Conference Paper, http://www.researchgate.net/profile/Chris_Longshaw/publication/262292381_Efficacy_of_tapered_fidaxomicin_dosing_regimens_to_treat_simulated_Clostridium_difficile_infection_(CDI)_in_an_in_vitro_gut_model/links/02e7e53737f70bb807000000.pdf?origin=publication_detail (2014).
Chilton et al., "Successful treatment of simulated clostridium difficile infection in a human gut model by fidaxomicin first line and after vancomycin or metronidazole failure," Journal of Antimicrobial Chemotherapy, 69: 451-462 (2014), Advanced Access publication on Sep. 3, 2013.
Freeman et al., "Effects of cefotaxime and desacetylcefotaxime upon Clostridium difficile proliferation and toxin production in a triple-stage chemostat model of the human gut," Journal of Antimicrobial Chemotherapy, 52: 96-102 (2003).
Golan et al., "Safety and efficacy of fidaxomicin in the treatment of Clostridium difficile-associated diarrhea," Therapeutic Advances in Gastroenterology, 5: 395-402 (2012).
Johnson et al., "Fidaxomicin "Chaser" Regimen Following Vancomycin for Patients With Multiple Clostridium difficile Recurrences," Clinical Infectious Diseases, 56: 309-310 (2013).

(Continued)

*Primary Examiner* — Aradhana Sasan
(74) *Attorney, Agent, or Firm* — Morgan, Lewis & Bockius LLP

(57) ABSTRACT

A tiacumicin compound, a stereo-isomer thereof, a polymorph thereof or a pharmaceutically acceptable solvate thereof, and a pharmaceutical composition, containing a tiacumicin compound, a stereo-isomer thereof, a polymorph thereof or a pharmaceutically acceptable solvate thereof, are provided for use in the oral treatment of *Clostridium difficile* infections (CDI) or *Clostridium difficile* associated diarrhea or disease (CDAD) in a patient in accordance with a dosage regimen selected from the group consisting of:

i. Administering 200 mg of the tiacumicin compound BID for 5 days followed by 5 days of rest and then 200 mg once daily for a further 10 days and ii. Administering 200 mg of the tiacumicin compound BID for 5 days followed by a single 200 mg every other day for 20 days.

21 Claims, 50 Drawing Sheets

(56) References Cited

OTHER PUBLICATIONS

Louie et al., "Fidaxomicin Preserves the Intestinal Microbiome During and After Treatment of Clostridium difficile Infection (CDI) and Reduces Both Toxin Reexpression and Recurrence of CDI," Clinical Infectious Diseases, 55: S132-S142 (2012).
McFarland, "Epidemiology, Risk Factors and Treatments for Antibiotic-Associated Diarrhea," Digestive Diseases, 16:292-307 (1998).
Soriano et al., "The use of a fidaxomicin chaser as effective salvage therapy for vancomycin-refractory, recurrent Clostridium difficile infections," IDWeek 2013 Abstract, https://idsa.confex.com/idsa/2013/webprogram/Paper42591.html, (2013).
Soriano et al., "Novel Fidaxomicin Treatment Regimens for Patients With Multiple Clostridium difficile Infection Recurrences That Are Refractory to Standard Therapies," Open Forum Infectious Diseases, 1: 5-6 (2014).
Soriano et al., "The Use of a Fidaxomicin Taper/Pulsed Chaser as Effective Salvage Therapy for Vancomycin-Refractory, Recurrent Clostridium difficile Infections," Abstract, https://idsa.confex.com/idsa/2013/webprogram/Paper42591.html, (2013).
Tannock et al., "A new macrocyclic antibiotic, fidaxomicin (OPT-80), causes less alteration to the bowel microbiota of Clostridium difficile-infected patients than does vancomycin," Microbiology, 156: 3354-3359 (2010).
Wilström et al., "Frequency of antibiotic-associated diarrhoea in 2462 antibiotic-treated hospitalized patients: a prospective study," Journal of Antimicrobial Chemotherapy, 47: 43-50 (2001).
Moss, "Basic Terminology of Stereochemistry (IUPAC Recommendations 1996)," Pure & Applied Chemistry, 68: 2193-2222 (1996).
Crook et al., "Fidaxomicin Versus Vancomycin for Clostridum difficile Infection: Meta-analysis of Pivotal Randomized Controlled Trials," Clinical Infectious Diseases, 55: S93-S103 (2012).
Niu et al., "Characterization of a Sugar-O-methyltransferase TiaS5 Affords New Tiacumicin Analogues with Improved Antibacterial Properties and Reveals Substrate Promiscuity," ChemBioChem, 12: 1740-1748 (2011).
Ghantoji et al., "Economic healthcare costs of Clostridium difficile infection: a systematic review," Journal of Hospital Infection, 74: 309-318 (2010).
Mcfarlane et al., "Validation of a Three-Stage Compound Continuous Culture System for Investigating the Effect of Retention Time on the Ecology and Metabolism of Bacteria in the Human Colon," Microbial Ecology, 35: 180-187 (1998).
Porter, "Coating of Pharmaceutical Dosage Forms," in Remington's Pharmaceutical Sciences, 1666 (1990).
Remington's Pharmaceutical Sciences, 1644 (1990).
Chilton et al., "2013: -336. Comparison of Extended Duration Fidaxomicin Dosing Regimens for Treatment of Clostridium difficile Infection (CDI) in an in vitro Gut Model," http://www.icaaconline.com/php/icaac2013abstracts/data/papers/2013/K/2013_K-336.htm (2013).

* cited by examiner

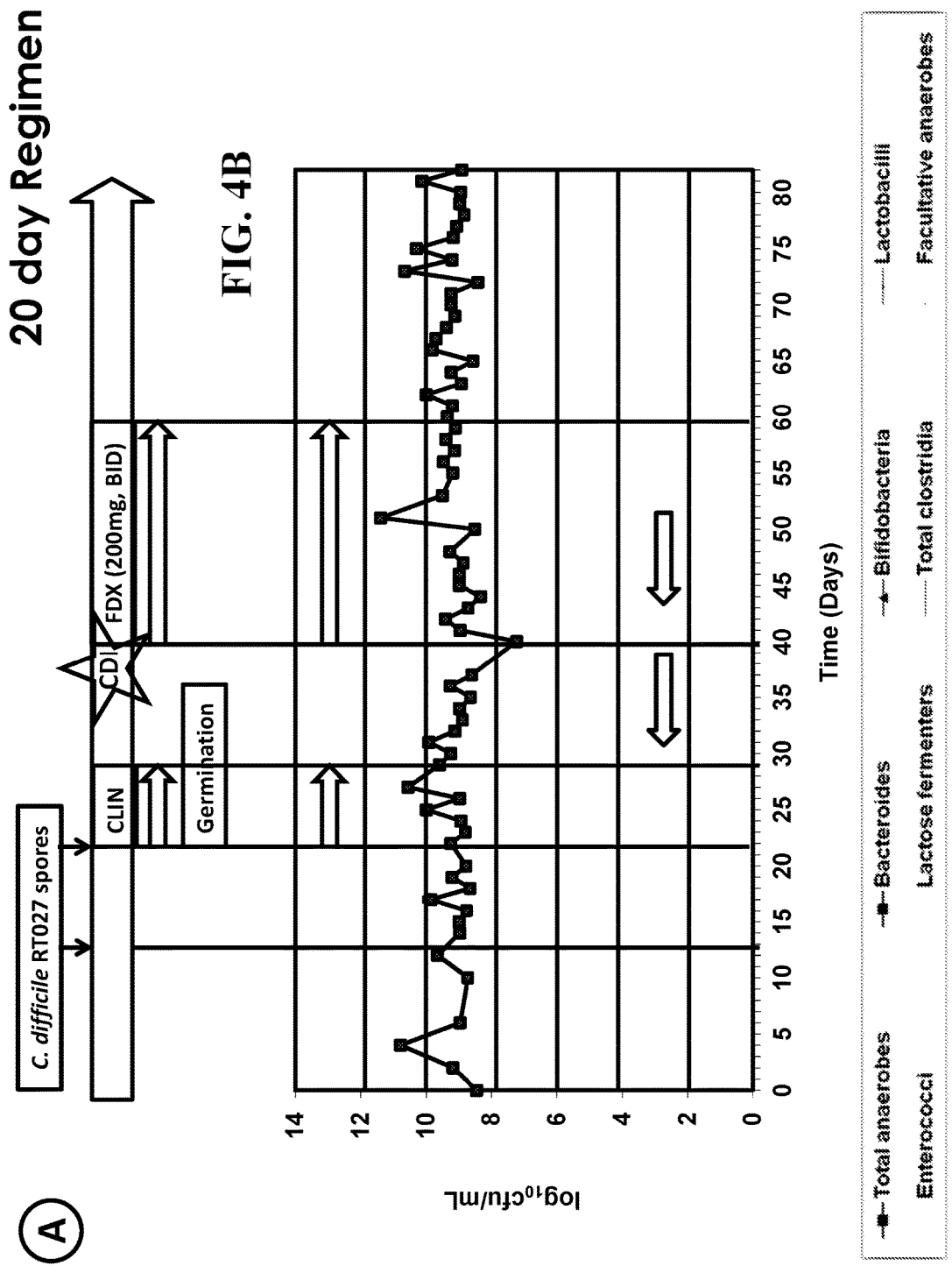

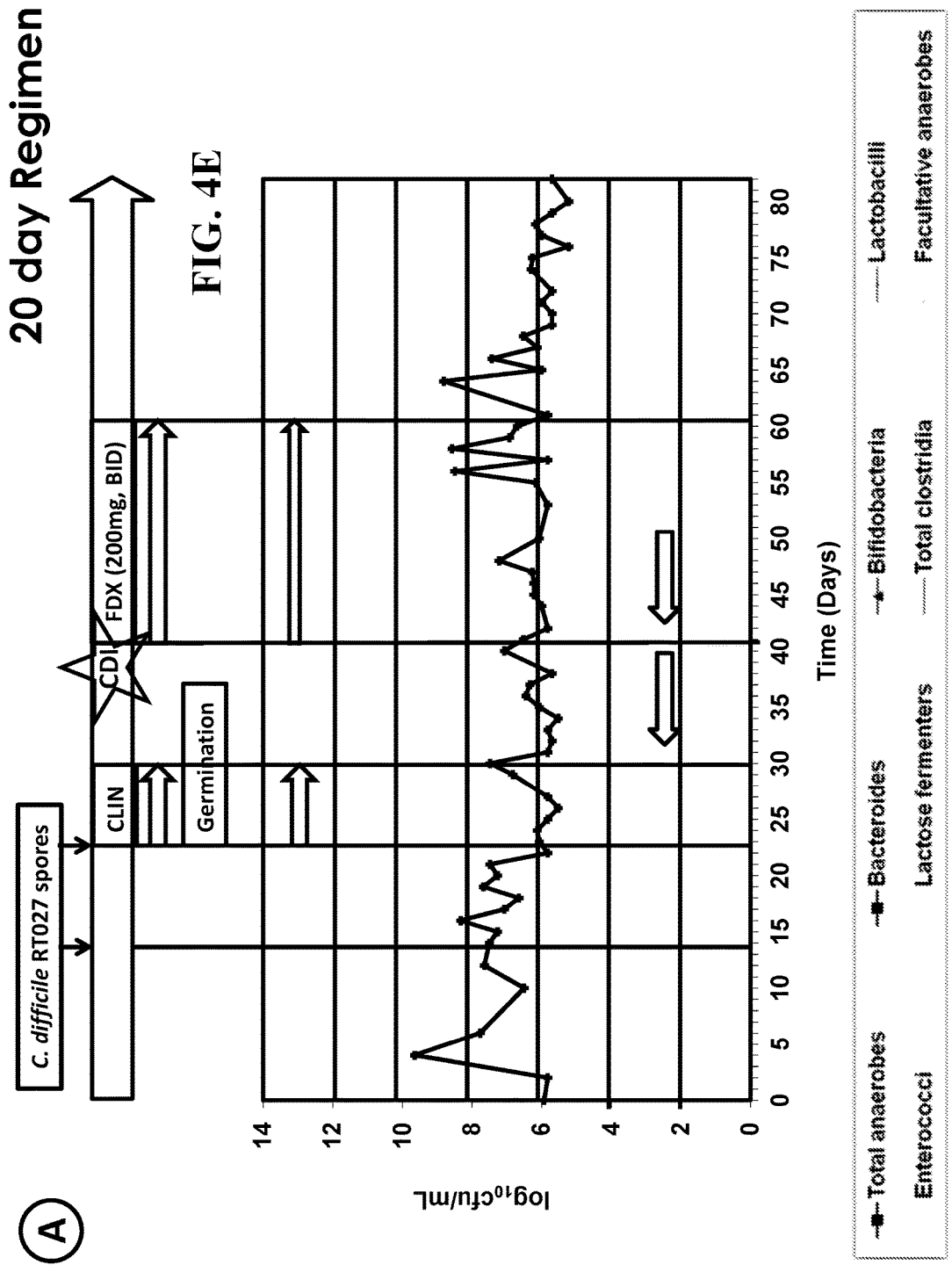

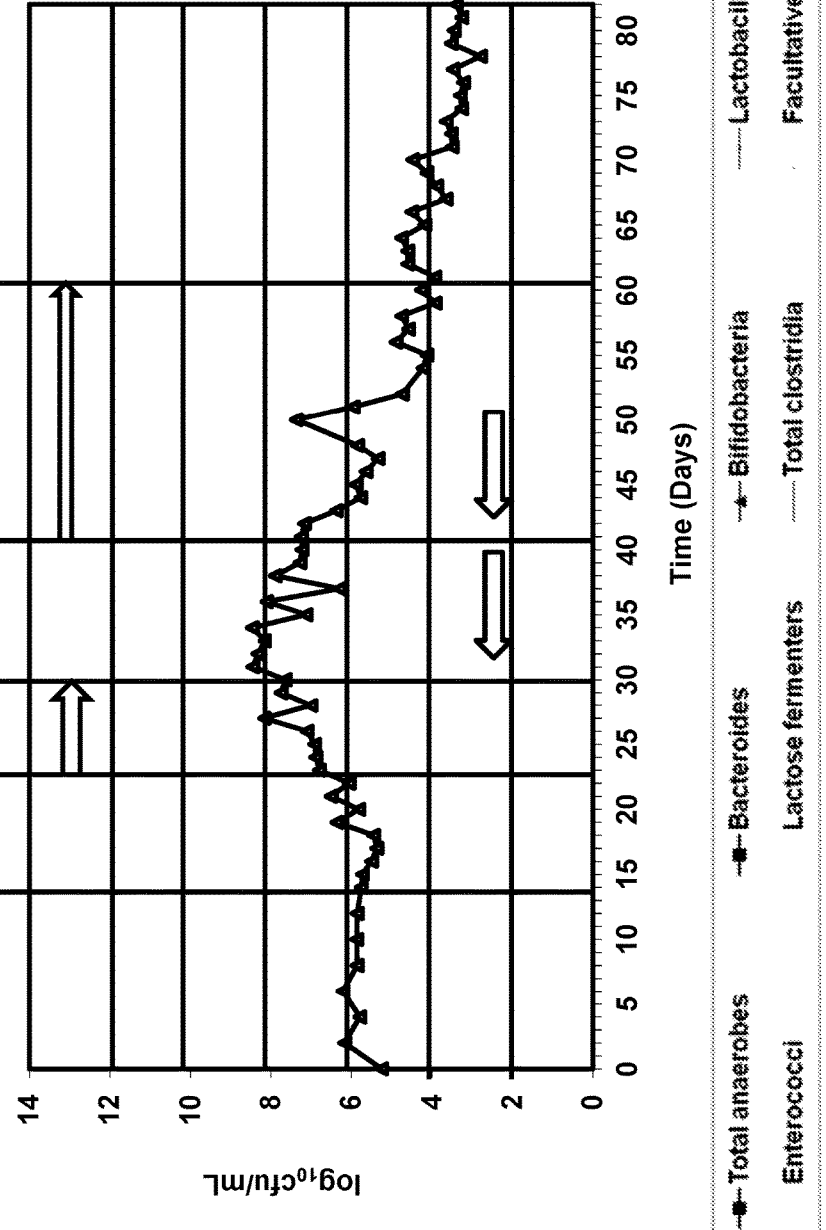

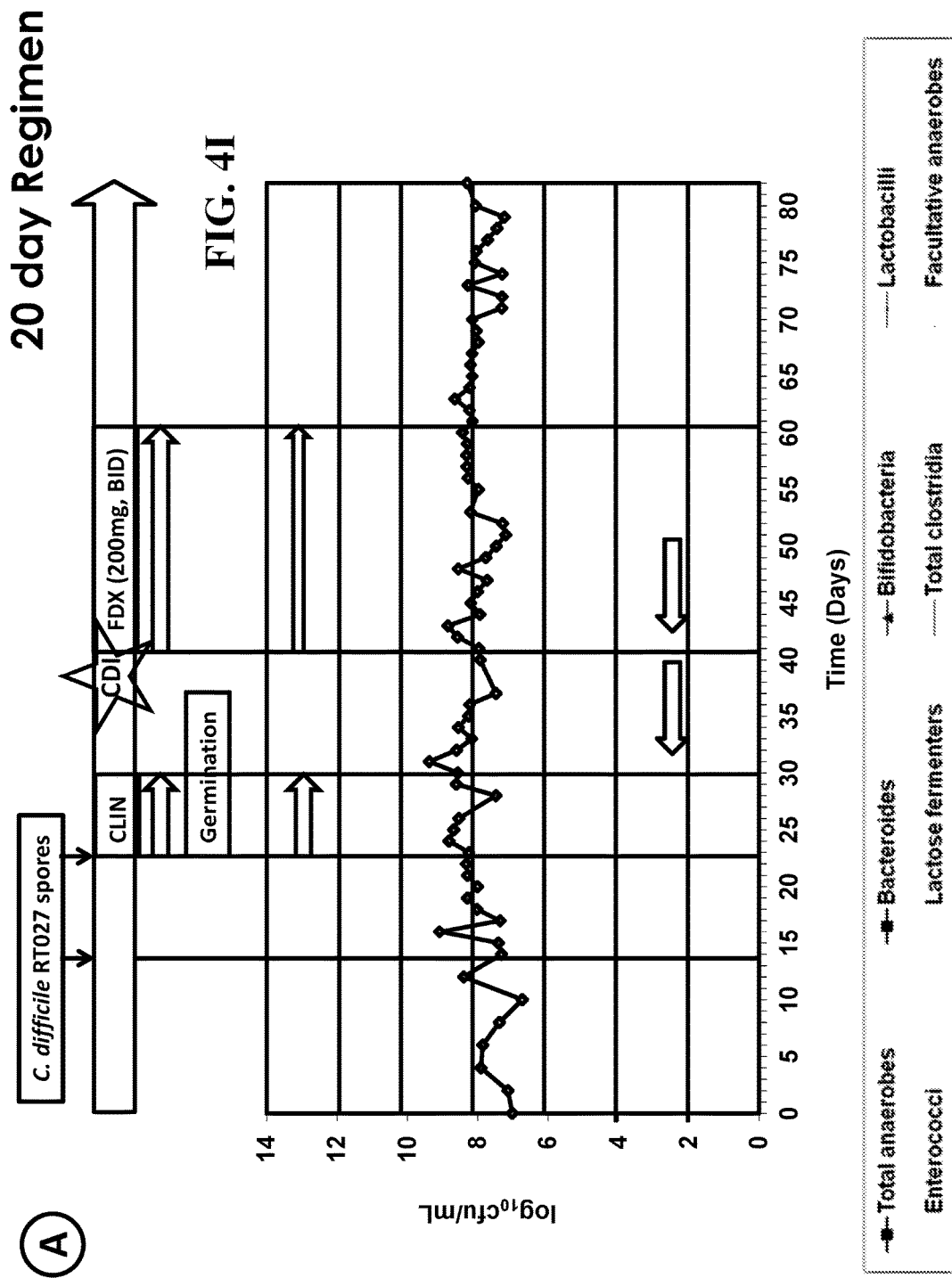

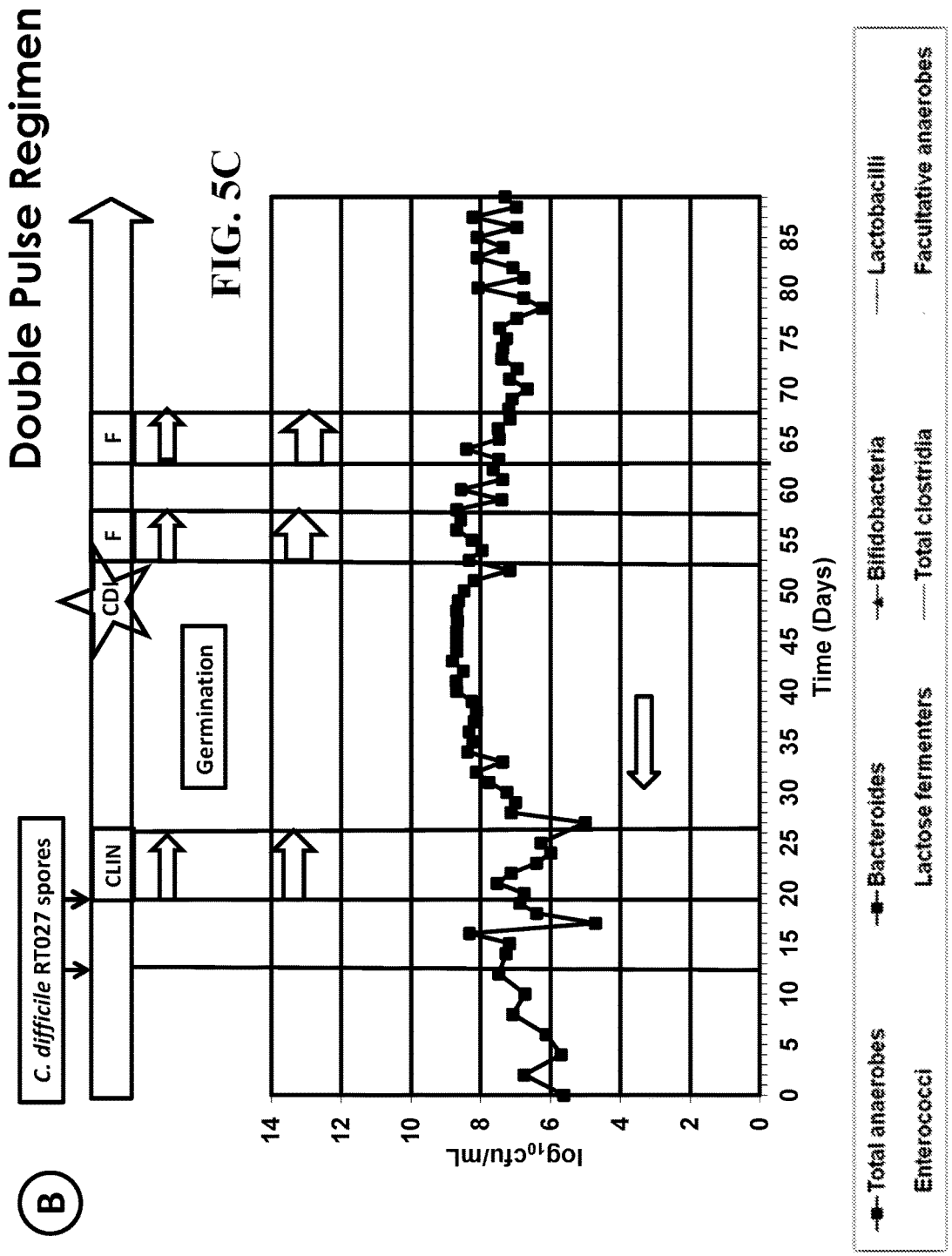

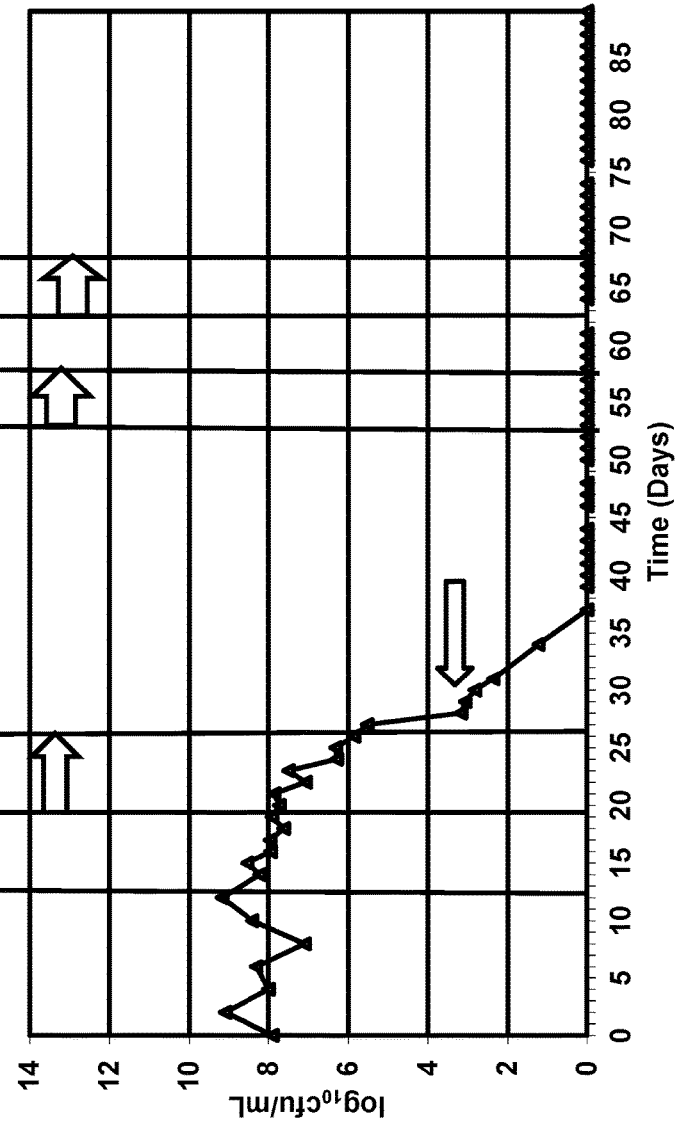

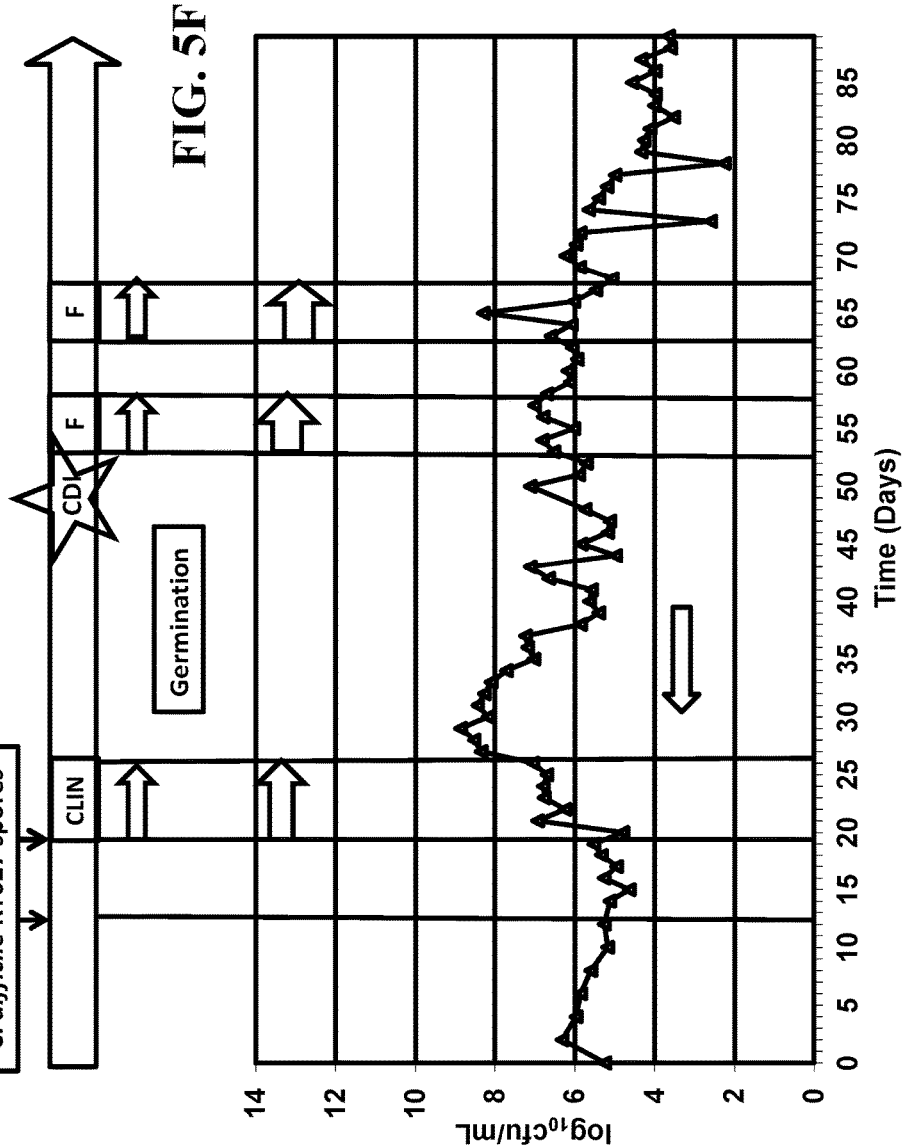

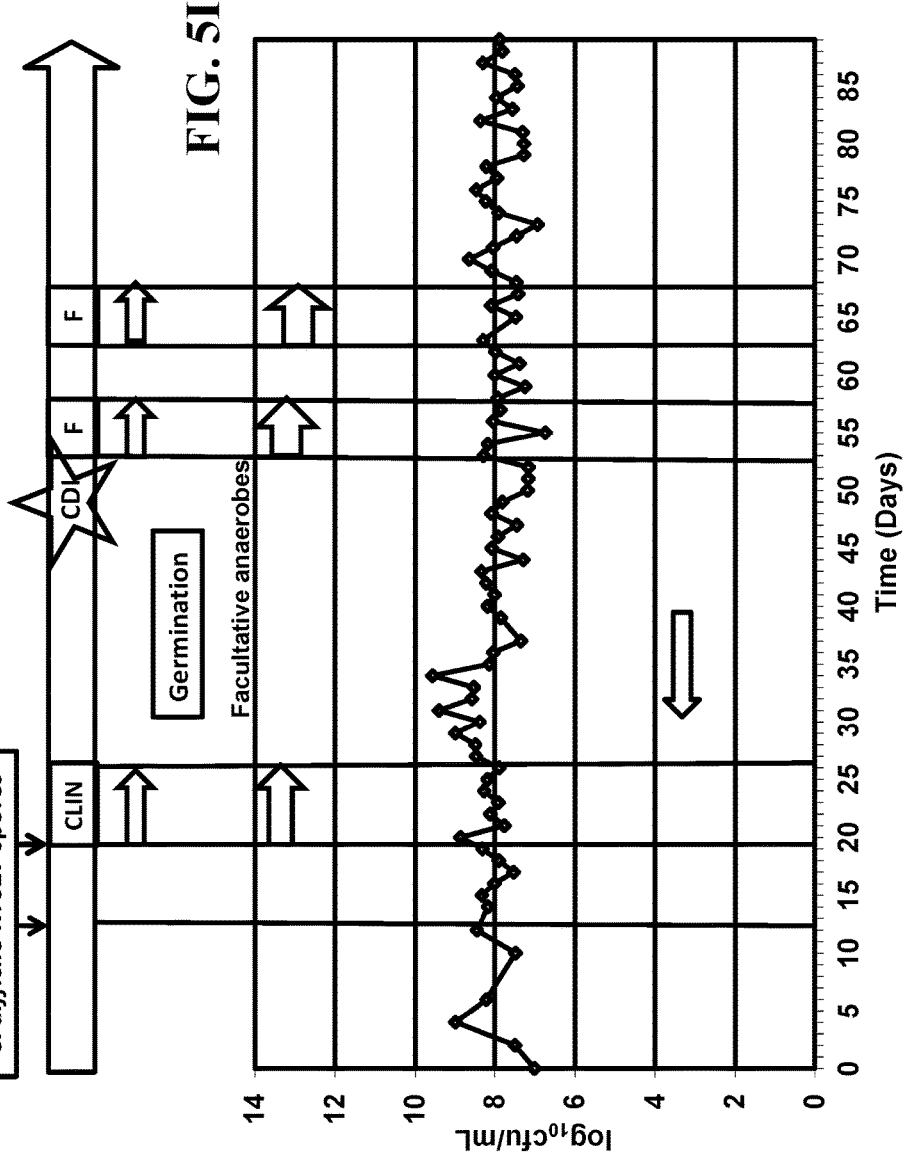

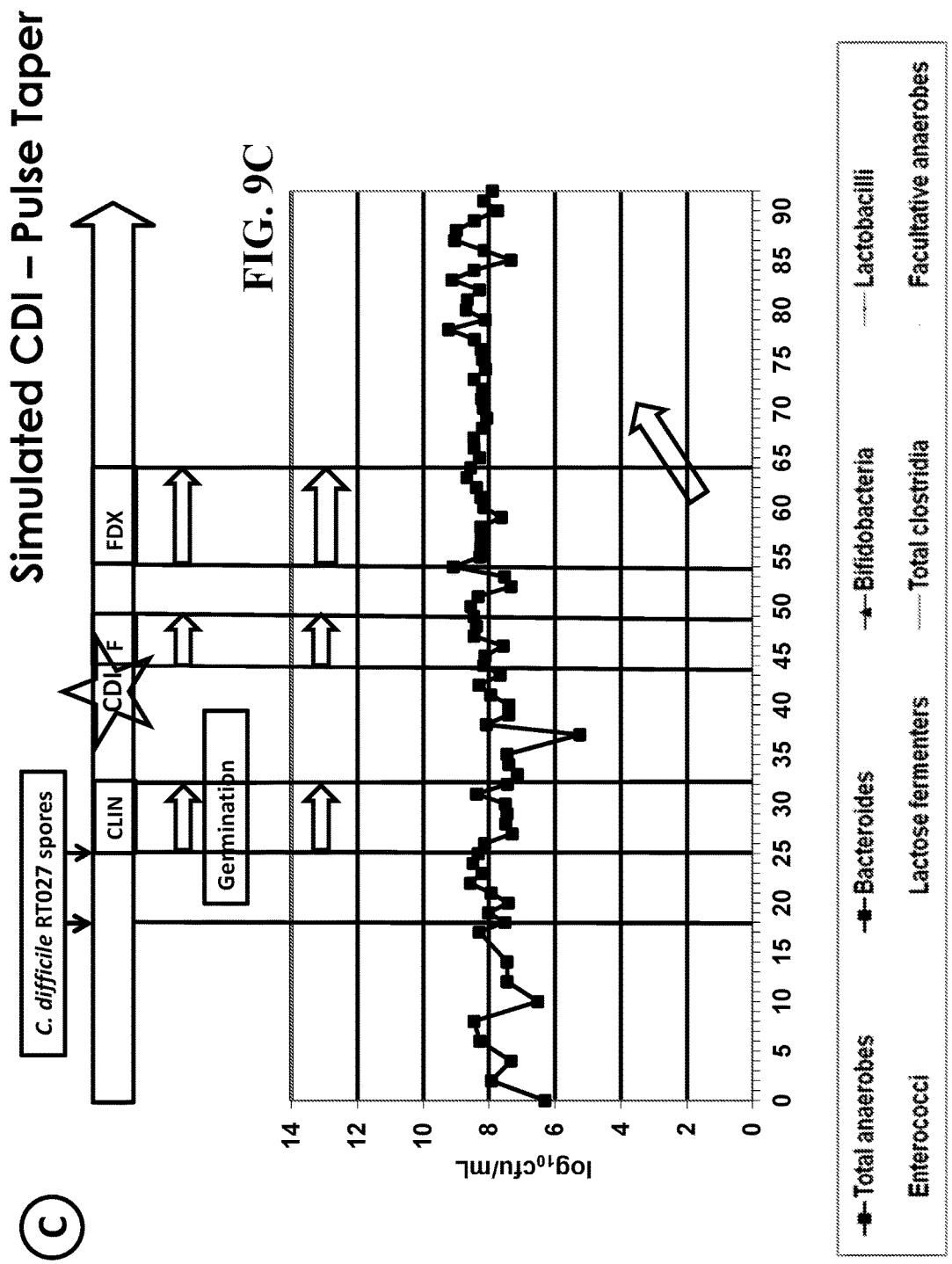

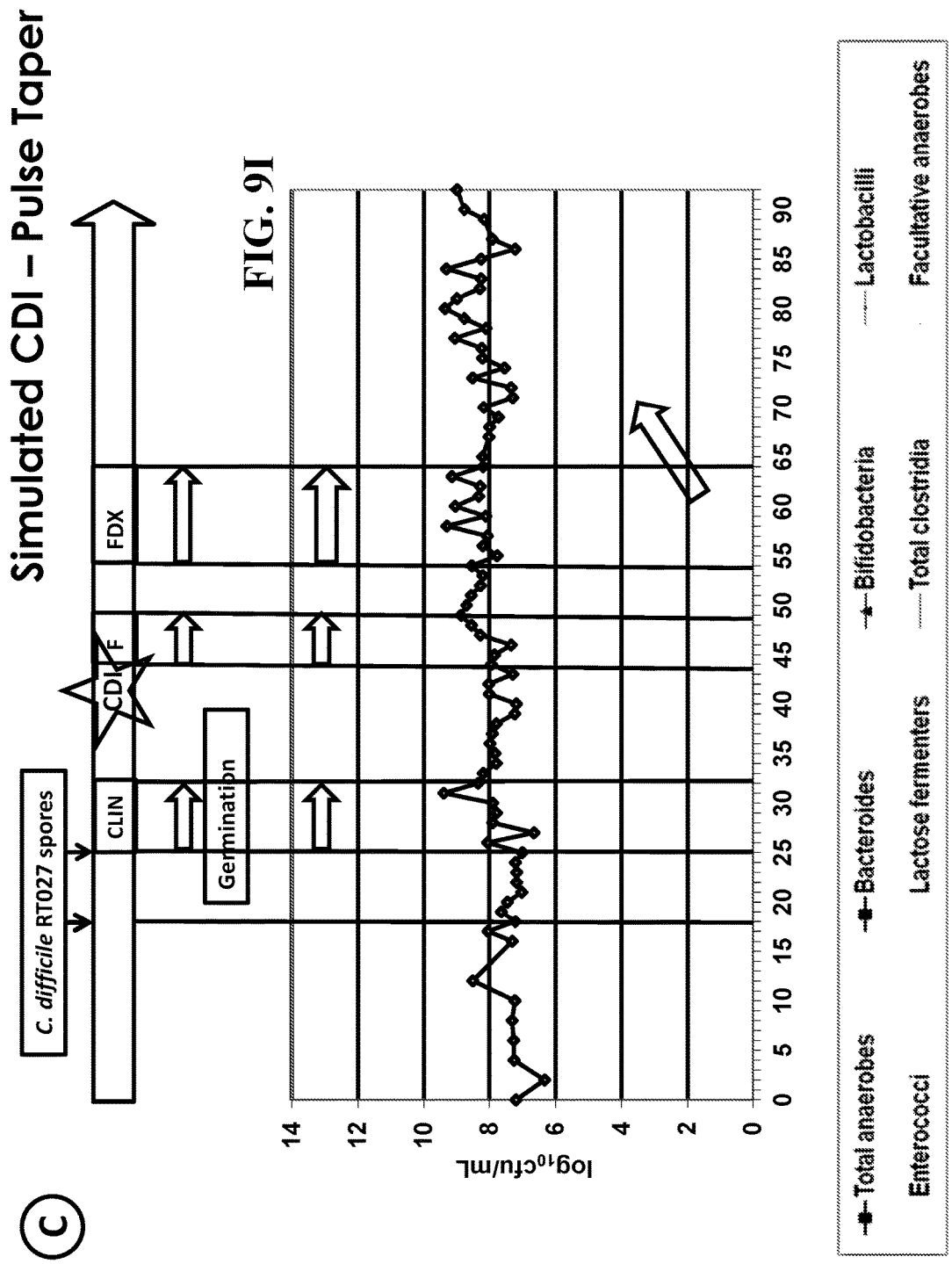

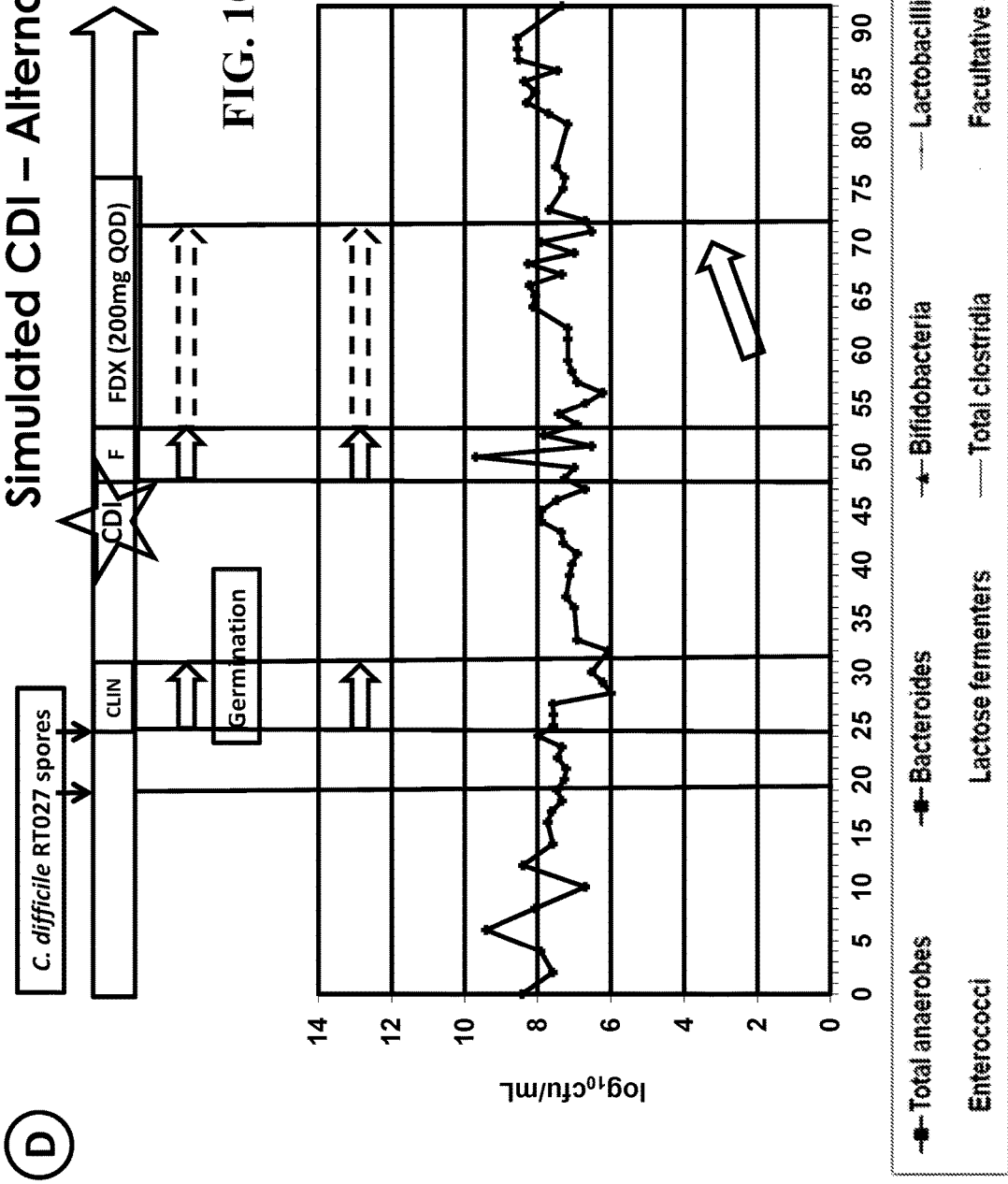

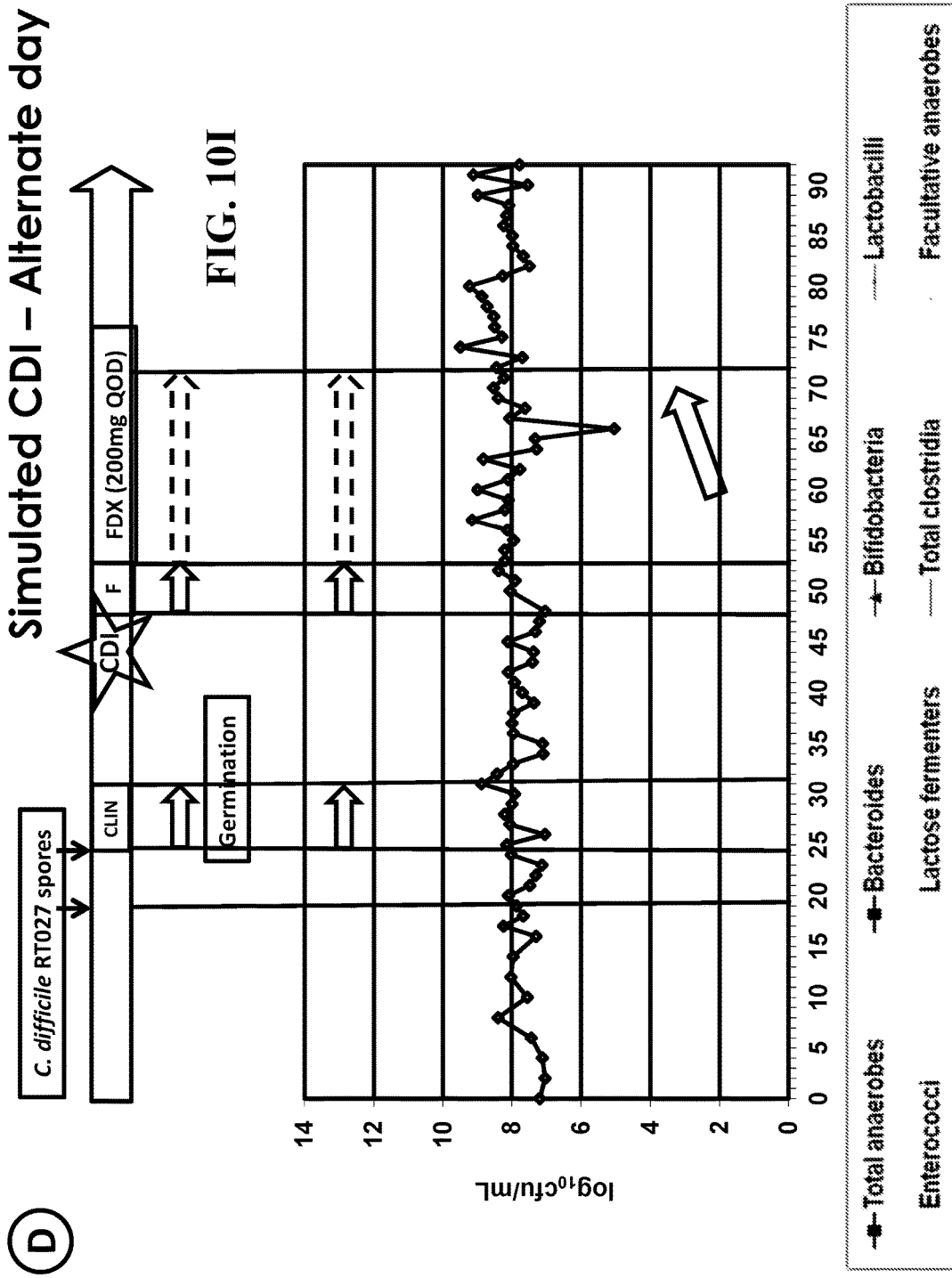

TREATMENT REGIMEN TIACUMICIN COMPOUND

The present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile* associated diarrhea/disease (CDAD) in a patient.

BACKGROUND OF THE INVENTION

Tiacumicin compounds are naturally occurring compounds with an antibiotic activity that can be obtained by cultivating various microorganisms belonging to the Actinoplanes family (especially the genus *Dactylosporangium aurantiacum*, subspecies hamdenensis) in a suitable nutrient medium at a suitable temperature and isolating the compounds having antibiotic activity against a variety of microorganisms (tiacumicins A-F; U.S. Pat. No. 4,918,174). Especially tiacumicins B and C turned out to possess antibiotic activity against a number of Gram-positive bacteria in vitro including strains resistant to therapeutic antibiotics, used at the time. U.S. Pat. No. 5,583,115 discloses dialkyltiacumicin compounds, which are derivatives of the above-mentioned tiacumicin compounds A-F, were found to have in vitro activity against a variety of bacterial pathogens and in particular against *Clostridium* species. U.S. Pat. No. 5,767,096 discloses bromotiacumicin compounds, which are also derivatives of tiacumicin compounds A-F, which were found to have in vitro activity against some bacterial pathogens and in particular against *Clostridium* species.

From a chemical point of view the tiacumicins share an 18-membered macrocyclic ring, which is glycosidically attached to one or two optionally substituted sugar molecules (U.S. Pat. No. 4,918,174 and WO 2004/014295) as follows:

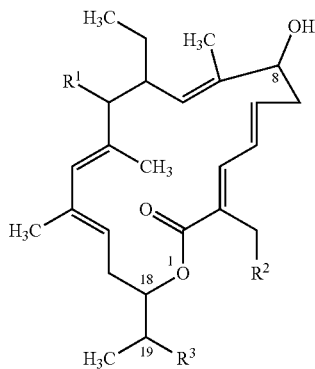

Formula I

WO 2004/014295 describes substantially pure R-tiacumicins, obtained by submerged aerobic fermentation of *Dactylosporangium aurantiacum* hamdenensis. WO 2006/085838 discloses pharmaceutical compositions containing R-tiacumicins and especially R-tiacumicin B, which contains an R-hydroxy-group at C19, which shows surprisingly lower MIC values when tested in vitro against *Clostridium* species than the optically pure S-isomer of tiacumicin B and other tiacumicin related compounds.

Chinese patent applications having publication numbers 102030791 and 102219815 respectively and S. Niu et al. (2011) in ChemBioChem 12: page 1740-1748 describe 11 new tiacumicin analogues all lacking the 2'-O-methyl group on the internal rhamnose moiety. Two of those analogues have shown to have improved antibacterial properties.

R-tiacumicin B is also known under the name fidaxomicin (3-[[[6-deoxy-4-O-(3,5-dichloro-2-ethyl-4,6-dihydroxybenzoyl)-2-O-methyl-β-D-mannopyranosyl]oxy]methyl]-12(R)-[[6-deoxy-5-C-methyl-4-O-(2-methyl-1-oxopropyl)-β-D-lyxo-hexopyranosyl]oxy]-11(S)-ethyl-8(S)-hydroxy-18(S)-(1(R)-hydroxyethyl)-9,13,15-trimethyloxacyclooctadeca-3,5,9,13,15-pentaene-2-one or oxacyclooctadeca-3,5,9,13,15-pentaen-2-one, 3-[[[6-deoxy-4-O-(3,5-dichloro-2-ethyl-4,6-dihydroxybenzoyl)-2-O-methyl-β-D-mannopyranosyl]oxy]methyl]-12-[[6-deoxy-5-C-methyl-4-O-(2-methyl-1-oxopropyl)-β-D-lyxo-hexopyranosyl]oxy]-11-ethyl-8-hydroxy-18-[(1R)-1-hydroxyethyl]-9,13,15-trimethyl-, (3E,5E,8S,9E,11S,12R,13E,15E,18S)). It is a compound that has a narrow antimicrobial spectrum, with activity against *Clostridium difficile* and most strains of staphylococci and enterococci but negligible activity against gram-negative organisms and fungi. It is obtained by fermentation of *Dactylosporangium aurantiacum* and corresponds to the following formula (II):

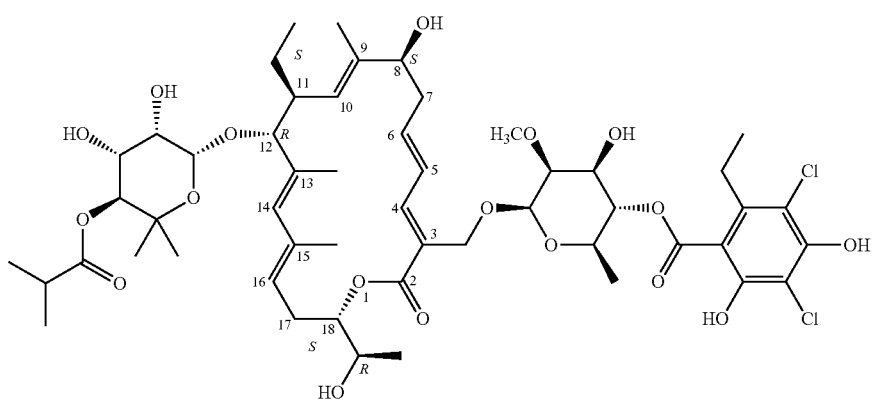

II

According to an in vitro BCS study, fidaxomicin is a BCS (Biopharmaceutics Classification System) Class IV compound (low solubility, low permeability). Upon oral administration fidaxomicin is poorly absorbed from the intestinal tract and is therefore associated with a low incidence of systemic side effects.

Tablets containing 200 mg fidaxomicin are commercially available in Europe (under the trademark Dificlir) and in the USA (under the trademark Dificin).

Not pre-published international patent application PCT/EP2014/000091 discloses compositions containing a tiacumicin compound in admixture with an excipient, selected from the group consisting of xanthan gum, carrageenan, sodium alginate, guar gum, water dispersible cellulose (microcrystalline cellulose and sodium carboxymethylcellulose) and mixtures thereof, which is used as an anti-foaming agent for the preparation of stabilised suspension formulations.

Fidaxomicin is indicated for the treatment of *Clostridium difficile* infections (CDI) also known as *C. difficile*-associated diarrhea or disease (CDAD) and prevention of recurrences. CDI is a major burden on healthcare facilities worldwide (Wiegand P. N., Nathwani D., Wilcox M. H. et al. in J. Hosp Infect of 10 Apr. 2012; Ghantoji S. S., Sail, K. Lairson D. R. (2010) in J. Hosp. Infect. 74: 309-318). These infections are normally caused by changes in the composition and function of the intestinal flora following the use of antimicrobials and are called antibiotic-associated diarrhea (AAD).

A *Clostridium difficile* infection is a type of bacterial infection that can affect the digestive system. It most commonly affects people who have been treated with antibiotics. The symptoms of a *C. difficile* infection can range from mild to severe and include diarrhea, a high temperature (fever) of above 38° C. and painful abdominal cramps. A *C. difficile* infection can also lead to life-threatening complications such as severe swelling of the bowel from a build-up of gas (toxic megacolon). *Clostridium difficile* infections (CDI) also known as *C. difficile*-associated disease (CDAD) refers to a wide spectrum of diarrheal illnesses caused by the toxins produced by this organism, including cases of severe colitis with or without the presence of pseudomembranes. The occurrence of AAD varies greatly and is influenced by a number of factors, including nosocomial outbreaks, patterns of antimicrobial prescription, and individual susceptibility. It is estimated that 10% to 15% of all hospitalized patients treated with antibiotics will develop AAD. Most important, twice as many will become asymptomatic carriers. Risk factors include compromised immune status, advanced age, abdominal surgery, comorbidity, types and prolonged use of antibiotics, reduced gastric acid, and the length of hospitalization. For example, infection rates for *C. difficile* are reported to be around 10% after 2 weeks of hospitalization but may reach 50% after 4 or more weeks (McFarland L V. Epidemiology, risk factors and treatments for antibiotic-associated diarrhea. Dig Dis 1998; 16:292-307). All groups of antibiotics may cause AAD, but those with broad-spectrum coverage—in particular cephalosporins, fluoroquinolones, extended-coverage penicillins, and clindamycin—are the most common culprits (Wistrom J, Norrby S R, Myhre E, et al. Frequency of antibiotic-associated diarrhoea in 2462 antibiotic-treated hospitalized patients: a prospective study. J Antimicrob Chemother 2001; 47:43-50).

Treatment options are limited and are associated with effects on gut microflora recovery of the patients and high rates of recurrence.

Therefore it remains a need for improved treatment options and dosage regimens. Along with its narrow antimicrobial spectrum, fidaxomicin also has a prolonged post-antibiotic effect against *C. difficile*. Besides the obvious benefit to the patient, the prevention of recurrence would eliminate the costs of treating additional episodes of *C. difficile* infection and should reduce the rate of person-to-person transmission. The currently recommended treatment regimen for adults and elderly people (65 years and older) is 200 mg administered twice daily (q12 h) for 10 days.

This is an effective treatment for CDI, and is associated with reduced rates of recurrence as compared with vancomycin. However, this treatment/dosing regimen was not optimised for recovery of microflora but chosen based on existing practice for vancomycin and metronidazole. Both vancomycin and metronidazole disrupt microflora and so on recovery cannot start until after treatment has been removed. In two Phase III randomised, double-blind, clinical trials, fidaxomicin demonstrated non-inferiority to vancomycin for initial clinical cure of CDI, but superiority in reduction of recurrence and sustained clinical response (Crook et al. (2012) in Clin. Infect. Dis. 55(Suppl 2): S93-103).

In phase III clinical trials the risk of fidaxomicin or vancomycin treatment failure doubled for each treatment day less than 10 days (T. Louie et al. Poster presented at $22^{nd}$ European Congress of Clinical Microbiology & Infectious Diseases, Mar. 31-Apr. 3, 2012, London). The relatively low impact of fidaxomicin on gut microflora may allow better recovery of bacteria during prolonged treatment periods, so reducing risk of CDI recurrence (T. J. Louie et al. (2012) in Clin. Infect. Dis. 55(S2) S132-142; Tannock in Microbiology (2010), 156, 3354-3359 (Phase II trials)).

The management of *C. difficile* infections (CDI), thus, is complicated by high recurrence rates with over 50% of second episodes experiencing a recurrence (RCDI). Guidelines recommend managing multiple recurrences with a vancomycin taper. No clear recommendation is available for patients failing this approach. In a recent case series report (Soriano et al in Exp Rev Antiinf Ther 2013; 11:767-776), patients with multiple RCDI that were refractory to vancomycin taper therapy were given either fidaxomicin 200 mg BID for 10 days (FID-TX), or a repeat of CDI treatment followed by either a 10-day fidaxomicin regimen as a chaser (FID-CH), or a taper as 200 mg daily for 7 days, followed by 200 mg QOD for 7-26 days (FID-TP). Demographic information, CDI history, treatment outcomes, and symptom-free interval (SFI) were collected from patient records. Treatment success was considered if symptoms resolved by the end of therapy and no additional antibiotic was needed. RCDI was defined by the onset of CDI symptoms following successful treatment for a previous episode. 14 patients received 18 courses of fidaxomicin for RCDI (mean age of 60, mean of 4.6 previous CDI episodes, mean of 2.3 previous vancomycin taper courses). All 18 courses resulted in treatment success (3 courses as FID-TX, 8 as FID-CH, and 7 as FID-TP). Of 3 FID-TX courses, there were 2 RCDI episodes (66%). When excluding RCDI due to antimicrobial exposure, there were 2 RCDI (25%) observed after the 8 FID-CH courses and no RCDI following the 7 FID-TP courses. The average SFI following a vancomycin taper was 37 days. The average SFI following FID-TX, FID-CH, and FID-TP was 73, 240, and 150 days, respectively. Patients with RCDI that failed multiple vancomycin tapers had symptom resolution following fidaxomicin therapy. All 3 regimens provided a greater SFI compared to a vancomycin taper. No patient experienced RCDI following FID-TP. FID-CH had the longest SFI, yet follow-up time with FID-TP was shorter given more recent adoption of this regimen. These results suggest the utility of using fidaxomicin to treat RCDI. (M. M. Soriano et al. Abstract 42591; presentation No. 1410; IDWeek, 5 Oct. 2013).

The use of fidaxomicin for the treatment of *Clostridium difficile* infections (CDI) or *Clostridium difficile* associated diarrhea or disease (CDAD) in an adult patient wherein the dosage regime is selected from the group consisting of:
 a. 200 mg of fidaxomicin BID (Latin: bis in die; which means twice a day) for 20 days (reference example Model A)
 b. 200 mg of fidaxomicin BID for 5 days followed by 5 days of rest and then 200 mg BID for a further 5 days (double pulse) (reference example Model B)
was mentioned by C. H. Chilton during the ICAAC congress in September 2013 (reference example; C. H. Chilton et al. (2013) in J. Antimicrobial Chemotherapy Advance Access September 2013 and C. H. Chilton et al., abstract 23$^{rd}$ European Congress of Clinical microbiology & Infectious Disease, Apr. 27-30, 2013, Berlin).

However, there still is a need to find a modified dosing regimen for tiacumicin compounds and in particular for fidaxomicin that combines efficacy, recovery of gut micro flora or a reduced effect on gut microflora, a reduction of recurrence, and a low chemical burden to the patients with cost-effectiveness.

SUMMARY OF THE INVENTION

After having carried out detailed investigations, the present inventors have been able to provide one or more of a tiacumicin compound, a stereo-isomer thereof, a polymorph thereof or a pharmaceutically acceptable solvate thereof, as well as a pharmaceutical composition, comprising one or more of a tiacumicin compound, a stereo-isomer thereof, a polymorph thereof or a pharmaceutically acceptable solvate thereof, for use in the oral treatment of *Clostridium difficile* infections (CDI) or *Clostridium difficile* associated diarrhea or disease in a patient, according to a dosage regimen which is selected from the group consisting of:
 i. 200 mg of the tiacumicin compound BID for 5 days followed by 5 days of rest and then 200 mg once daily for a further 10 days and
 ii. 200 mg of the tiacumicin compound BID for 5 days followed by a single 200 mg every other day for 20 days.

Further, the inventors have provided a method for recovering of gut Bifidobacteria population in log 10 cfu/ml in a patient, suffering from *Clostridium difficile* infections (CDI) or *Clostridium difficile* associated diarrhea or disease (CDAD) and receiving oral treatment with a tiacumicin compound, a stereo-isomer thereof, a polymorph thereof or a pharmaceutically acceptable solvate thereof, to 50 to 90% of the gut Bifidobacteria population in log 10 cfu/ml prior to administering the tiacumicin compound during days 15-45 after start of the treatment by orally administering the tiacumicin compound to the patient according to a dosage regimen, which is selected from the group consisting of:
 i. Administering 200 mg of the tiacumicin compound BID for 5 days followed by 5 days of rest and then 200 mg once daily for a further 10 days and
 ii. Administering 200 mg of the tiacumicin compound BID for 5 days followed by a single 200 mg every other day for 20 days.

BRIEF DESCRIPTION OF THE DRAWINGS

FIG. 4B provides a graphical representation of the total anaerobes level versus time in days for the reference example A.

FIG. 4E provides a graphical representation of the Lactobacilli level versus time in days for the reference example A.

FIG. 4F provides a graphical representation of the Enterococci level (triangles) versus time in days for the reference example A.

FIG. 4I provides a graphical representation of the facultative anaerobes level (diamonds/*rhombi*) versus time in days for the reference example A.

FIG. 5C provides a graphical representation of the *Bacteroides* level versus time in days for the reference example B.

FIG. 5D provides a graphical representation of the Bifidobacteria level versus time in days for the reference example B.

FIG. 5F provides a graphical representation of the Enterococci level (triangles) versus time in days for the reference example B.

FIG. 5I provides a graphical representation of the facultative anaerobes level (diamonds/*rhombi*) versus time in days for the reference example B.

FIG. 9C provides a graphical representation of the *Bacteroides* level versus time in days for the example C.

FIG. 9I provides a graphical representation of the facultative anaerobes level (diamonds/*rhombi*) versus time in days for the example C.

FIG. 10H provides a graphical representation of the total clostridia level (crosses) versus time in days for the example D.

FIG. 10I provides a graphical representation of the facultative anaerobes level (diamonds/*rhombi*) versus time in days for the example D.

DETAILED DESCRIPTION OF THE INVENTION

Figure 1:
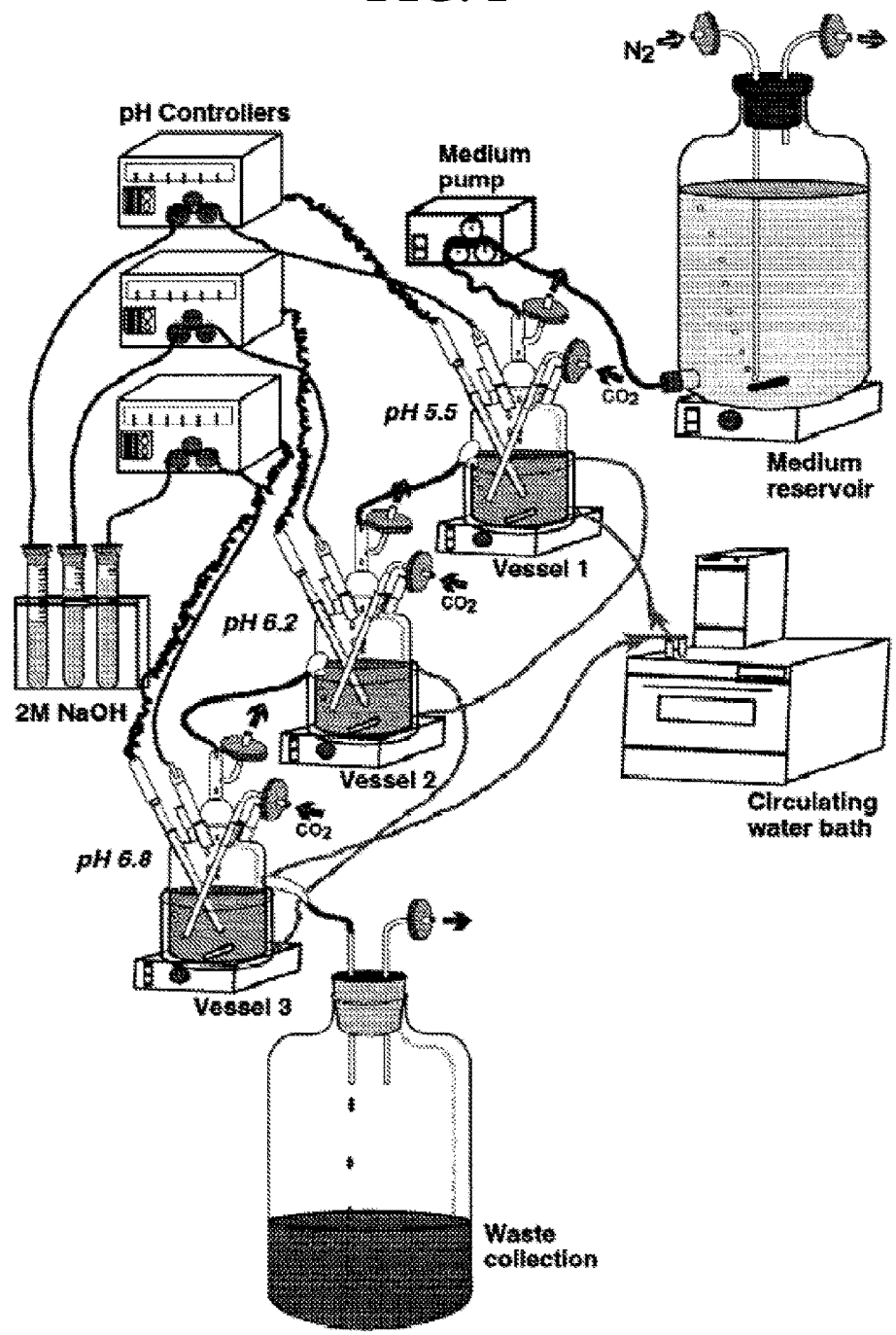
FIG. 1 represents the three-stage compound continuous culture system used in example 1, as described by Macfarlane et al. (Microbial Ecology (1998), 35: 180-187).
Figure 2:
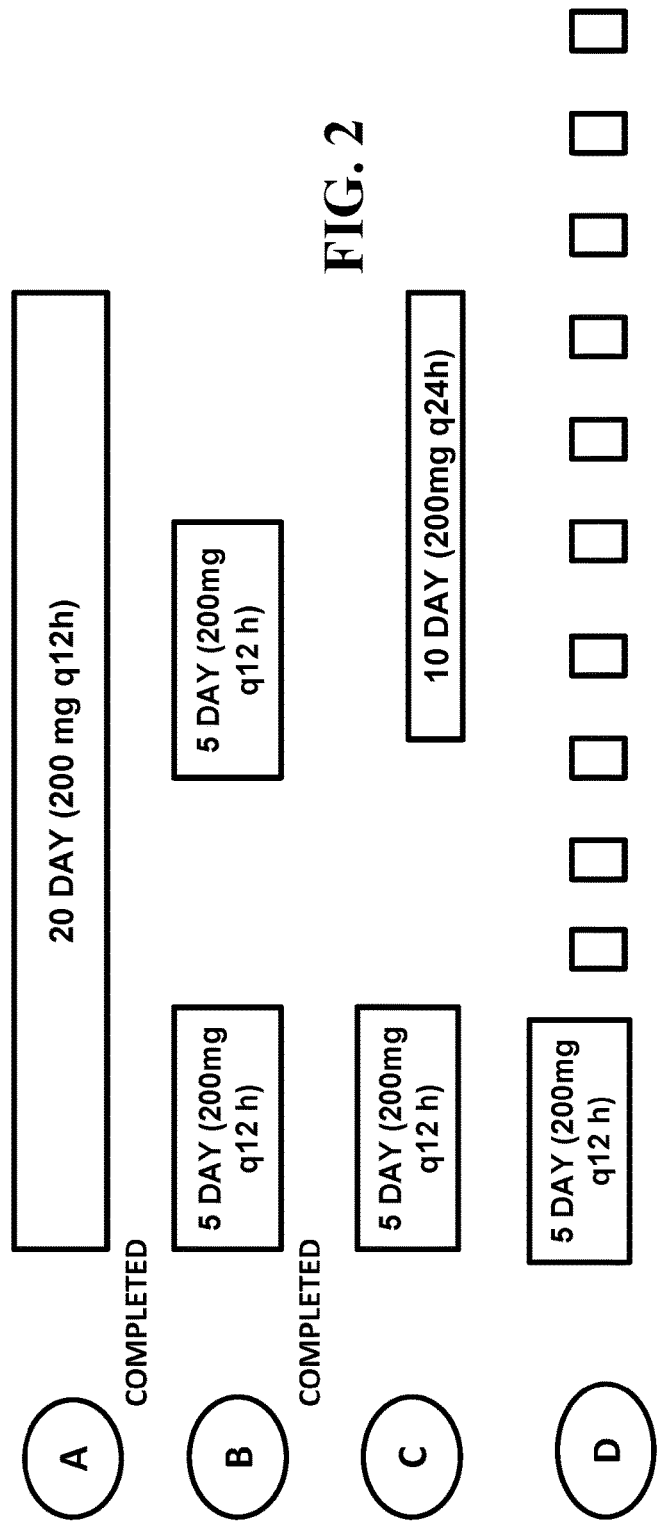
FIG. 2 provides a graphical representation of the treatment regimens for the reference example (A and B) and example 1 (C and D; treatment regimens i and ii).
Figure 3:
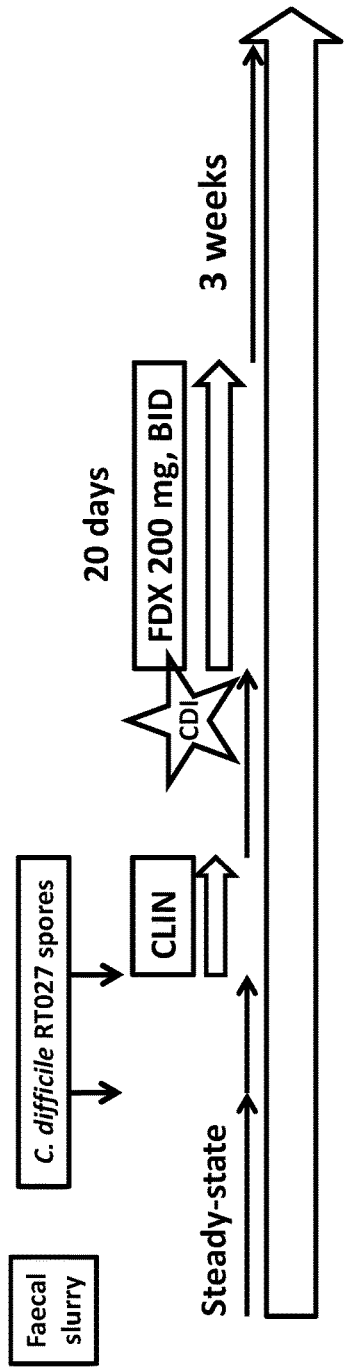
FIG. 3 provides the experimental design for the reference example (A and B).
Figure 3:
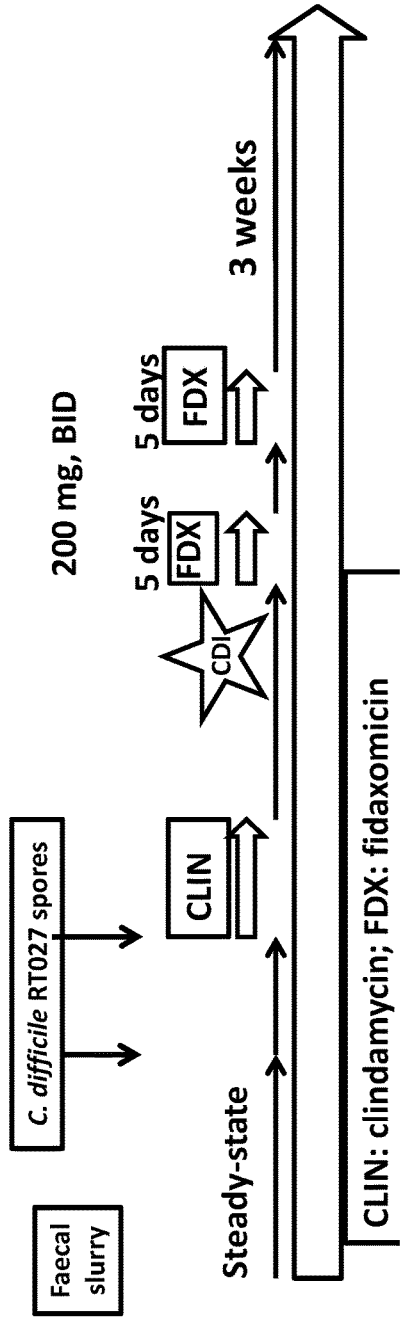
Figure 4A:
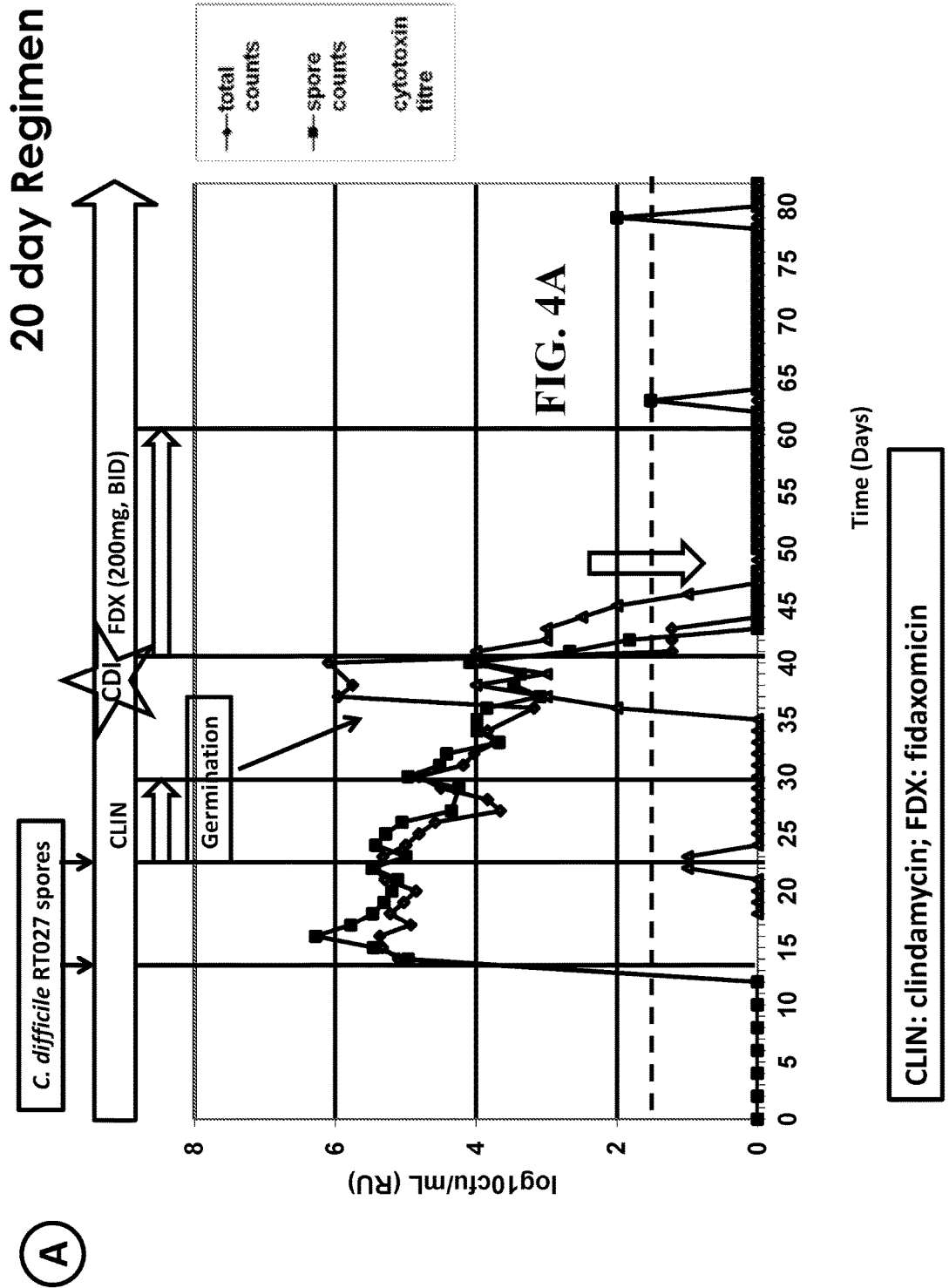
FIG. 4A provides a graphical representation of the total counts (diamonds/*rhombi*), spore counts (squares) and cytotoxin titre (triangles) versus time in days for the reference example A.
Figure 4C:
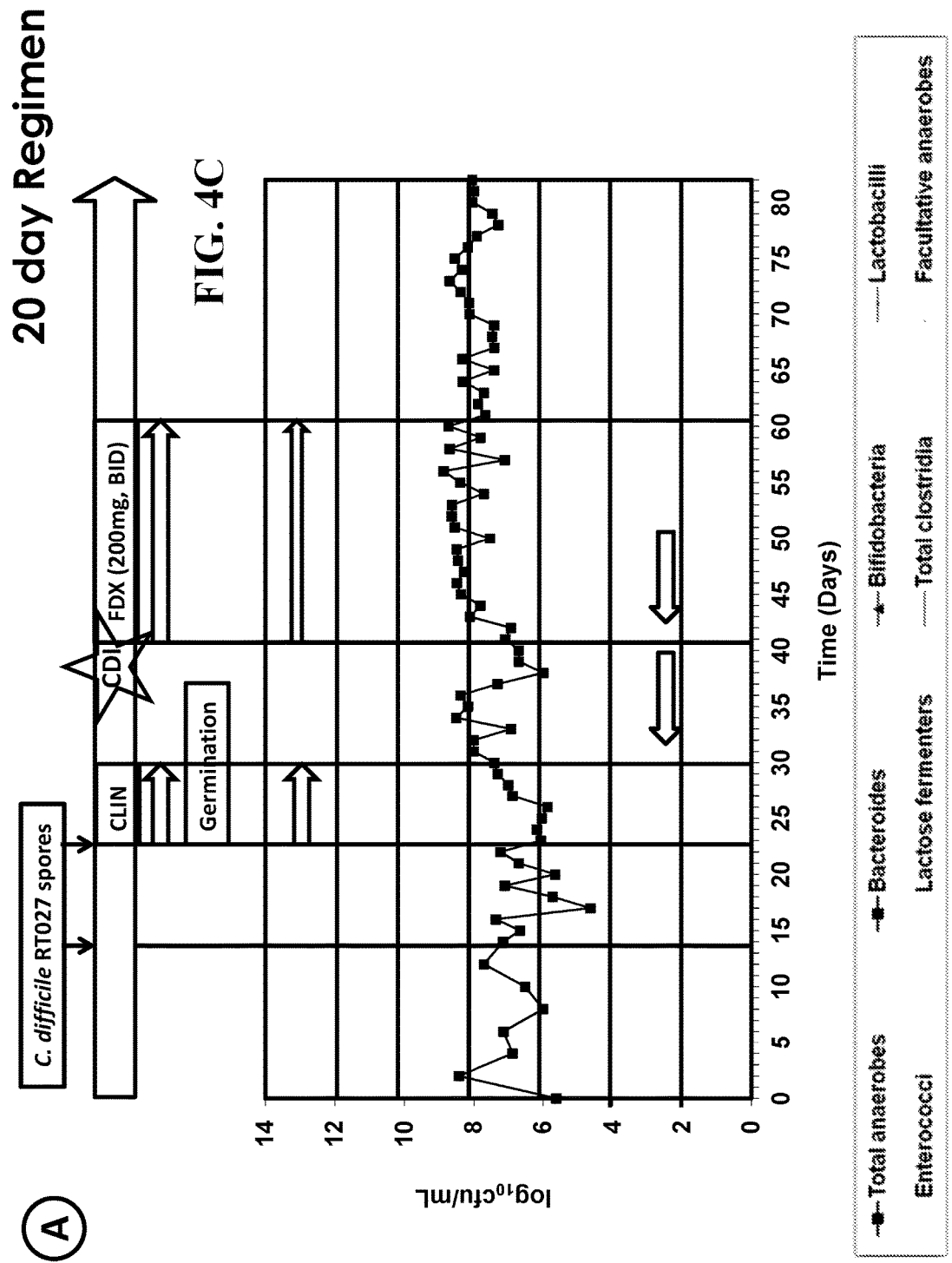
FIG. 4C provides a graphical representation of the *Bacteroides* level versus time in days for the reference example A.
Figure 4D:
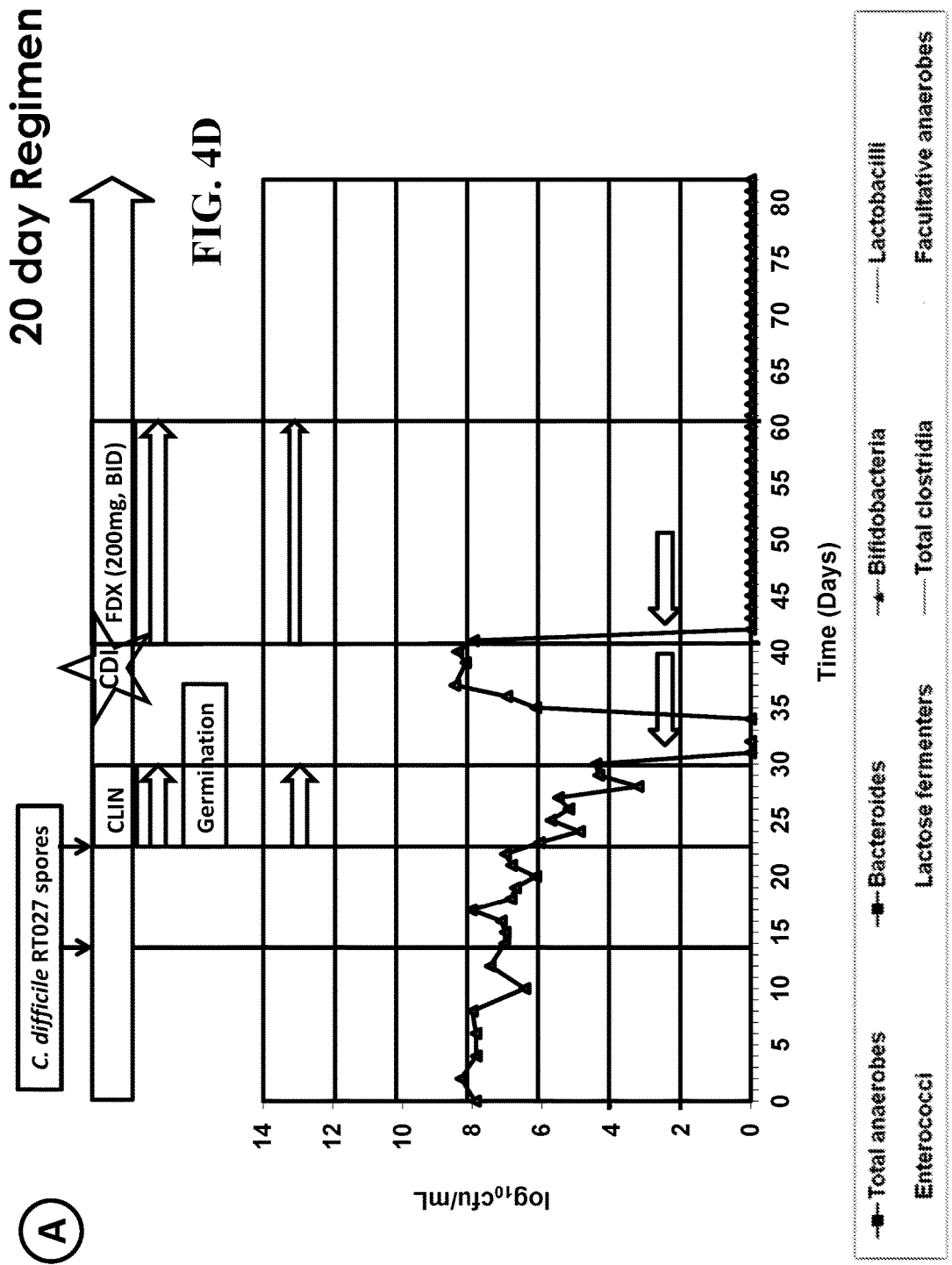
FIG. 4D provides a graphical representation of the Bifidobacteria level versus time in days for the reference example A.
Figure 4G:
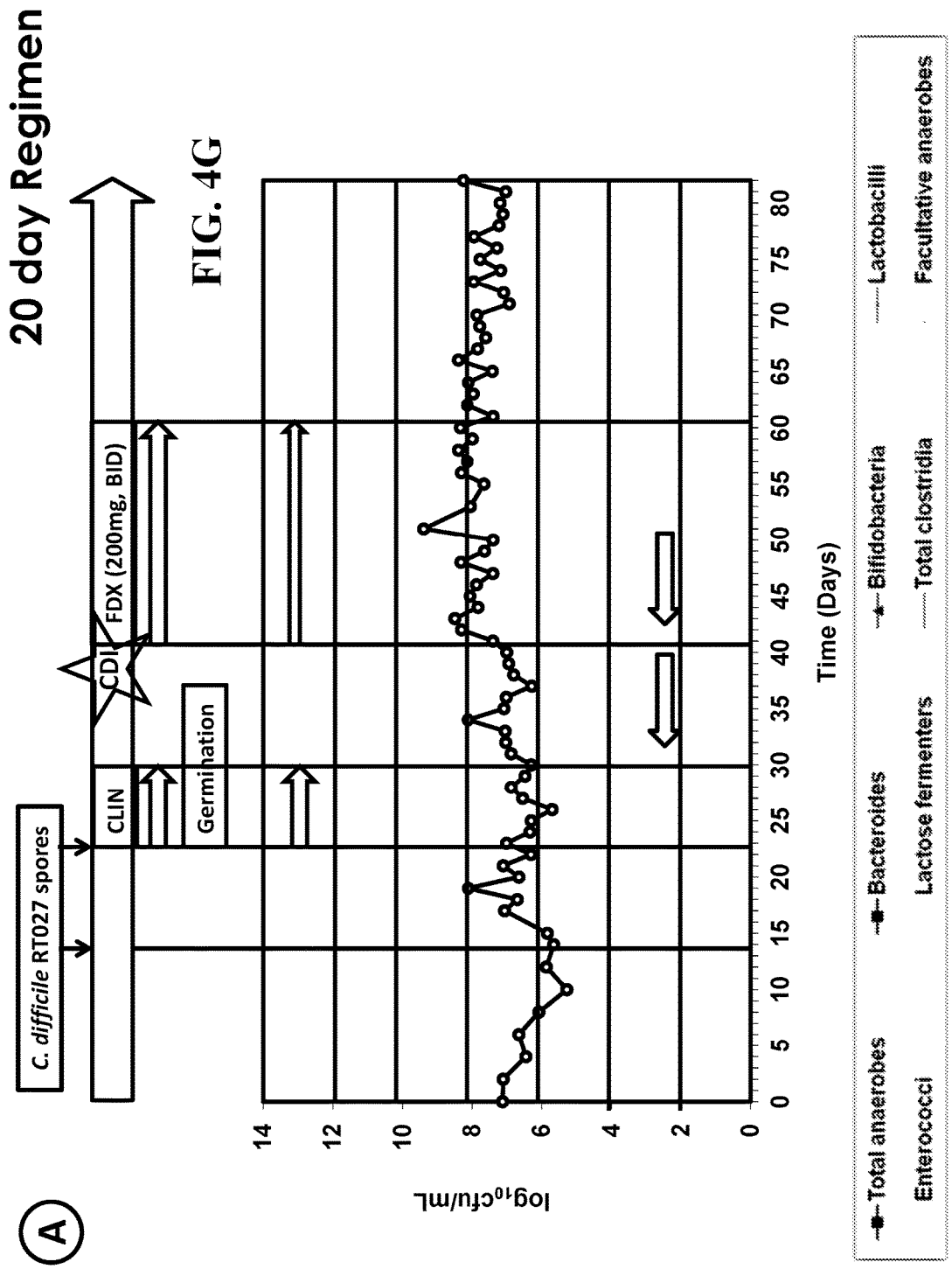
FIG. 4G provides a graphical representation of the Lactose fermenters level (circles) versus time in days for the reference example A.
Figure 4H:
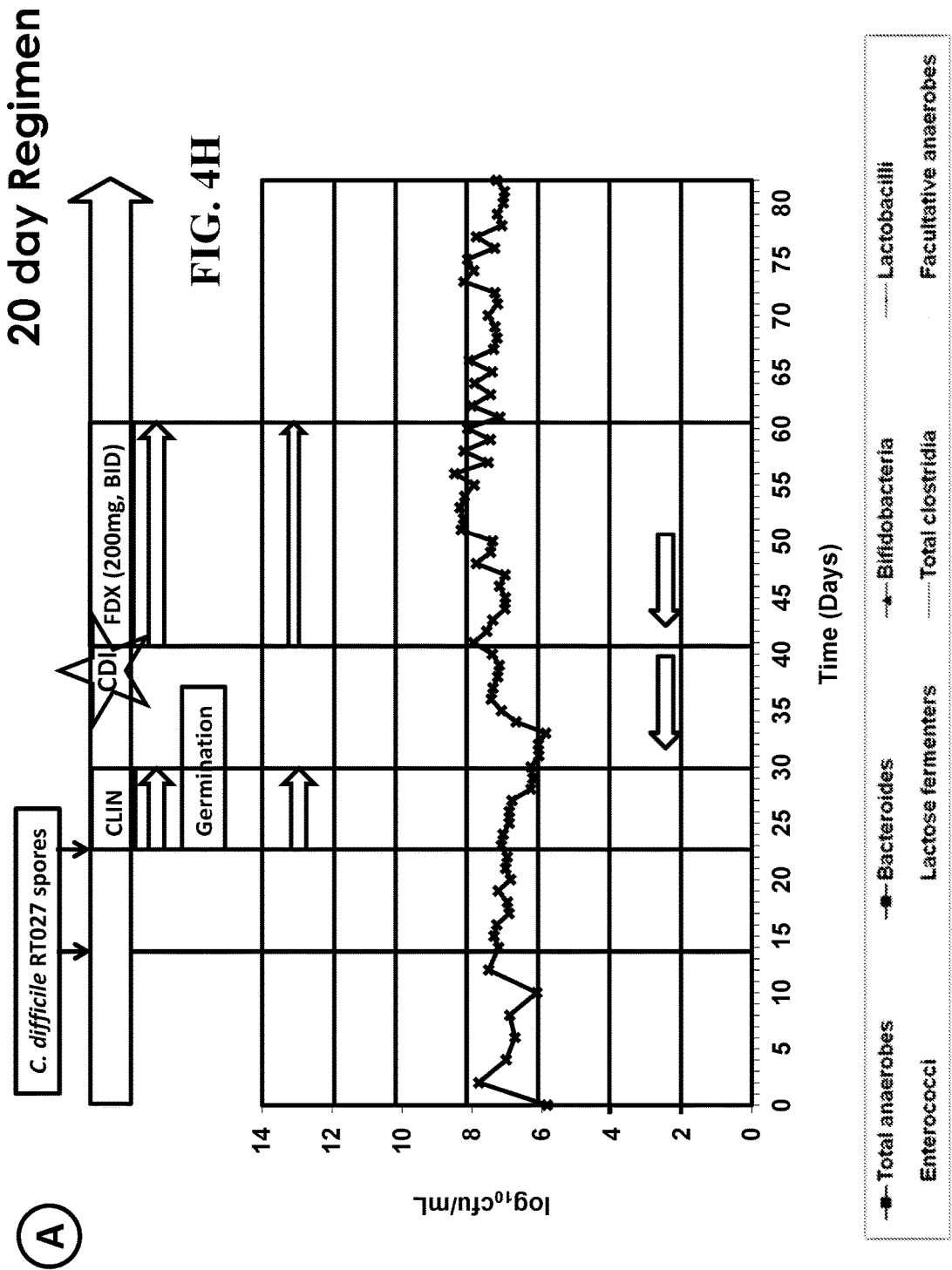
FIG. 4H provides a graphical representation of the total clostridia level (crosses) versus time in days for the reference example A.
Figure 5A:
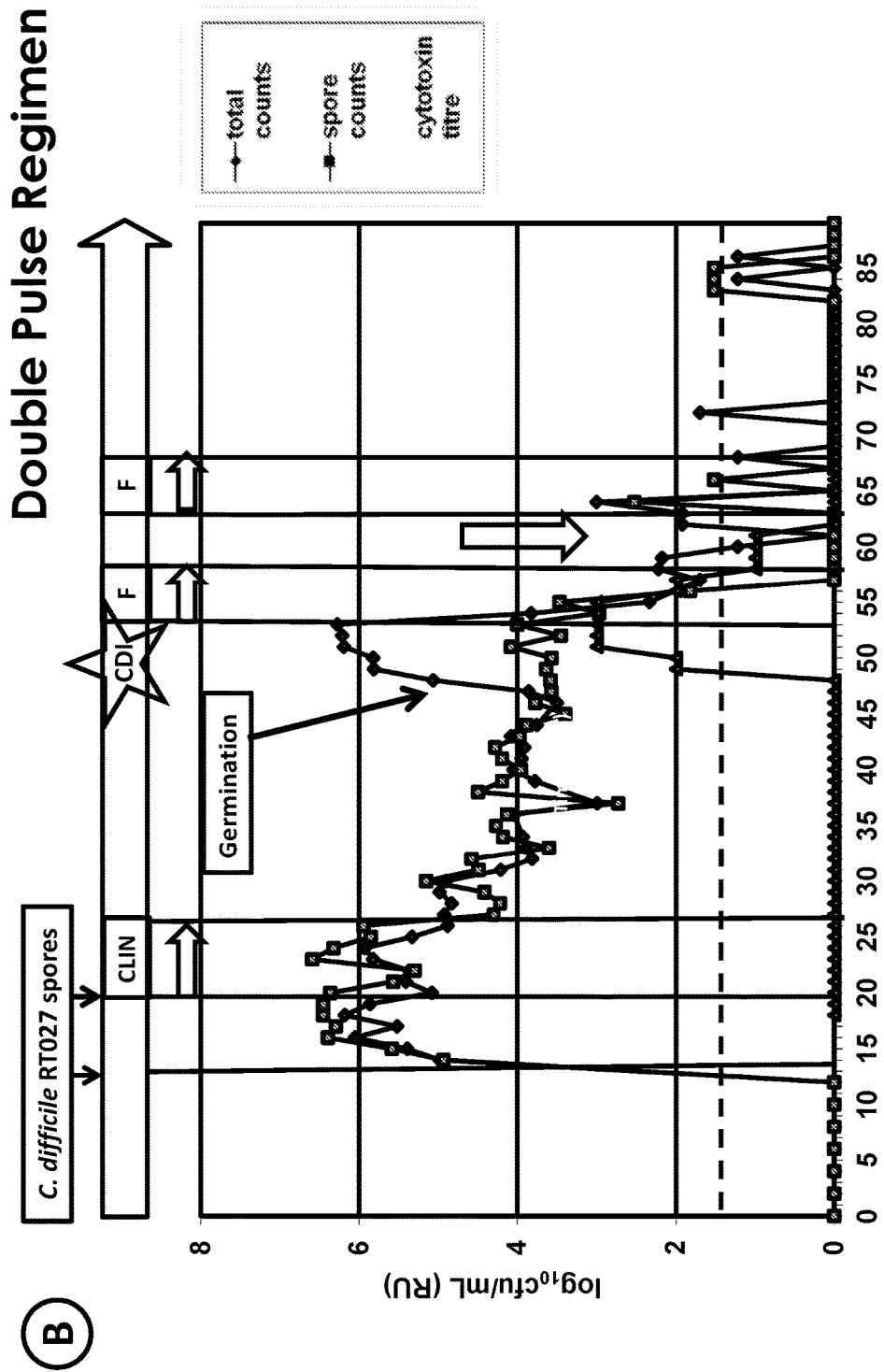
FIG. 5A provides a graphical representation of the total counts (diamonds/*rhombi*), spore counts (squares) and cytotoxin titre (triangles) versus time in days for the reference example B.
Figure 5B:
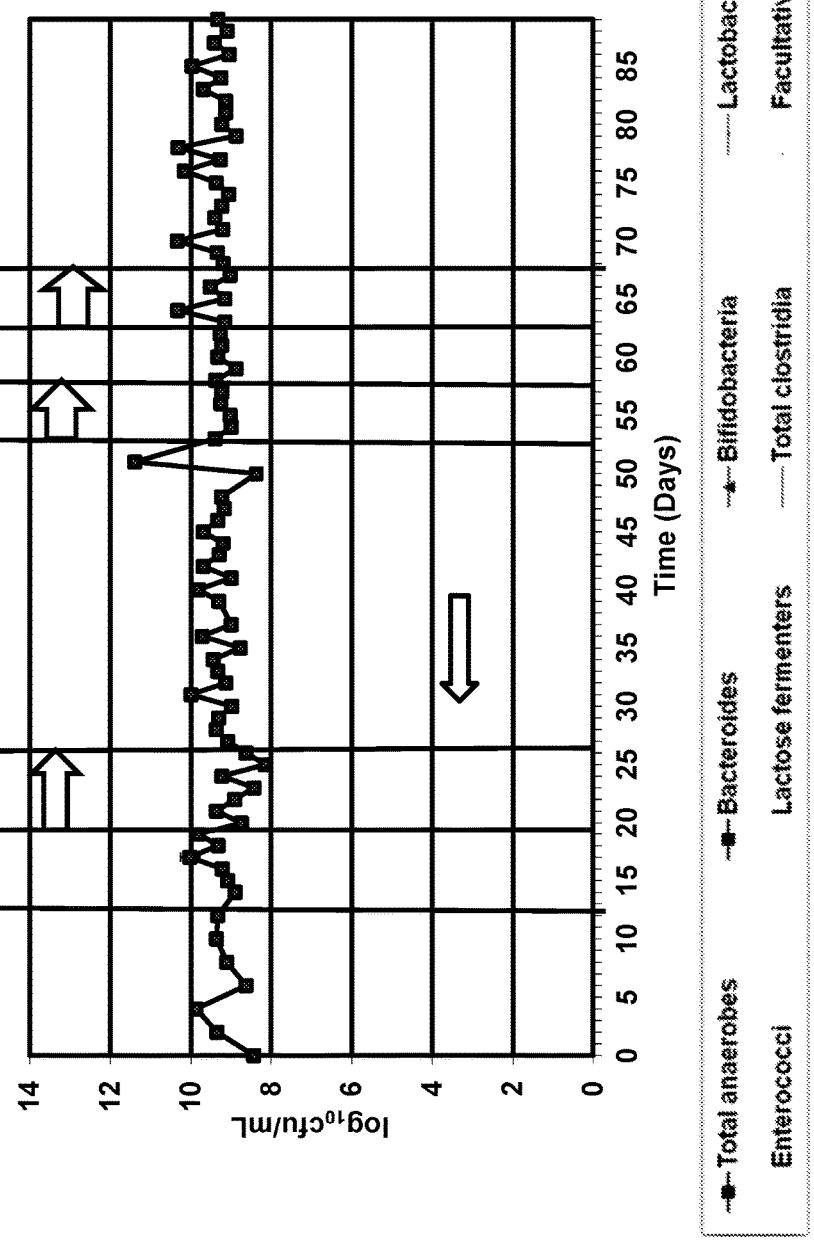
FIG. 5B provides a graphical representation of the total anaerobes level versus time in days for the reference example B.
Figure 5E:
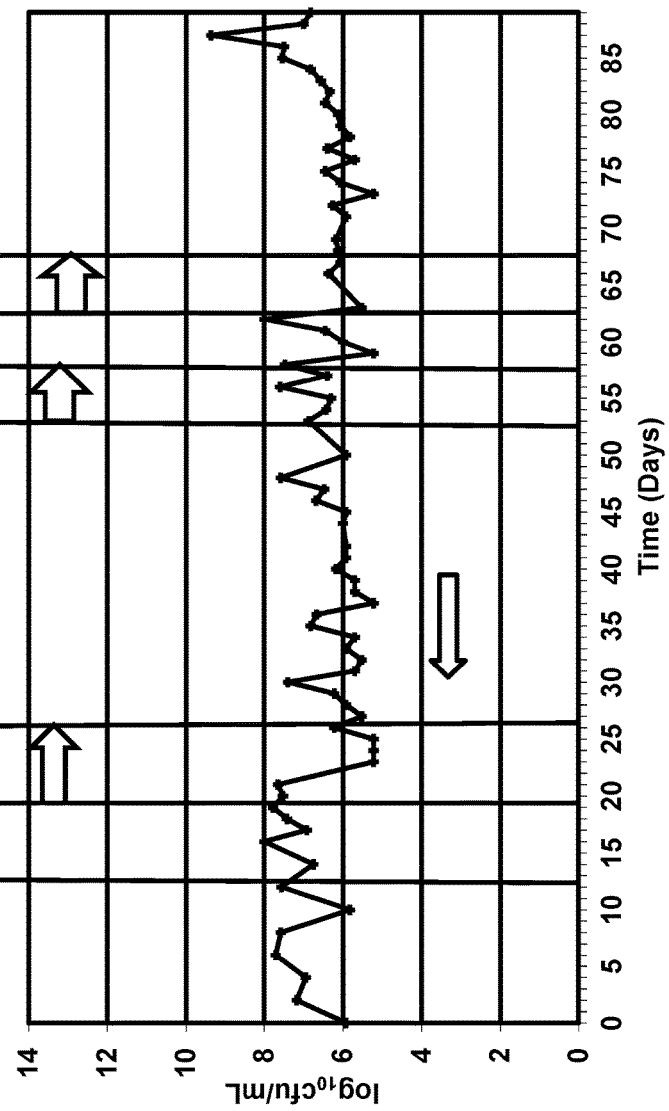
FIG. 5E provides a graphical representation of the Lactobacilli level versus time in days for the reference example B.
Figure 5G:
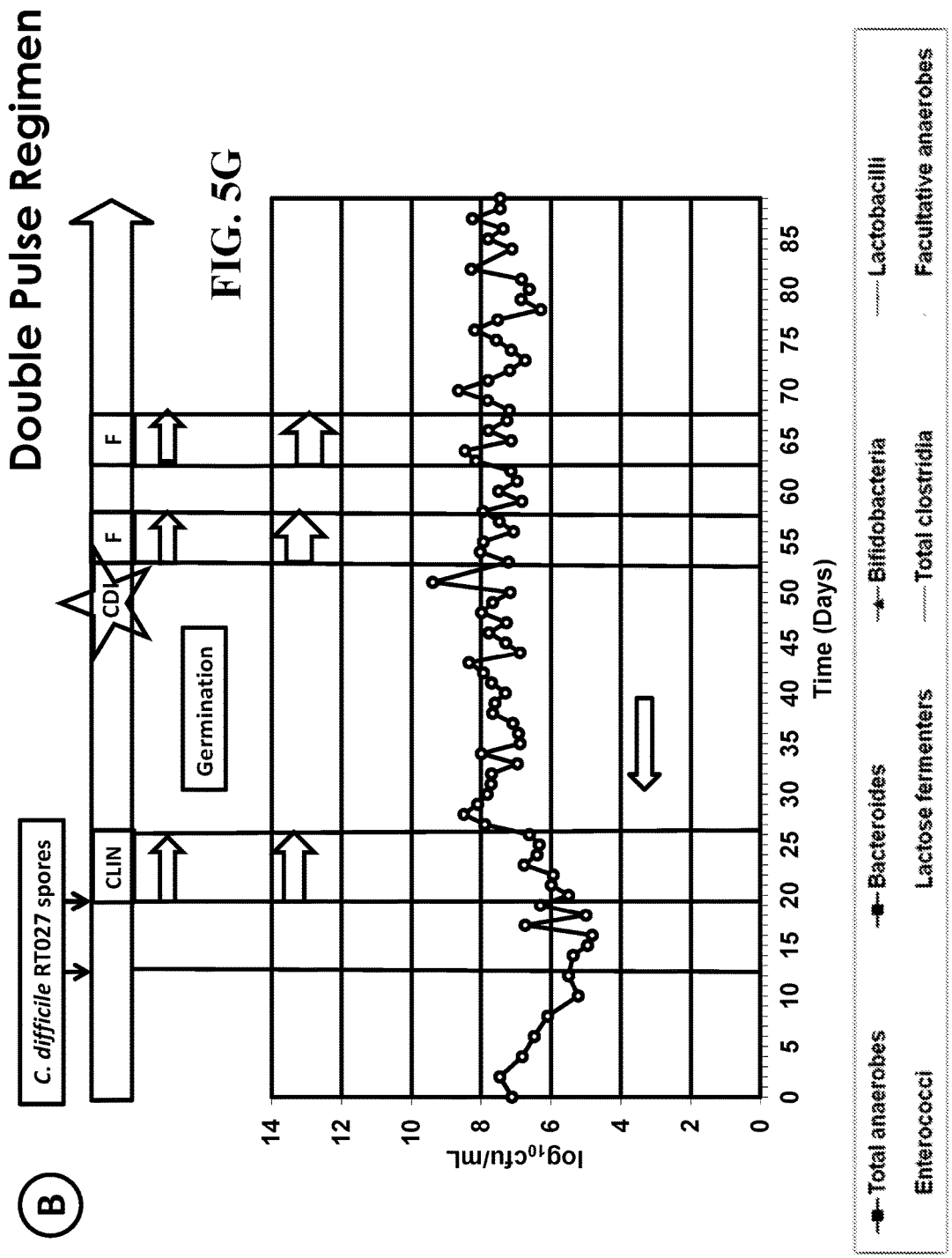
FIG. 5G provides a graphical representation of the Lactose fermenters level (circles) versus time in days for the reference example B.
Figure 5H:
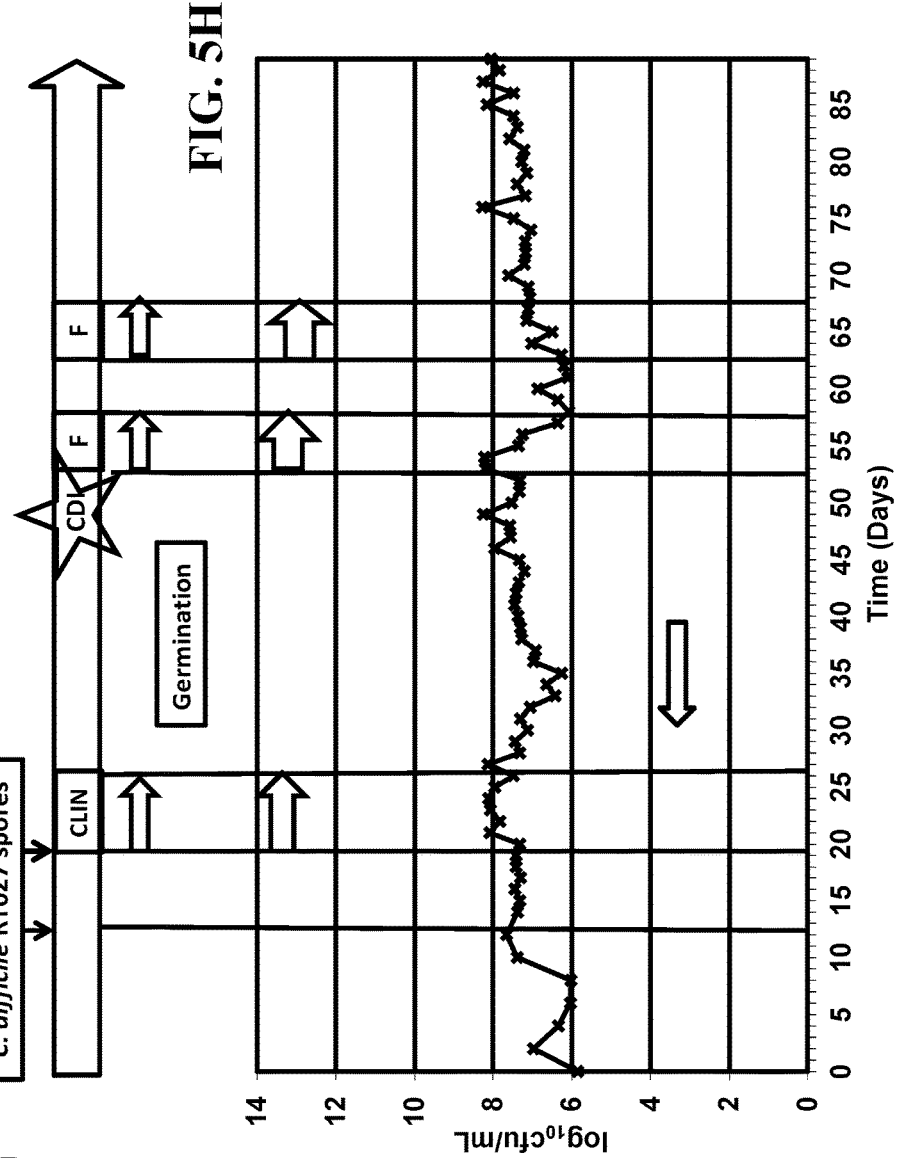
FIG. 5H provides a graphical representation of the total clostridia level (crosses) versus time in days for the reference example B.
Figure 6:
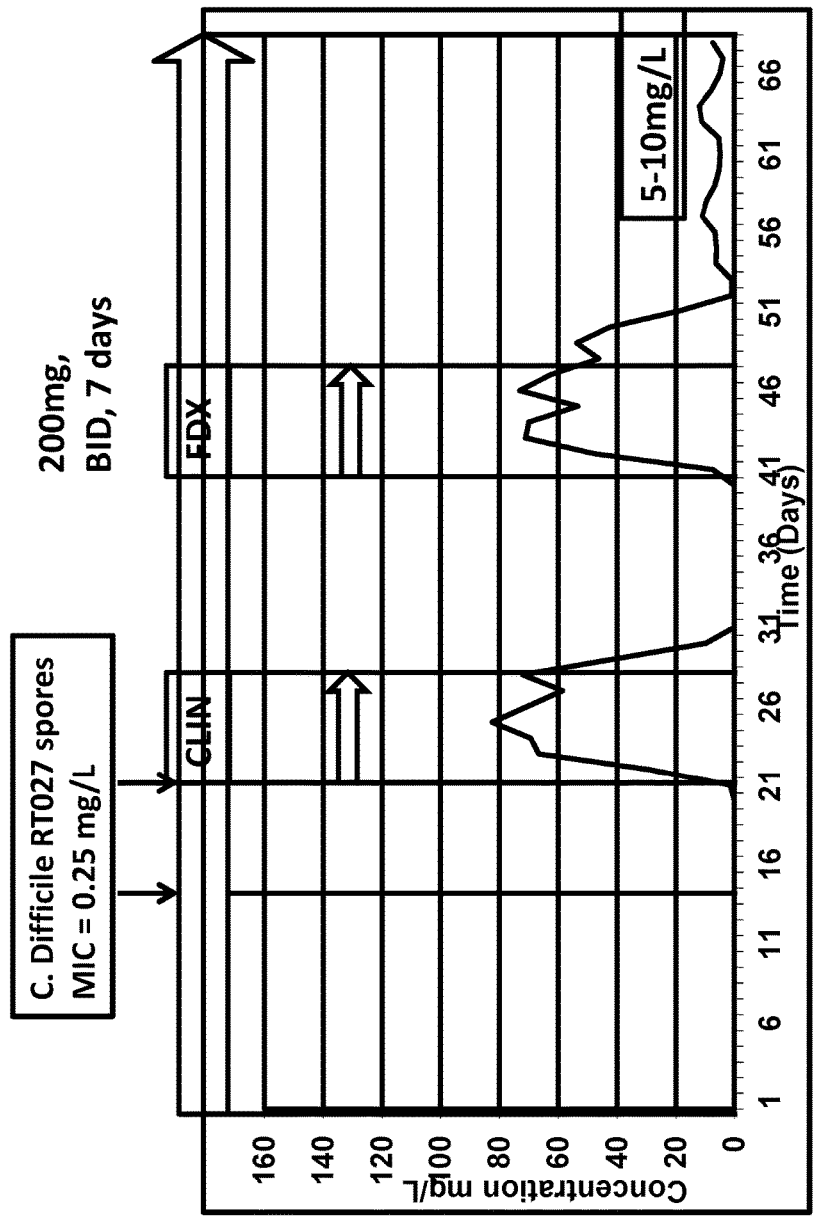
FIG. 6 provides a graphical representation of the antimicrobial concentrations achieved in the In Vitro Gut Model (IVGM) versus days (after 200 mg fidaxomicin BID for 7 days).
Figure 7A:
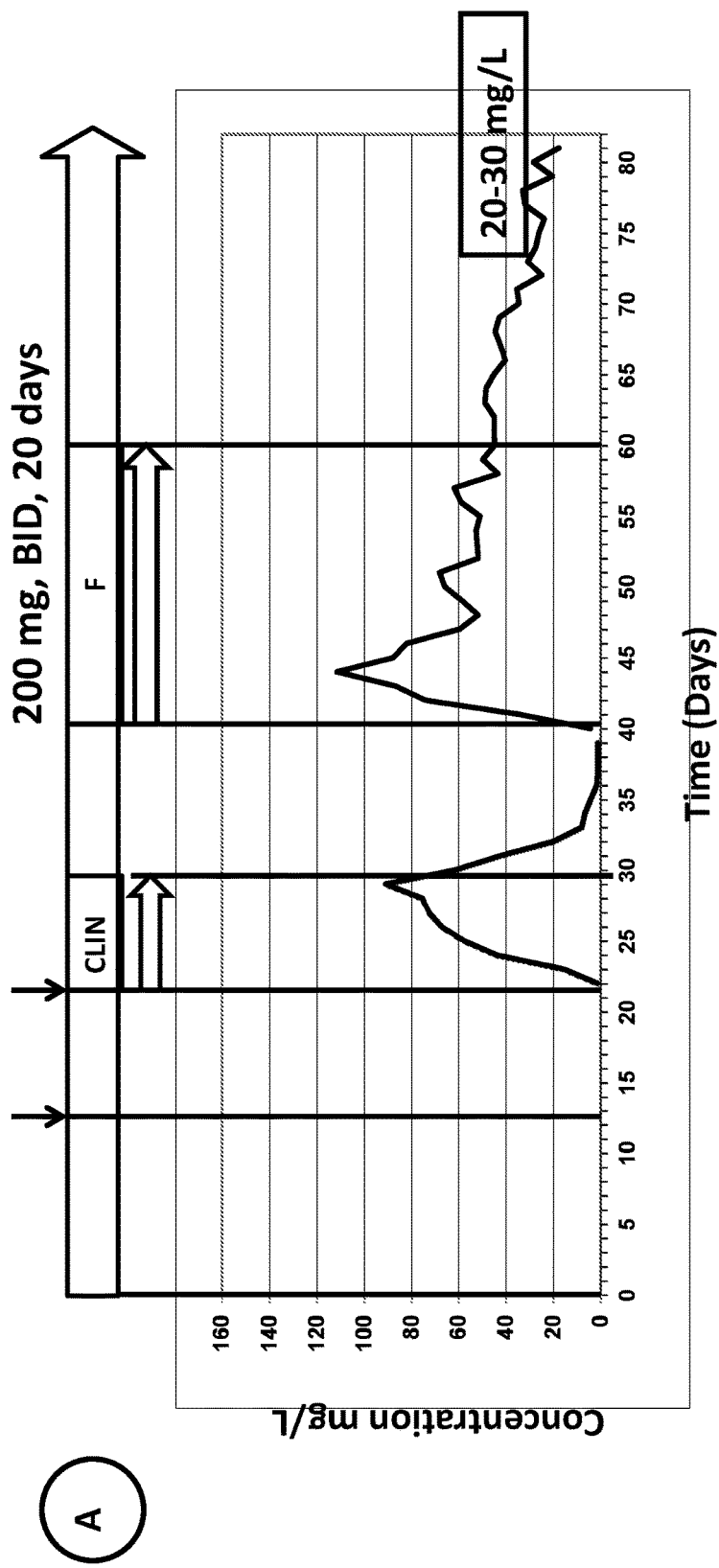
FIG. 7A provides a graphical representation of the antimicrobial concentrations achieved in IVGM versus days (after 200 mg fidaxomicin BID for 20 days).
Figure 7B:
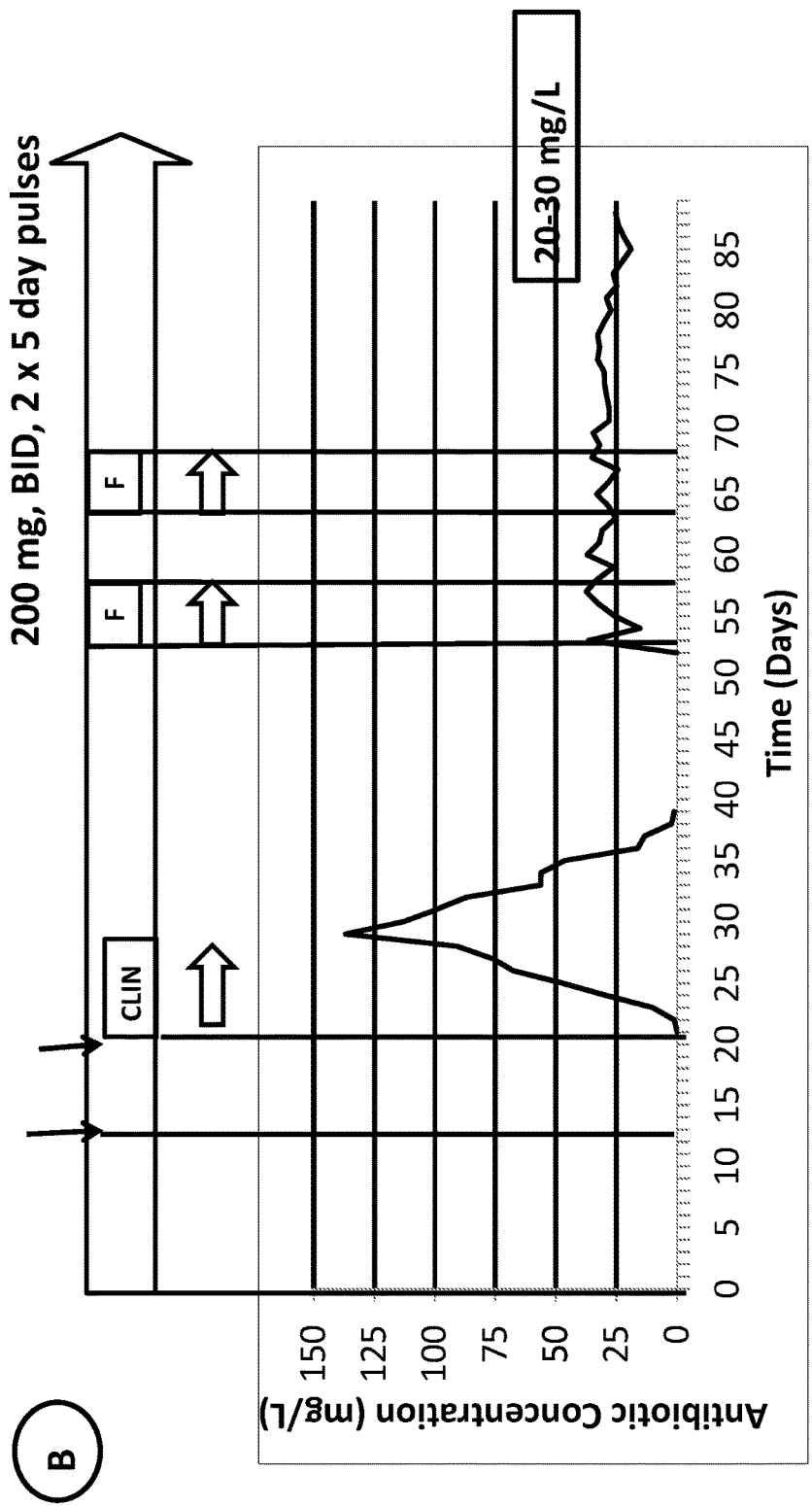
FIG. 7B provides a graphical representation of the antimicrobial concentrations achieved in IVGM versus days (after 200 mg fidaxomicin 2×5 days pulse).
Figure 8A:
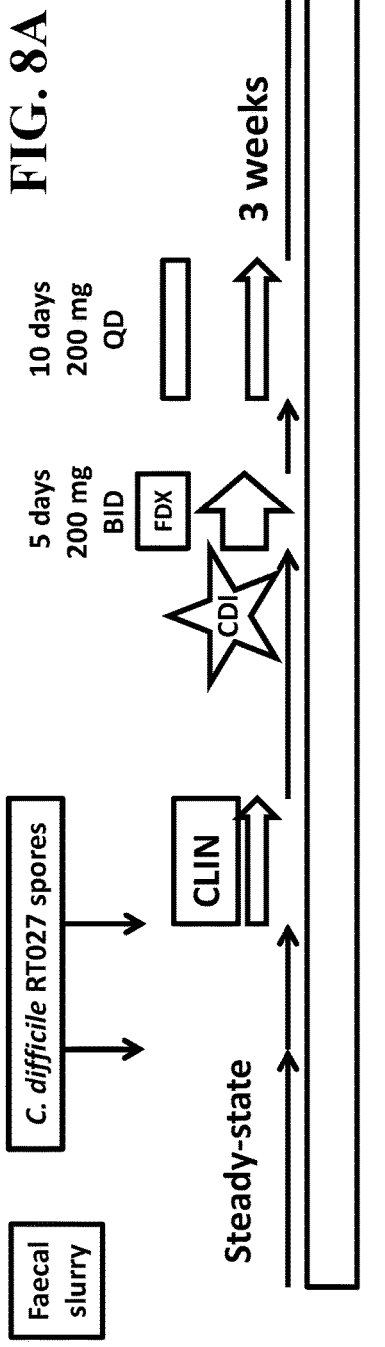
FIG. 8A provides the experimental design for the example 1 (C and D; treatment regimens i and ii).
Figure 8A:
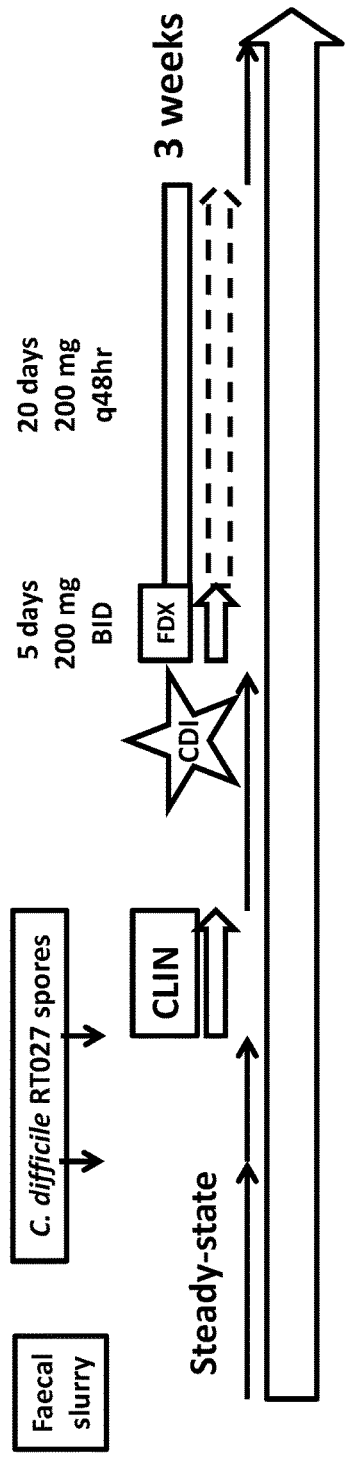
Figure 8B:
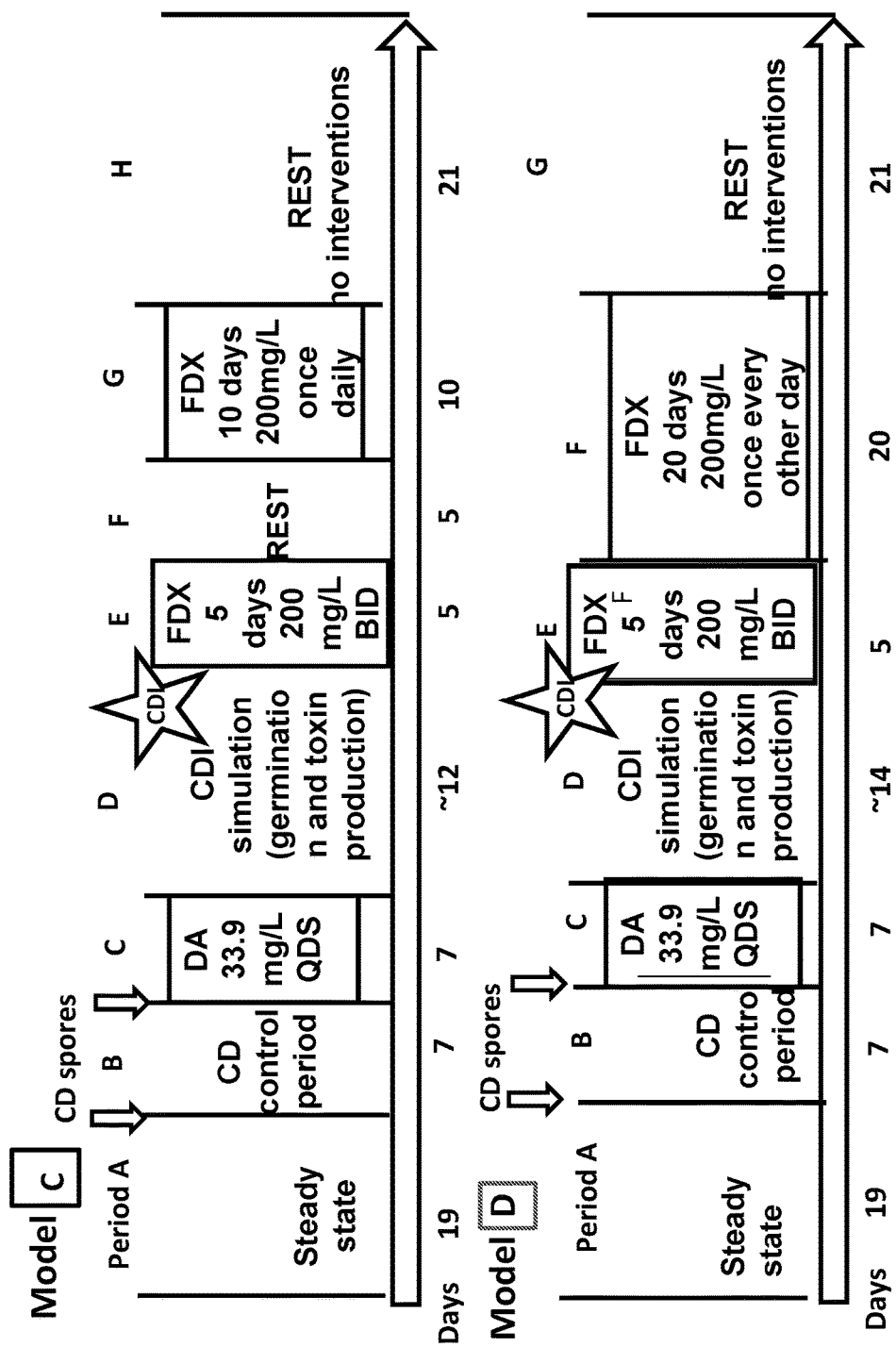
FIG. 8B provides an alternative representation of the experimental design for the example 1 (C and D; treatment regimens i and ii).
Figure 9A:
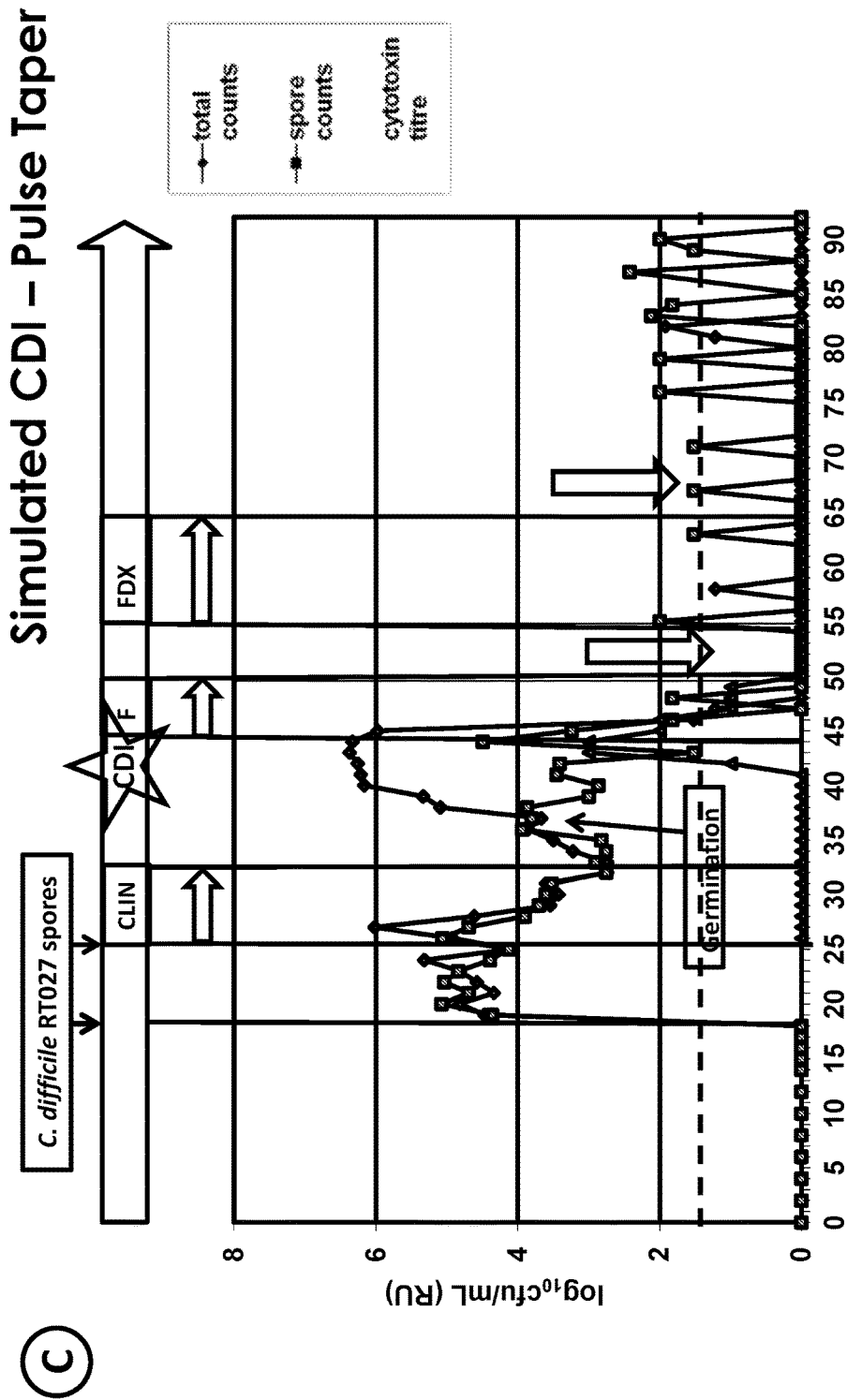
FIG. 9A provides a graphical representation of the total counts (diamonds/*rhombi*), spore counts (squares) and cytotoxin titre (triangles) versus time in days for the example C.
Figure 9B:
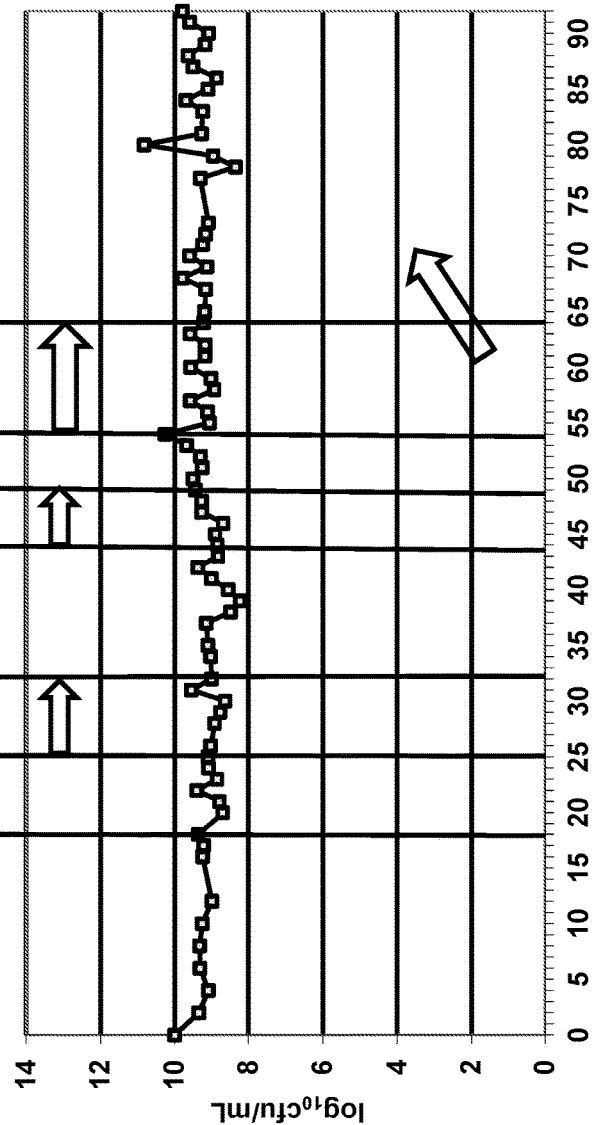
FIG. 9B provides a graphical representation of the total anaerobes level versus time in days for the example C.
Figure 9D:
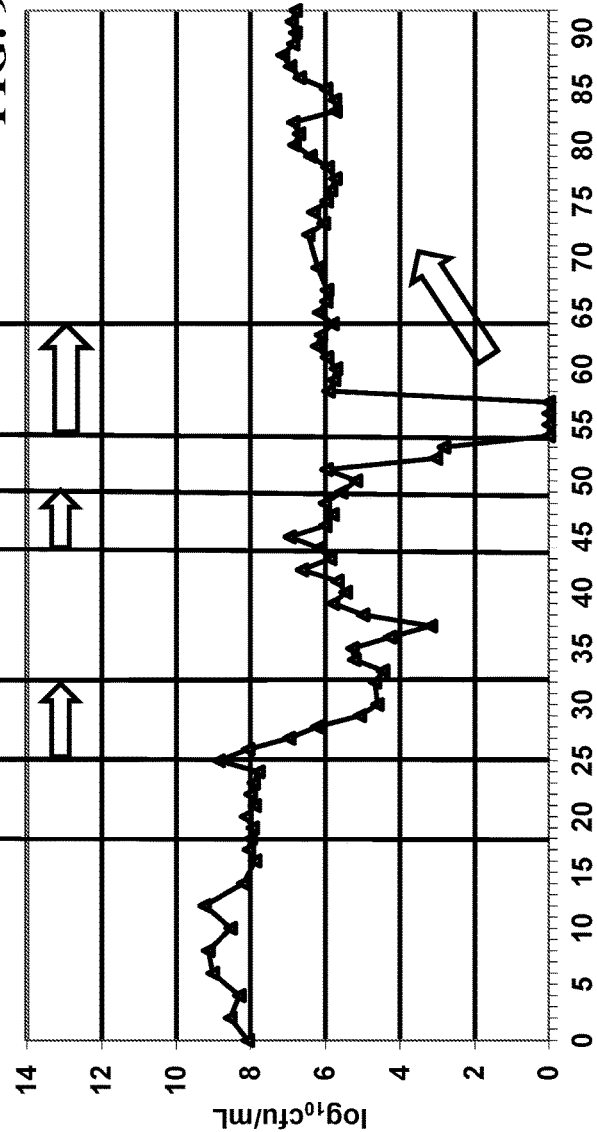
FIG. 9D provides a graphical representation of the Bifidobacteria level versus time in days for the example C.
Figure 9E:
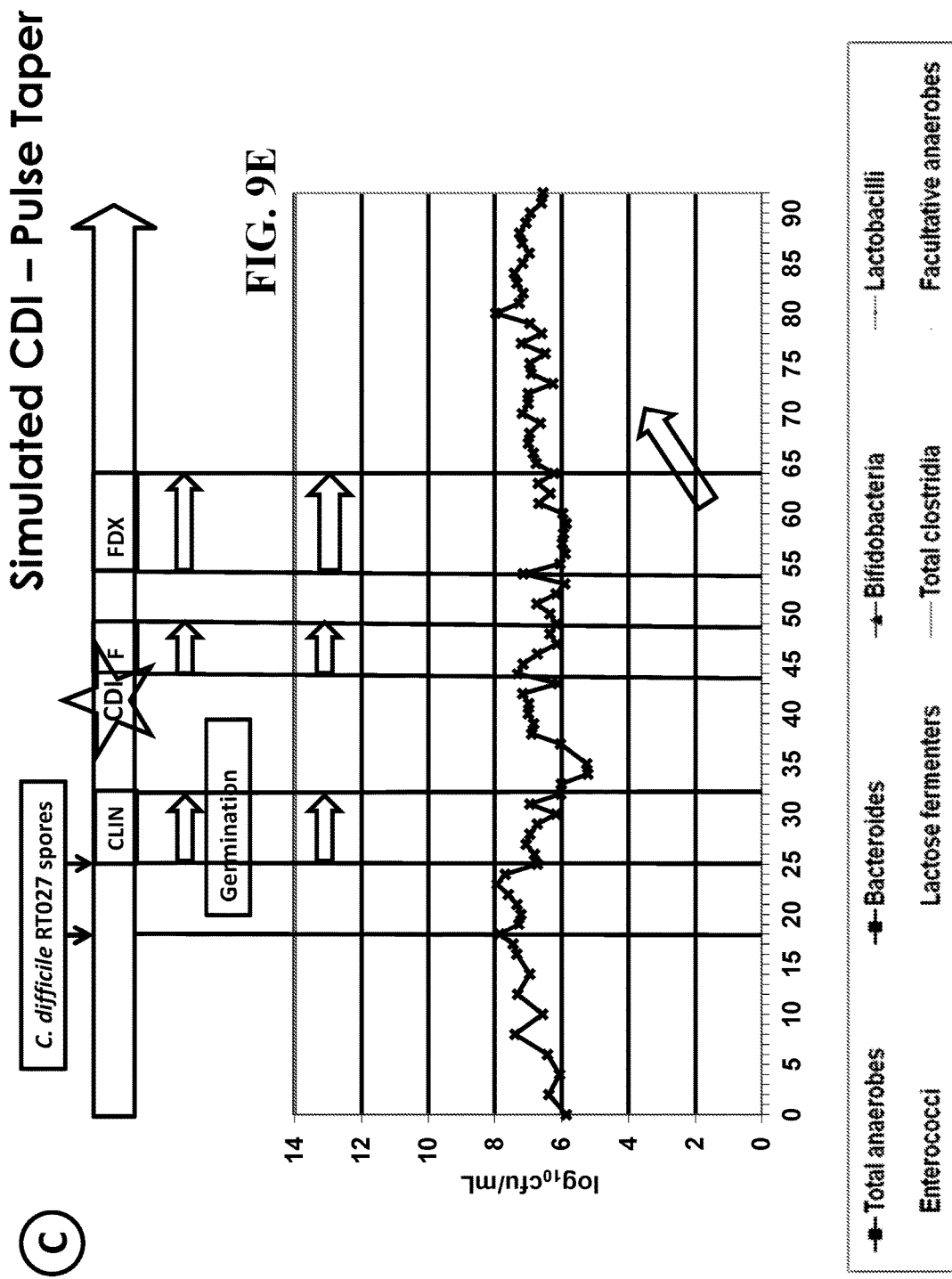
FIG. 9E provides a graphical representation of the Lactobacilli level versus time in days for the example C.
Figure 9F:
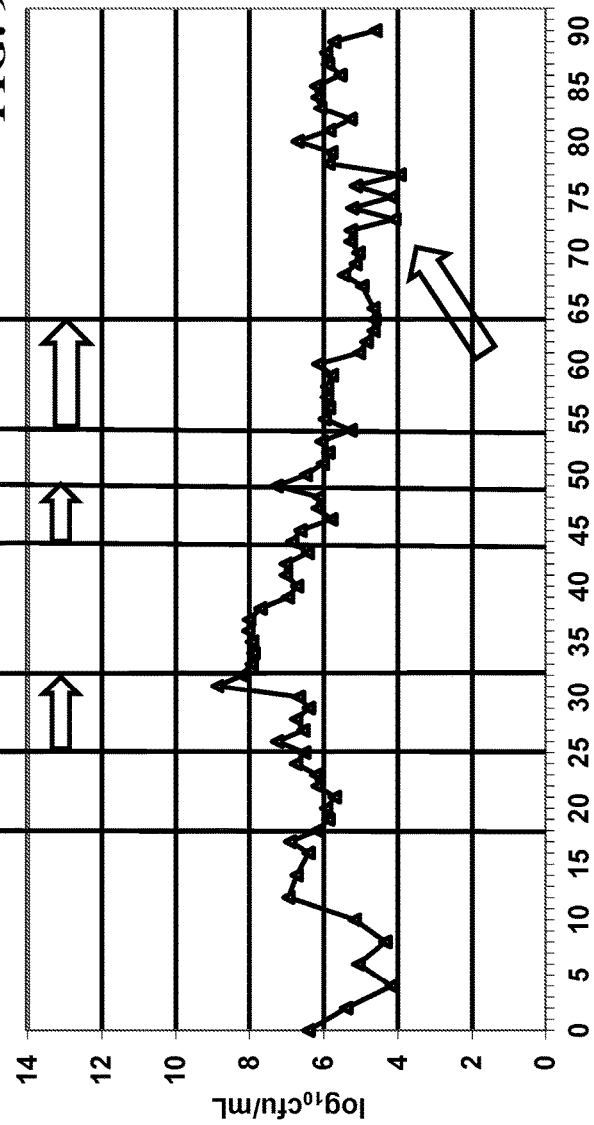
FIG. 9F provides a graphical representation of the Enterococci level (triangles) versus time in days for the example C.
Figure 9F:
Figure 9G:
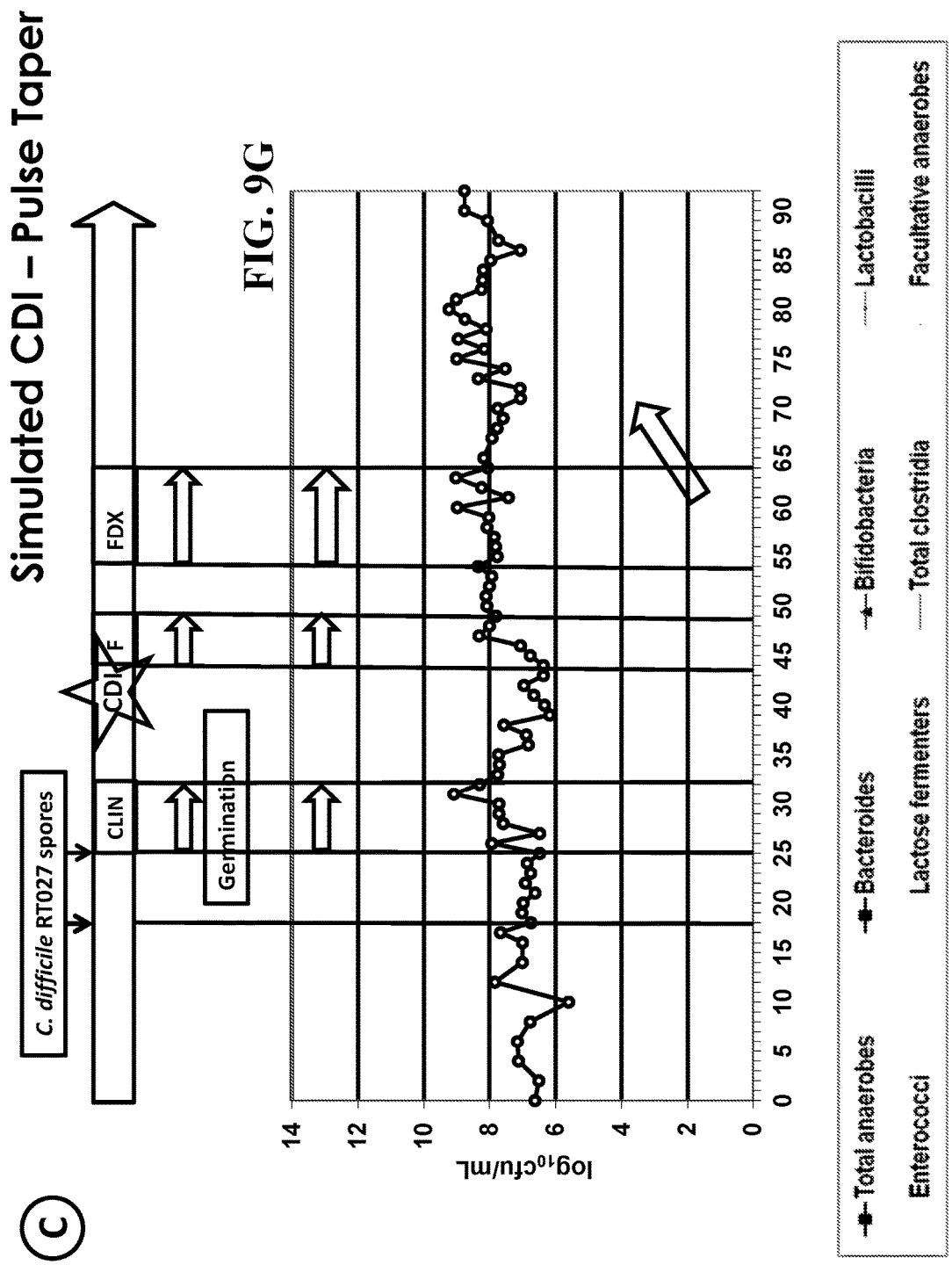
FIG. 9G provides a graphical representation of the Lactose fermenters level (circles) versus time in days for the example C.
Figure 9H:
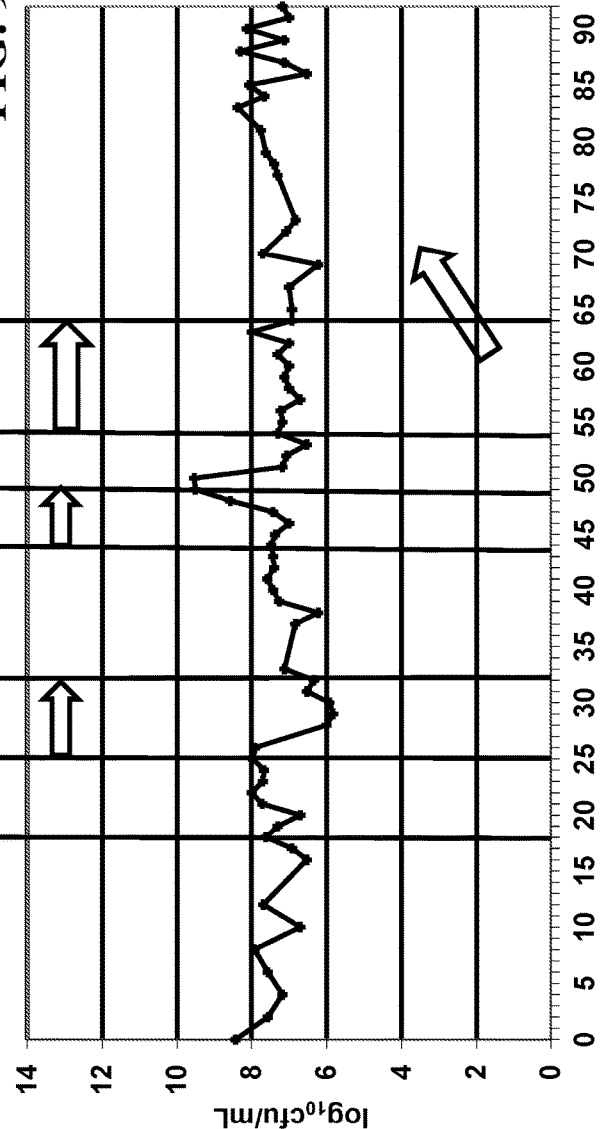
FIG. 9H provides a graphical representation of the total clostridia level (crosses) versus time in days for the example C.
Figure 10A:
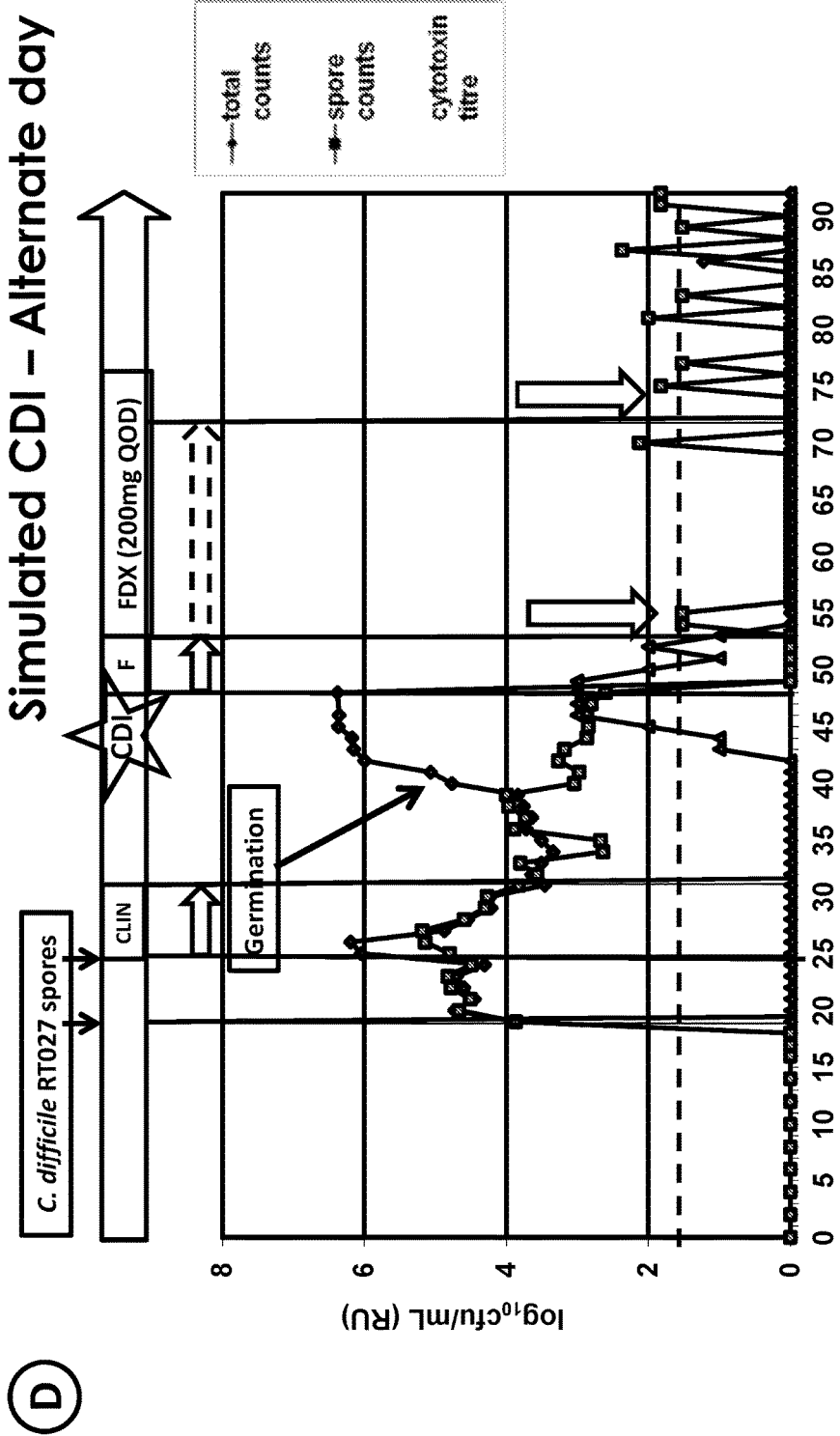
FIG. 10A provides a graphical representation of the total counts (diamonds/*rhombi*), spore counts (squares) and cytotoxin titre (triangles) versus time in days for the example D.
Figure 10B:
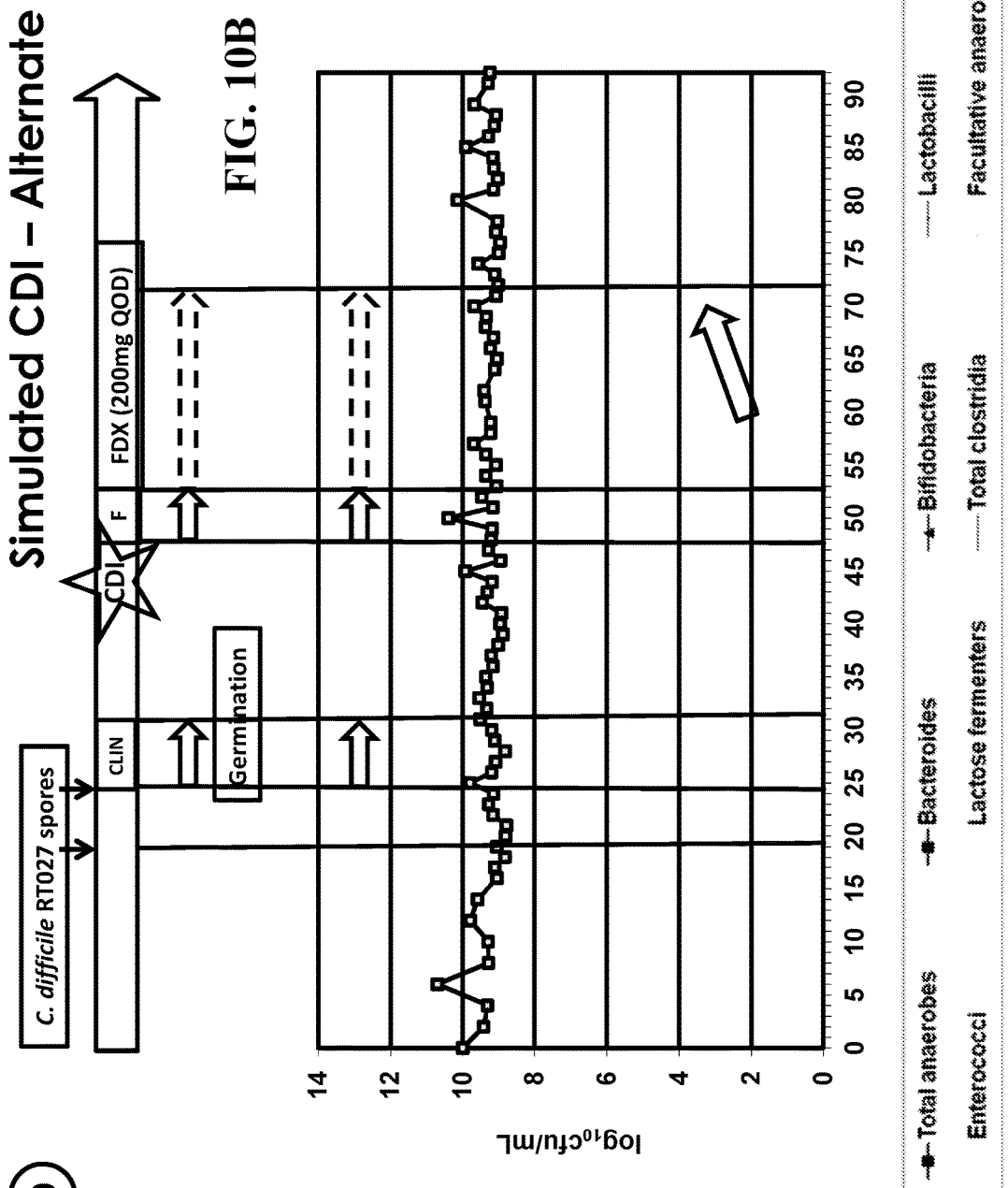
FIG. 10B provides a graphical representation of the total anaerobes level versus time in days for the example D.
Figure 10C:
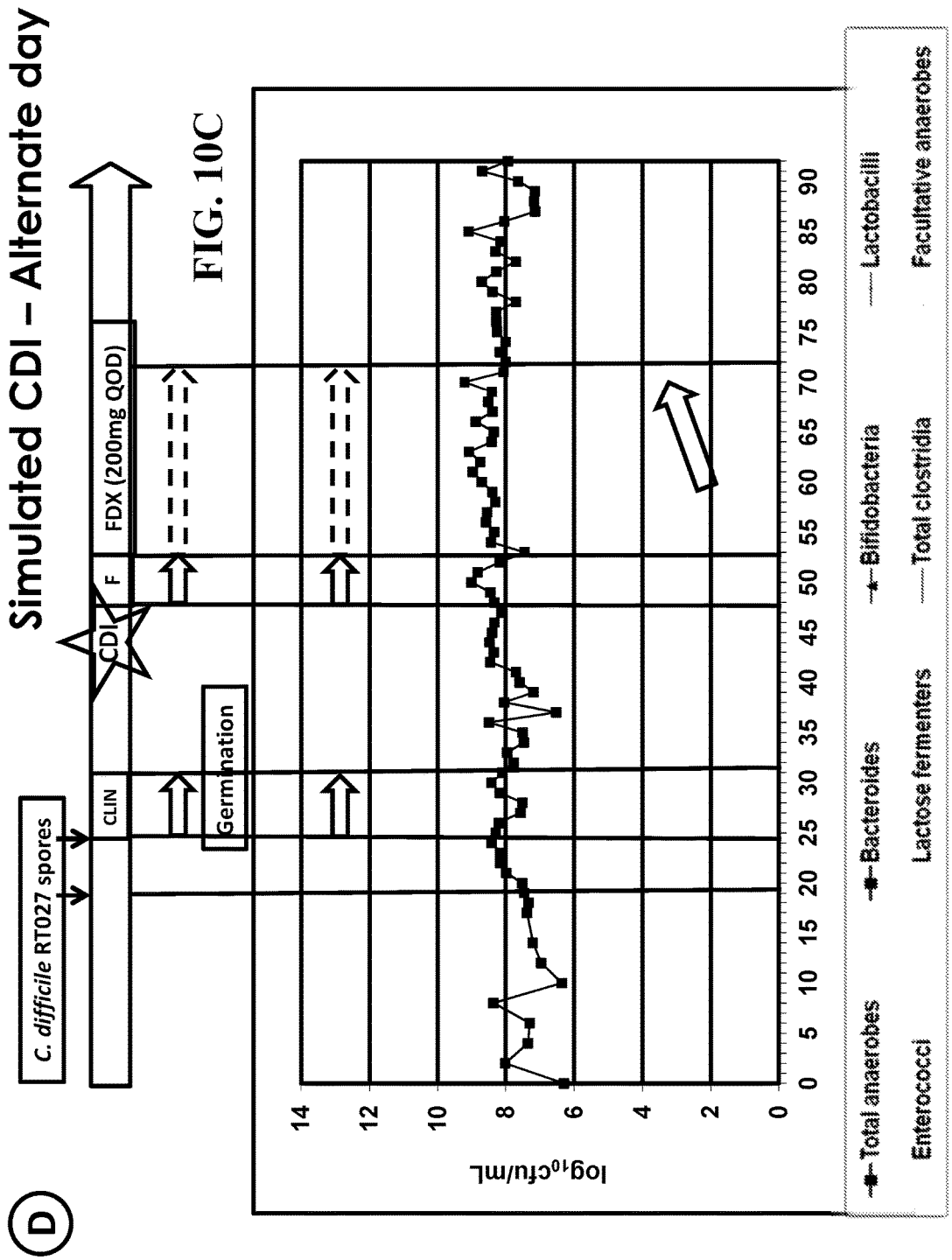
FIG. 10C provides a graphical representation of the *Bacteroides* level versus time in days for the example D.
Figure 10D:
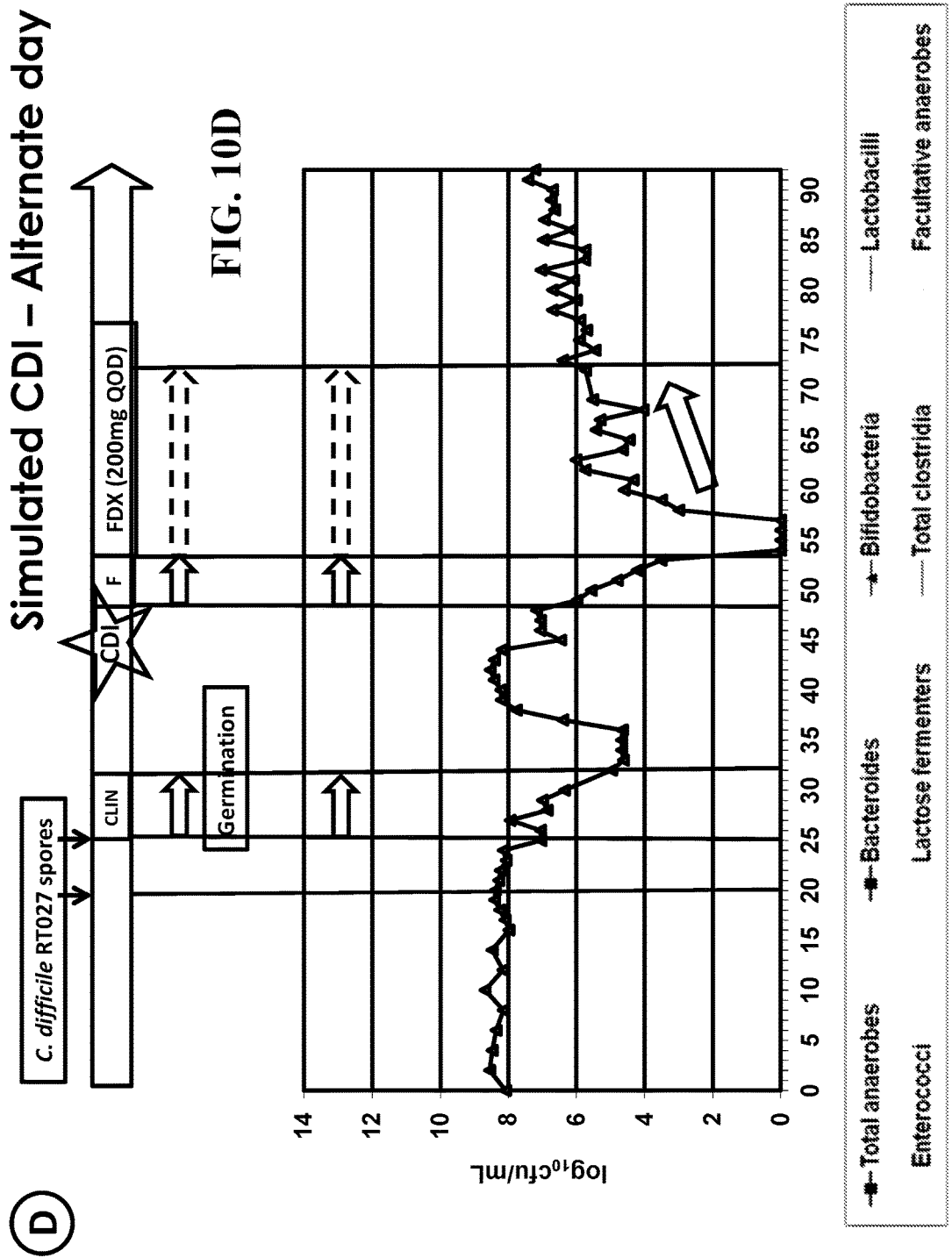
FIG. 10D provides a graphical representation of the Bifidobacteria level versus time in days for the example D.
Figure 10E:
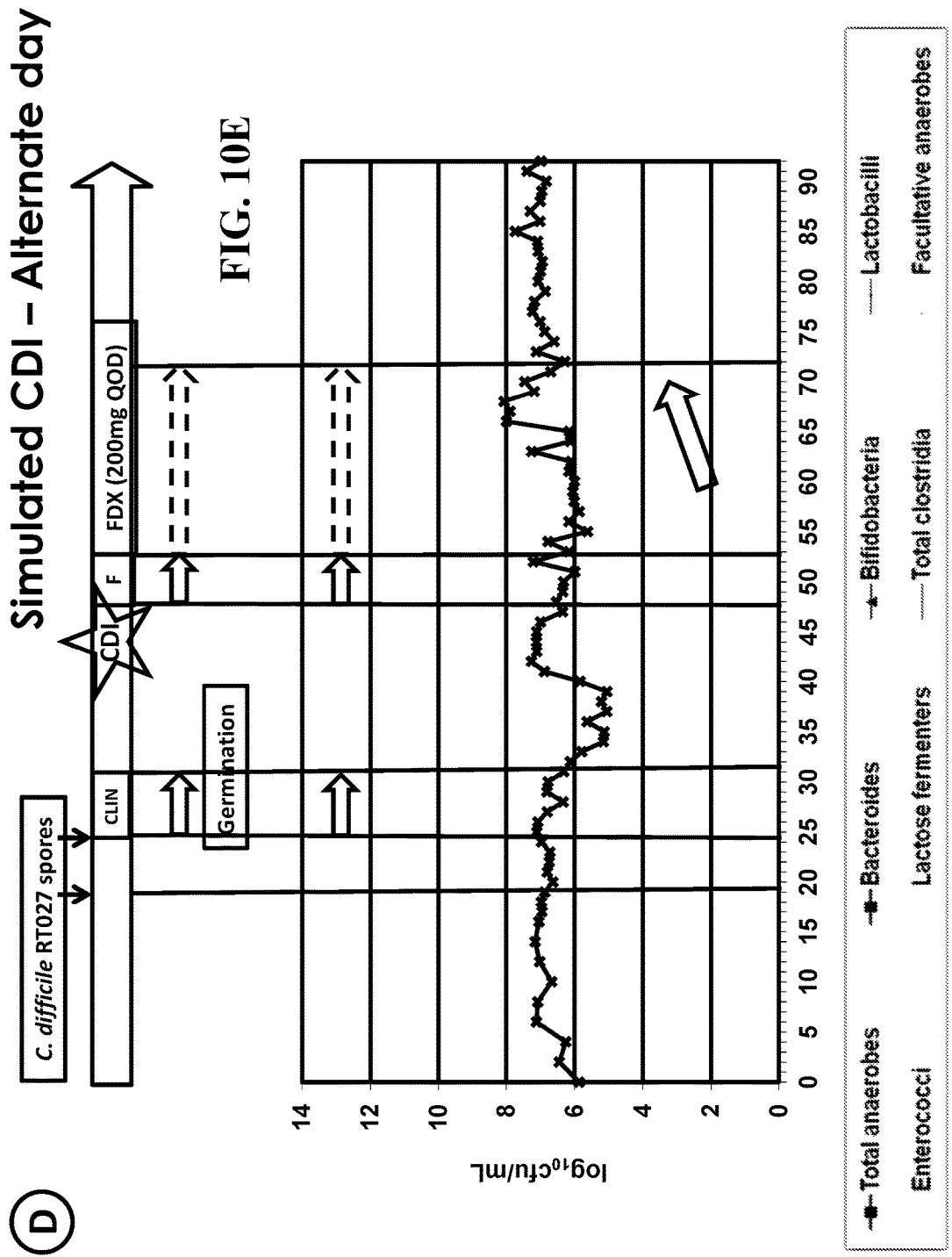
FIG. 10E provides a graphical representation of the Lactobacilli level versus time in days for the example D.
Figure 10F:
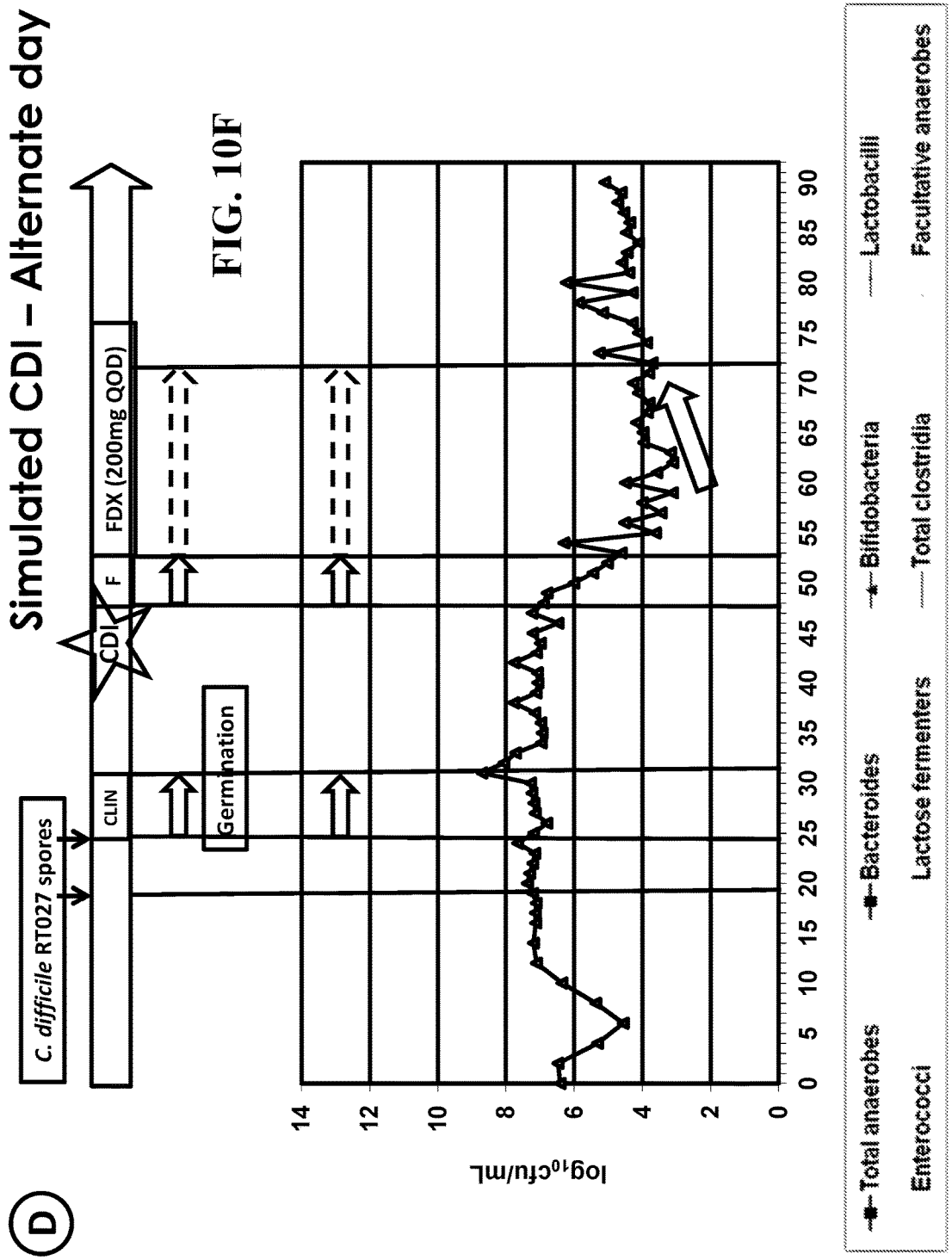
FIG. 10F provides a graphical representation of the Enterococci level (triangles) versus time in days for the example D.
Figure 10G:
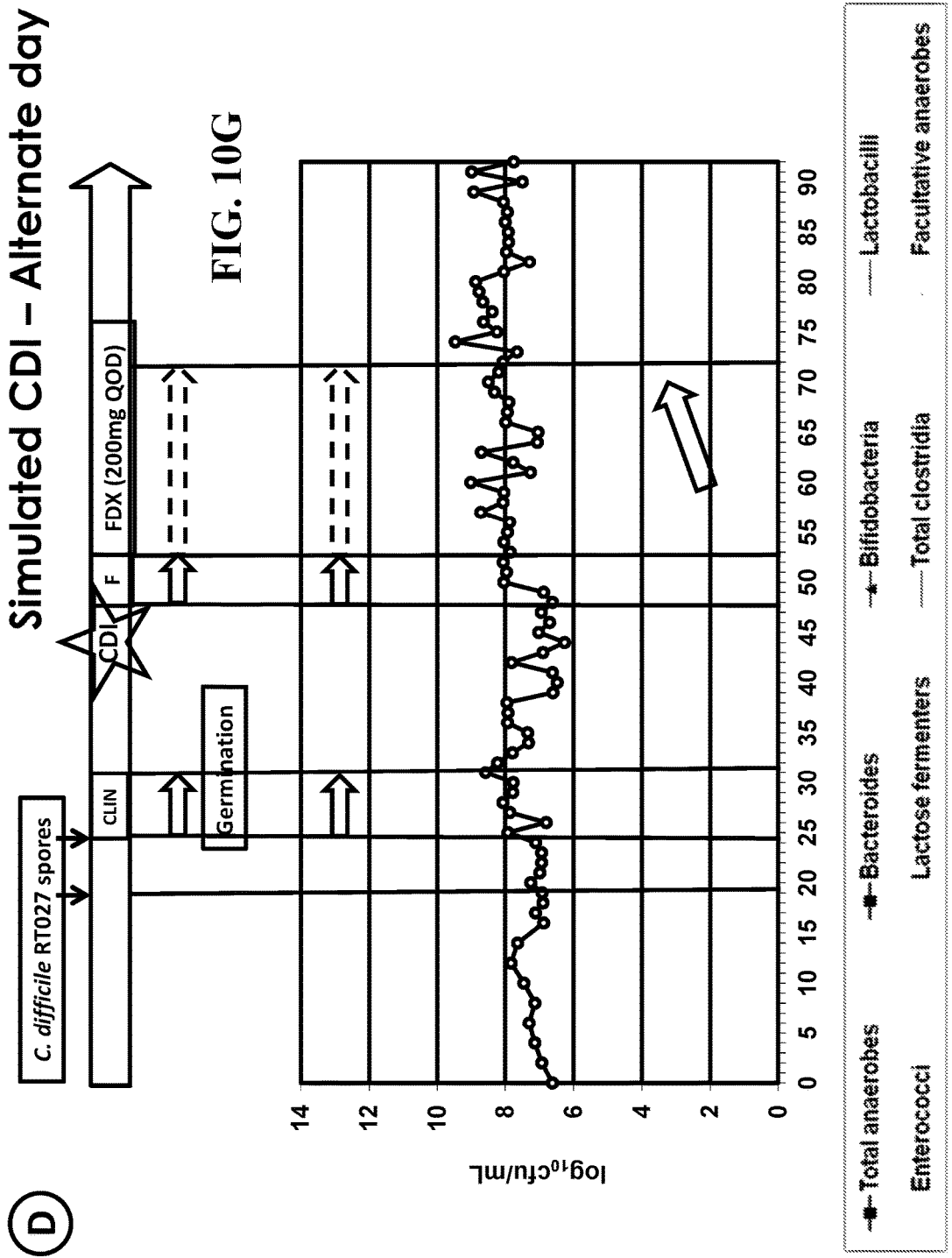
FIG. 10G provides a graphical representation of the Lactose fermenters level (circles) versus time in days for the example D.

The present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile* associated diarrhea or disease (CDAD) in an adult patient according to a dosage regimen, which is selected from the group consisting of:
 i. 200 mg of the tiacumicin compound BID for 5 days followed by 5 days of rest and then 200 mg once daily for a further 10 days and
 ii. 200 mg of the tiacumicin compound BID for 5 days followed by a single 200 mg every other day for 20 days.

In a first embodiment the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile* associated diarrhea or disease (CDAD) in a patient according to a dosage regimen which consists of administering 200 mg of the tiacumicin compound BID for 5 days followed by 5 days of rest and then 200 mg once daily for a further 10 days.

In a second embodiment the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile* associated diarrhea or disease (CDAD) in a patient according to a dosage regime which involves administering 200 mg of the tiacumicin compound BID for 5 days followed by a single 200 mg every other day for 20 days.

In a third embodiment the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile* associated diarrhea or disease (CDAD) in a patient according to a dosage regimen which consists of administering 200 mg of the tiacumicin compound BID for 5 days followed by 5 days of rest and then 200 mg once daily for a further 10 days, wherein the CDI is refractory CDI or recurrence CDI.

In a fourth embodiment the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile* associated diarrhea or disease (CDAD) in a patient according to a dosage regime which involves administering 200 mg of the tiacumicin compound BID for 5 days followed by a single 200 mg every other day for 20 days, wherein the CDI is refractory CDI or recurrence CDI.

The expression "stereo-isomer thereof" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity. The symbols "R" and "S" represent the configuration of substituents around a chiral carbon atom. The isomeric descriptors "R" and "S" are used as described herein for indicating atom configuration relative to a core molecule and are intended to be used as defined in the literature (IUPAC Recommendations 1996, Pure & Applied Chemistry 68: 2193-2222).

The expression "polymorph thereof" describes any alternative crystalline form having different physical properties as a result of the different order of the molecule in a crystal lattice. More specifically, polymorphs such as disclosed in WO2008/091554 are included.

The expression "pharmaceutically acceptable solvate thereof" describes any pharmaceutically acceptable solvate that, administered to a patient (directly or indirectly) provides a tiacumicin compound. Preferably, the solvate is a hydrate, a solvate with an alcohol such as methanol, ethanol, propanol, or isopropanol, a solvate with an ester such as ethyl acetate, a solvate with an ether such as methyl ether, ethyl ether or THF (tetrahydrofuran) or a solvate with DMF (dimethylformamide), of which a hydrate or a solvate with an alcohol such as ethanol is more preferred. A solvent for constituting the solvate is preferably a pharmaceutically acceptable solvent.

The tiacumicin compound according to the present invention, has an 18-membered macrocyclic glycoside structure and is a compound as disclosed in U.S. Pat. Nos. 4,918,174; 5,583,115; 5,767,096; and in Chinese patent applications 201010526416.9 and 201110104051.5, herein incorporated by reference. Preferably, the active ingredient is selected from the group consisting of tiacumicin A, tiacumicin B and analogues thereof, (dialkyltiacumicins and bromotiacumicins), tiacumicin C, tiacumicin D, tiacumicin E, tiacumicin F and lipiarmycin. Though all tiacumicin compounds have in common that they are insoluble or almost insoluble in water, more preferably, the active ingredient is lipiarmycin or tiacumicin B or a stereo-isomer thereof or a polymorph thereof. Most preferably R-tiacumicin B (also known as fidaxomicin, OPT-80, or PAR-101) is used as the active ingredient.

In a further embodiment the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile* associated diarrhea or disease (CDAD) in a patient according to a dosage regimen which consists of administering 200 mg of the tiacumicin compound BID for 5 days followed by 5 days of rest and then 200 mg once daily for a further 10 days, wherein the tiacumicin compound is fidaxomicin.

In yet a further embodiment the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile* associated diarrhea or disease (CDAD) in a patient according to a dosage regimen which consists of administering 200 mg of the tiacumicin compound BID for 5 days followed by a single 200 mg every other day for 20 days, whereby the tiacumicin compound is fidaxomicin.

In yet a further embodiment the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile* associated diarrhea or disease (CDAD) in a patient according to a dosage regimen which consists of administering 200 mg of the tiacumicin compound BID for 5 days followed by 5 days of rest and then 200 mg once daily for a further 10 days, wherein the CDI is refractory CDI or recurrence CDI and whereby the tiacumicin compound is fidaxomicin.

In yet a further embodiment the present invention relates to a tiacumicin compound, a stereo-isomer thereof, a polymorph thereof or a pharmaceutically acceptable solvate thereof for use in the oral treatment of *Clostridium difficile* infections (CDI) or *Clostridium difficile* associated diarrhea or disease (CDAD) in a patient according to a dosage regime which involves administering 200 mg of the tiacumicin compound BID for 5 days followed by a single 200 mg every other day for 20 days, wherein the CDI is refractory CDI or recurrence CDI and whereby the tiacumicin compound is fidaxomicin.

A further embodiment is a pharmaceutical composition, comprising a tiacumicin compound, a stereo-isomer thereof, a polymorph thereof or a pharmaceutically acceptable solvate thereof, for use in the oral treatment of *Clostridium difficile* infections (CDI) or *Clostridium difficile* associated diarrhea or disease (CDAD) in a patient according to a dosage regimen selected from the group consisting of:
i. Administering 200 mg of the tiacumicin compound BID for 5 days followed by 5 days of rest and then 200 mg once daily for a further 10 days and
ii. Administering 200 mg of the tiacumicin compound BID for 5 days followed by a single 200 mg every other day for 20 days.

Yet another embodiment relates to a pharmaceutical composition, comprising a tiacumicin compound, a stereo-isomer thereof, a polymorph thereof or a pharmaceutically acceptable solvate thereof, for use in the oral treatment of *Clostridium difficile* infections (CDI) or *Clostridium difficile* associated diarrhea or disease (CDAD) in a patient according to a dosage regimen selected from the group consisting of:
i. Administering 200 mg of the tiacumicin compound BID for 5 days followed by 5 days of rest and then 200 mg once daily for a further 10 days and
ii. Administering 200 mg of the tiacumicin compound BID for 5 days followed by a single 200 mg every other day for 20 days
wherein the tiacumicin compound is fidaxomicin.

And yet another embodiment relates to a pharmaceutical composition, comprising a tiacumicin compound, a stereo-isomer thereof, a polymorph thereof or a pharmaceutically acceptable solvate thereof, for use in the oral treatment of *Clostridium difficile* infections (CDI) or *Clostridium difficile* associated diarrhea or disease (CDAD) in a patient according to a dosage regimen selected from the group consisting of:
i. Administering 200 mg of the tiacumicin compound BID for 5 days followed by 5 days of rest and then 200 mg once daily for a further 10 days and
ii. Administering 200 mg of the tiacumicin compound BID for 5 days followed by a single 200 mg every other day for 20 days wherein the tiacumicin compound is fidaxomicin and is administered in a film-coated tablet.

The compositions to be used in the dosage regimen according to the invention may be an aqueous suspension, a dry powder for an aqueous suspension, a dry granulate for an aqueous suspension or a dispersible tablet, a capsule, a tablet, optionally film-coated. A preferred composition for oral administration is a tablet, in particular a film-coated tablet. A further preferred composition is an aqueous suspension. The aqueous suspension can be administered as such or prepared by adding a sufficient amount of water to a dry powder for an aqueous suspension, a dry granulate for an aqueous suspension or a dispersible tablet.

The term tablet also comprises fast-disintegrating tablets, amongst which are dispersible tablets and effervescent tablets.

The most commonly used methods of tablet preparation are direct compression, dry granulation and wet granulation. Direct compression involves compressing a mixture containing the active ingredient(s) and the excipient(s) on a tablet press (L. Lachman et al., in: The Theory and Practice of Industrial Pharmacy, 3rd ed., 1986). The mixture to be compressed must possess both good flow and compression properties in order to produce tablets having a uniform content of the active ingredient(s). Good flow properties cannot always be achieved by adding appropriate excipients, such as lubricants, anti-adhesive agents and flow-promoters to the mixture. Hence frequently the mixture is granulated prior to compression.

Granulation is a process by which sphere-like or regularly shaped aggregates called granules are formed out of the powder mixture. This can be achieved by dry granulation methods and wet granulation methods. Granulation is also used for converting a mixture of powders with poor cohesion into aggregates, which when compressed result in tablets that have good cohesion properties.

In the case of fast-disintegrating tablets, the active ingredient(s), optionally in admixture with one or more excipients, is (are) advantageously provided with a coating in order to mask the taste of such ingredient(s) and/or to protect the same against possible harmful effects by light and/or moisture and in the case of bendamustine to protect the mucosa in the mouth against the harmful effects exerted by the active compound. For that purpose a granulate preferably is prepared and processed as further outlined below.

The expression "granulate" refers to aggregates of particles, sometimes called granules. A granulate in general is prepared by compaction and/or compression techniques (dry granulation) or by wet granulation techniques, using a liquid in which optionally a wet granulation binding agent is dissolved (Remington's Pharmaceutical Sciences 18th ed. 1990, page 1641). Wet granulation techniques also include extrusion techniques. Accordingly the term granulate also comprises pellets, spherules, and extrudates, of which pellets preferably are used as examples of a granulate.

A pellet may be described as a small particle of approximately 1.0-1.6 mm in diameter and having a certain density, which particle is prepared by application of the pharmaceutical processes of extrusion and spheronisation to powder mixtures.

The active ingredient(s), optionally in admixture with one or more excipients, may be advantageously provided with a coating in order to mask the taste of such ingredient and/or to protect the same against possible harmful effects by light and/or moisture and/or to protect the mucosa in the mouth against the harmful effects exerted by the active compound.

Preferably the dosage forms to be used in accordance with the dosage regimens according to the invention are prepared by dry compaction techniques. Suitable techniques are for example described in Remington's Pharmaceutical Science 18th. ed. 1990, page 1644. They comprise dry granulation, roller compaction and direct compression. When tablets are prepared by these techniques, it is even more advantageous to use direct compression.

The dosage forms to be used in accordance with the treatment regimen according to the present invention are preferably provided with a coating. The coating has different purposes: it may serve for masking the taste of the active ingredient(s) used in the composition, whilst at the same time it is protecting the active ingredient against possible harmful effects by light and/or moisture such as oxidation, degradation, etc. Furthermore, the coating layer may prevent the subject from damage of the oral mucosa by the active ingredient.

The coating layer can be applied to the dosage forms by techniques well-known in the art such as spray-coating and microencapsulation. For tablets it can be in the form of a film-coating, a saccharide-coating or a compression coating. Preferably a film-coating process is used (Remington's Pharmaceutical Sciences 18th ed. 1990, page 1666). In case an active ingredient requires the application of a coating for fast-disintegrating tablets the individual granules can suitably be provided with a coating prior to compression into tablets.

Preferably it also contains a filler or diluents agent. Examples of such suitable compounds are:
  sugars, which may be selected from the group consisting of sucrose, fructose, sorbitol, xylitol, maltitol, aspartame, erythritol, isomalt, trehalose, maltose, mannose, sorbose, xylose, dextran, dextrin, pullulan, mannitol and lactose;
  microcrystalline cellulose or microfine cellulose;
  starch, a soluble starch or a starch derivative, such as a hydroxyethyl starch;
  calcium carbonate, sodium chloride, calcium phosphate, calcium hydrogen phosphate, calcium sulfate, sodium phosphate, carmellose potassium, carmellose calcium, carmellose sodium, synthetic aluminum silicate, etc.

Most preferred are microcrystalline cellulose and a sugar, selected from the group consisting of D-mannitol, erythritol, isomalt and trehalose. However, there is a preference for the use of microcrystalline cellulose, in view of stability of the composition containing fidaxomicin and xanthan gum, under a variety of storage conditions. On top of that for certain groups of patients who should not take sugar-containing compositions, the use of microcrystalline cellulose is advantageous.

The amount of microcrystalline cellulose should be as low as possible, but does not seem to be critical. The same is true when a sugar is used.

The granulate may further contain one or more of a disintegrant, since it is important that the fidaxomicin is quickly and uniformly dispersed, both in in vitro and in vivo situations. Suitable disintegrating agents are corn starch, potato starch, partly pregelatinized starch, but also the so-called super-disintegrants can be used; examples of which are crosscarmellose calcium, crosscarmellose sodium, crospovidone, sodium starch glycolate, low-substituted hydroxypropylcellulose and Amberlite IRP 88. A preferred disintegrant is sodium starch glycolate, which is commercially available under the trademark Primojel®. This disintegrant has shown that it is effective in compositions which contain either microcrystalline cellulose or a sugar as the diluents. Further it has shown that it contributes to an easy manufacturing of a granulate composition. Optionally a second disintegrant can be used, such as partly pregelatinised starch.

The composition to be used in accordance with the treatment regimen according to the invention can be an aqueous suspension, preferably in admixture with excipients, such as buffering agents, preservatives, flavouring agents, sweetening agents and viscosity increasing agents. Most preferably the compositions contain flavouring and sweetening agents to mask the taste of the tiacumicin compounds.

Examples of buffering agents are hydrochloric acid, diluted hydrochloric acid, sulfuric acid, adipic acid and its salt, citric acid and its salt, gluconic acid and its salt, succinic acid and its salt, ascorbic acid and its salt, glacial acetic acid and its salt, acetic acid and its salt, tartaric acid and its salt, fumaric acid and its salt, maleic acid and its salt, lactic acid and its salt, malic acid and its salt, phosphoric acid, and its salt, glycine, sodium hydrogencarbonate, sodium carbonate, sodium hydroxide, magnesium hydroxide etc. and combinations of the afore-mentioned agents.

Examples of preservatives are benzoic acid and its salt, an edetate acid and its salt, salicylic acid and its salt, dibutyl-hydroxytoluene, sorbic acid and its salt, a sodium dehydroacetate, para-hydroxybenzoic acid, and its salt, methylparaben, propylparaben, etc. and combinations of the afore-mentioned preservatives.

Examples of flavouring agents are orange essence, an orange oil, caramel, camphor, cinnamon oil, a spearmint oil, strawberry essence, chocolate essence, a cherry flavor, oil of bitter orange, pine|pineapple oil, mentha oil, a vanilla flavor, bitter essence, a fruits flavor, peppermint essence, a mix flavor, a mint flavor, menthol, lemon powder, a lemon oil, a rose oil etc. and combinations of the afore-mentioned flavouring agents.

Examples of sweetening agents are sucralose, aspartame, fructose, xylitol, glycyrrhizinic acid and its salt, saccharin and its salt, *stevia*, sucrose, sorbitol, glucose, hydrogenated maltose starch syrup, maltitol, maltose, etc. and combinations of the afore-mentioned sweetening agents.

Examples of viscosity enhancing agents are celluloses such as methylcellulose, ethylcellulose, hydroxypropylcellulose, hydroxyethylcellulose, hydroxypropylmethylcellulose, carboxymethylcellulose; gums such as xanthan gum, guar gum, gellan gum, dextran, carrageenan; polyvinylpyrrolidone; specially treated microcrystalline celluloses, such as water dispersible celluloses (microcrystalline cellulose and sodium carboxymethylcellulose); and combinations of the afore-mentioned viscosity enhancing agents.

Alternatively, the granulate to be used in accordance with the treatment regimen according to the invention in admixture with extragranular excipients can be used for the preparation of dispersible tablets.

Both dosing regimens i and ii according to the invention rapidly reduced *C. difficile* counts to below the level of detection. Spores continued to be detected sporadically, but no signs of recurrence of vegetative growth or toxin production were observed. Resolution of CDI was comparable with previously investigated dosing regimens. Effects of fidaxomicin on gut microflora populations such as total anaerobes, *Bacteroides*, total Clostridia, Lactobacilli, lactose fermenters and facultative anaerobes were modest, with only Bifidobacteria and Enterococci populations declining. Although Bifidobacteria declined to below the level of detection, they recovered to near pre-installation counts, which means to concentrations that were almost as high as before treatment with the tiacumicin compound. Effects of fidaxomicin on bifidobacteria levels in previous models have varied, likely due to variation in the composition of bifidobacteria species in the faecal samples of volunteers. Persistence of fidaxomicin at supra MIC level was noted (2-5 mg/L) but to a lesser extent than seen with some previous fidaxomicin dosing regimens (20 mg/L). Persistence of antimicrobial may prevent recrudescence of CDI spores for longer, whilst allowing recovery of gut microflora and hence the recovery of colonisation resistance.

Another embodiment is therefore directed to a method for recovering of gut Bifidobacteria population in log 10 cfu/ml in a patient, suffering from *Clostridium difficile* infections (CDI) or *Clostridium difficile* associated diarrhea or disease (CDAD) and receiving oral treatment with a tiacumicin compound, a stereo-isomer thereof, a polymorph thereof or a pharmaceutically acceptable solvate thereof, to 50 to 90% of the gut Bifidobacteria population in log 10 cfu/ml prior to administering the tiacumicin compound during days 15-45 after start of the treatment by orally administering the tiacumicin compound to the patient according to a dosage regimen, which is selected from the group consisting of:
  i. Administering 200 mg of the tiacumicin compound BID for 5 days followed by 5 days of rest and then 200 mg once daily for a further 10 days and
  ii. Administering 200 mg of the tiacumicin compound BID for 5 days followed by a single 200 mg every other day for 20 days.

Yet another embodiment is directed to a method for recovering of gut Bifidobacteria population in log 10 cfu/ml in a patient, suffering from *Clostridium difficile* infections (CDI) or *Clostridium difficile* associated diarrhea or disease (CDAD) and receiving oral treatment with a tiacumicin compound, a stereo-isomer thereof, a polymorph thereof or a pharmaceutically acceptable solvate thereof, to 50 to 90% of the gut Bifidobacteria population in log 10 cfu/ml prior to administering the tiacumicin compound during days 15-45 after start of the treatment by orally administering the tiacumicin compound to the patient according to a dosage regimen, which is selected from the group consisting of:
  i. Administering 200 mg of the tiacumicin compound BID for 5 days followed by 5 days of rest and then 200 mg once daily for a further 10 days and
  ii. Administering 200 mg of the tiacumicin compound BID for 5 days followed by a single 200 mg every other day for 20 days,
wherein the tiacumicin compound is fidaxomicin.

A further embodiment is directed to a method for recovering of gut Bifidobacteria population in log 10 cfu/ml in a patient, suffering from *Clostridium difficile* infections (CDI) or *Clostridium difficile* associated diarrhea or disease (CDAD) and receiving oral treatment with a tiacumicin compound, a stereo-isomer thereof, a polymorph thereof or a pharmaceutically acceptable solvate thereof, to 50 to 90% of the gut Bifidobacteria population in log 10 cfu/ml prior to administering the tiacumicin compound during days 15-45 after start of the treatment by orally administering the tiacumicin compound to the patient according to a dosage regimen, which is selected from the group consisting of:
  i. Administering 200 mg of the tiacumicin compound BID for 5 days followed by 5 days of rest and then 200 mg once daily for a further 10 days and
  ii. Administering 200 mg of the tiacumicin compound BID for 5 days followed by a single 200 mg every other day for 20 days, wherein the tiacumicin compound is fidaxomicin and is administered to the patient in the form of a film-coated tablet.

A further embodiment relates to a method for maintaining in a patient, suffering from *Clostridium difficile* infections (CDI) or *Clostridium difficile* associated diarrhea or disease (CDAD), having taken 200 mg of a tiacumicin compound, a stereo-isomer thereof, a polymorph thereof or a pharmaceutically acceptable solvate thereof, BID for 5 days and as a consequence thereof having a concentration of the tiacumicin compound, 2-7% of the concentration of the tiacumicin compound, as measured on day 5, by orally administering the tiacumicin compound to the patient according to a follow-up dosage regimen, which is selected from the group consisting of:
  i. 5 days of rest and then 200 mg of the tiacumicin compound once daily for a further 10 days and
  ii. a single 200 mg of the tiacumicin compound every other day for 20 days, for at least 20 days after completing the follow-up dosage regimen.

The following example further illustrates the invention. It will be apparent to the skilled person that these examples are solely for illustrative purposes and must not be considered to limit the invention.

EXAMPLES

Reference Example

Comparison of Extended Duration Fidaxomicin Dosing Regimens for Treatment of *Clostridium difficile* Infection (CDI) in an In Vitro Gut Model The effectiveness of long (Model A: 200 mg BID during 20 days) vs short pulsed (Model B: 200 mg BID during 5 days, rest during 5 days and 5 days 200 mg BID) course fidaxomicin using a validated CDI model was investigated. Results are available for this model (C. H. Chilton et al. (2013) in J. Antimicrobial Chemotherapy Advance Access September 2013 and C. H. Chilton et al., abstract 23$^{rd}$ European Congress of Clinical microbiology & Infectious Disease, Apr. 27-30, 2013, Berlin). The description of the model is provided in example 1 (see there).

Two 3-stage chemostat gut models were inoculated with pooled faeces (n=5). 107 cfu CD ribotype 027 (NAP1/BI) spores were added, and then clindamycin (CL, 33.9 mg/L qid, 7 d) was instilled to induce CDI i.e. germination and toxin production. Models were then treated with fidaxomicin (200 mg/L bd) for 20 or 5 d to achieve in vivo gut levels. 5 days post treatment in the short course model, a further 5 days fidaxomicin pulse was given. CD total viable counts (TVC), spore counts (SP), toxin titres (CYT), and gut bacteria were measured throughout. Data were also compared with results for FDX given for 7 days (model 7).
Results:
CL induced CD germination and high level toxin production (≥3 RU). In the model A, CD TVC and CYT reduced to the limit of detection (LOD) by day 5 & 7 (FIG. 4), respectively, with no evidence of recurrence. In the model B CD TVCs were reduced markedly (~4 $\log_{10}$ cfu/mL), but were still detectable on day 5 of treatment. The second 5 days fidaxomicin pulse, decreased TVC and SP to LOD (FIG. 4).

Both dosing regimens had limited effect on gut microflora, except bifidobacteria, which decreased ~6-8 $\log_{10}$ cfu/mL to below LOD and did not recover (FIG. 5).

Conclusions

In an in vitro gut model, 5 days fidaxomicin was less effective than 20 days (or 7 days) fidaxomicin in reducing CD TVC, SP and CYT, but a further 5 days fidaxomicin pulse increased efficacy, and overall was comparable to other dosing regimens (model B and model 7).

Effects on gut flora were similarly modest in model A and model B and model 7). 5 days fidaxomicin alone may be sub-optimal for CDI treatment, however model A (a 5 days+5 days pulsed dosing regimen may be as effective as model B (20 days fidaxomicin, extending the total length of coverage to 15 days).

Example 1

Pilot Study of Extended Dosing Regimens for Treatment of *C. difficile* Infection in an In Vitro Gut Model Two tests in a validated three-stage compound continuous culture system (Freeman J, O'Neill F J, Wilcox M H. The effects of cefotaxime and desacetylcefotaxime upon *Clostridium difficile* proliferation and toxin production in a triple-stage chemostat model of the human gut. J Antimicrob Chemother 2003; 52: 96-102; Baines S D, Freeman J, Wilcox M H. Effects of piperacillin/tazobactam on *Clostridium difficile* growth and toxin production in a human gut model. J Antimicrob Chemother 2005; 55: 974-82) were run in parallel. Models were inoculated with pooled faecal slurry (10% in anaerobic distilled water) from healthy volunteers (n=5, age >60 yrs).

The continuous culture system consisted of three vessels, V1, V2, and V3, with respective operating volumes of 0.22, 0.32, and 0.32 L (FIG. 1). Temperature (37° C.) and pH were automatically controlled to reflect the proximal-distal colon. Culture pH in the three vessels was 5.5, 6.2, and 6.8, respectively. Each fermentor was magnetically stirred and maintained under an atmosphere of CO2. The growth medium was continuously sparged with $O_2$-free $N_2$ and fed by peristaltic pump to V1. V1 sequentially supplied V2 and V3 via a series of weirs. The culture medium consisted of the following constituents (g liter-1) in distilled water: starch (BDH Ltd.), 5.0; pectin (citrus), 2.0; guar gum, 1.0; mucin (porcine gastric type III), 4.0; xylan (oatspelt), 2.0; arabinogalactan (larch wood), 2.0; inulin, 1.0; casein (BDH Ltd.), 3.0; peptone water, 5.0; tryptone, 5.0; bile salts No. 3, 0.4; yeast extract, 4.5; FeSO4 z 7H2O, 0.005; NaCl, 4.5; KCl, 4.5; KH2PO4, 0.5; MgSO4 z 7H2O, 1.25; CaCl2 z 6H2O, 0.15; NaHCO3, 1.5; cysteine, 0.8; hemin, 0.05; Tween 80, 1.0 The system was initially operated at a retention time (R) of 27.1 h (experiment 1), followed by an increase to R=66.7 h (experiment 2). Retention time was calculated as the reciprocal of dilution rate. System retention constitutes the sum of individual R values in each fermentor. Minimum doubling times of bacteria were calculated as 0.693/D, where D is the dilution rate (h−1) for each culture vessel. Each fermentor was inoculated with 100 ml of a fresh 10% (w/v) fecal slurry from a healthy, nonmethane producing donor. The fermentation system was allowed to equilibrate for 2 weeks before the medium pump was started at a flow rate of 13.2 ml/hr (System retention time of 67 hr), and was run for at least 336 h at each retention time to establish steady-state conditions, before material was taken for analysis. Steady-state conditions were assessed by monitoring short-chain fatty acid (SCFA) formation. Two samples were taken 48 h apart at each steady state. Once gut microbiota populations stabilised, models were spiked with 107 PCR ribotype 027 *C. difficile* spores, and simulated CDI was induced by clindamycin instillation (33.9 mg/L, QDS). Once high level toxin production was observed, fidaxomicin treatment commenced. Model C was instilled with 200 mg/L fidaxomicin BID for 5 days, followed by five days rest then 200 mg/L fidaxomicin once daily for a further 10 days (dosing regimen i). Model D was instilled with 200 mg/L fidaxomicin BID for 5 days followed by a single 200 mg/L fidaxomicin dose every other day for 20 days (dosing regimen ii). The model was left without further intervention for 21 days post treatment.

Measurements:
  *C. difficile* Total viable count and spore count (CFU/ml)
  Toxin concentration (Vero cell cytotoxin neutralisation assay)
  Microflora composition by selective culture
  Resistance emergence
  Antimicrobial concentration (bioassay).

Figure 11A:
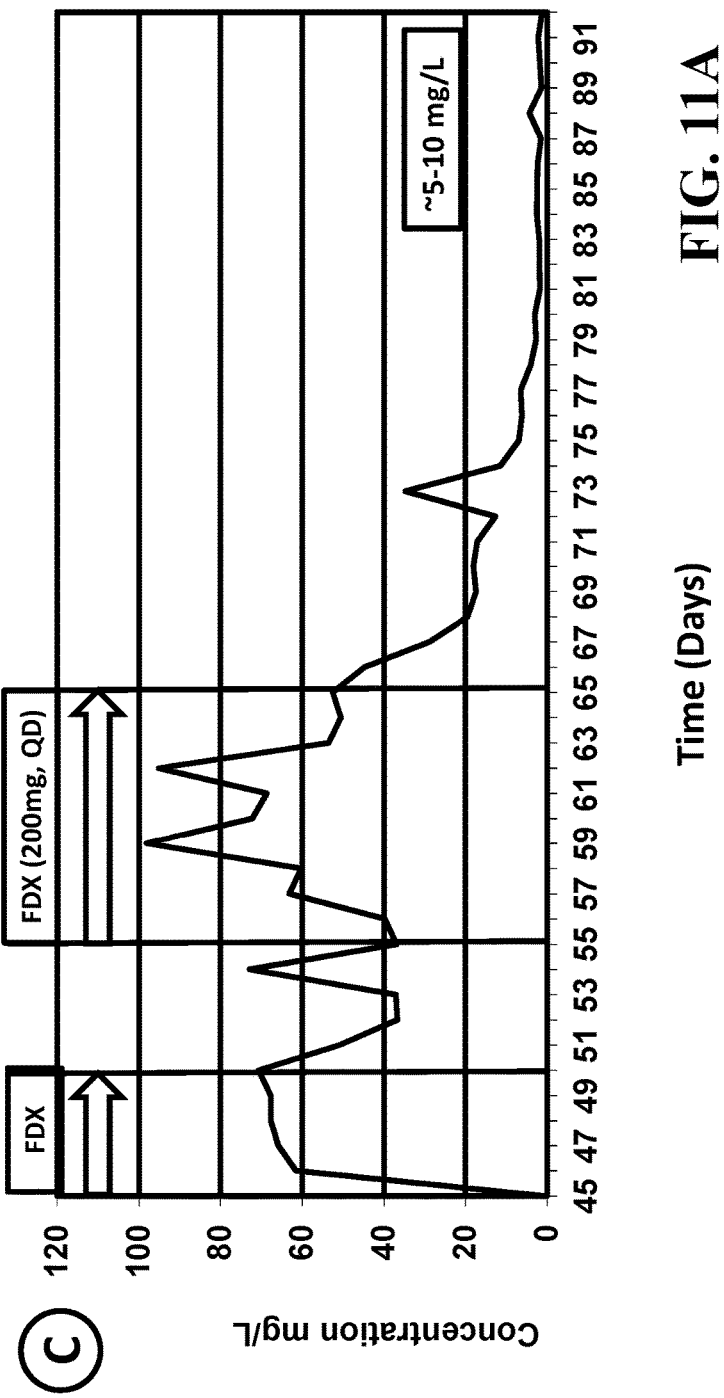
FIG. 11A provides a graphical representation of the antimicrobial concentrations achieved in IVGM versus days for the example C.
Figure 11B:
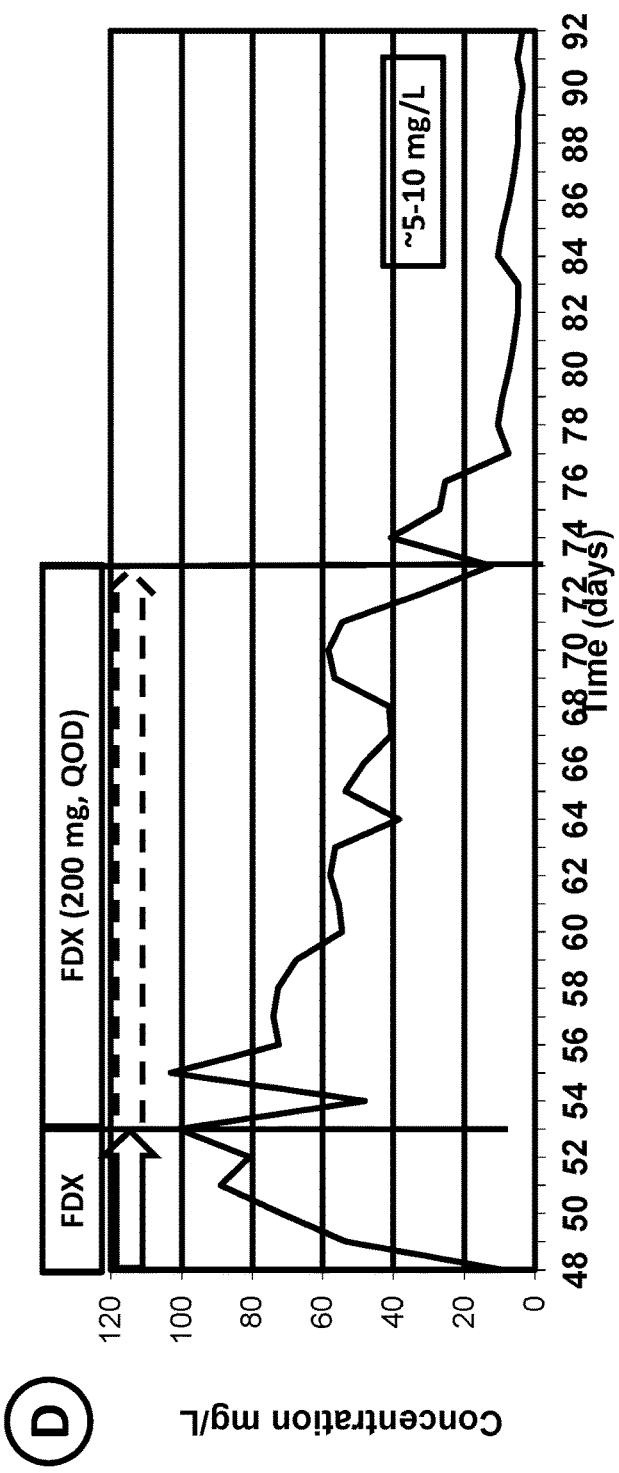
FIG. 11B provides a graphical representation of the antimicrobial concentrations achieved in IVGM versus days for the example D.
Figure 12A:
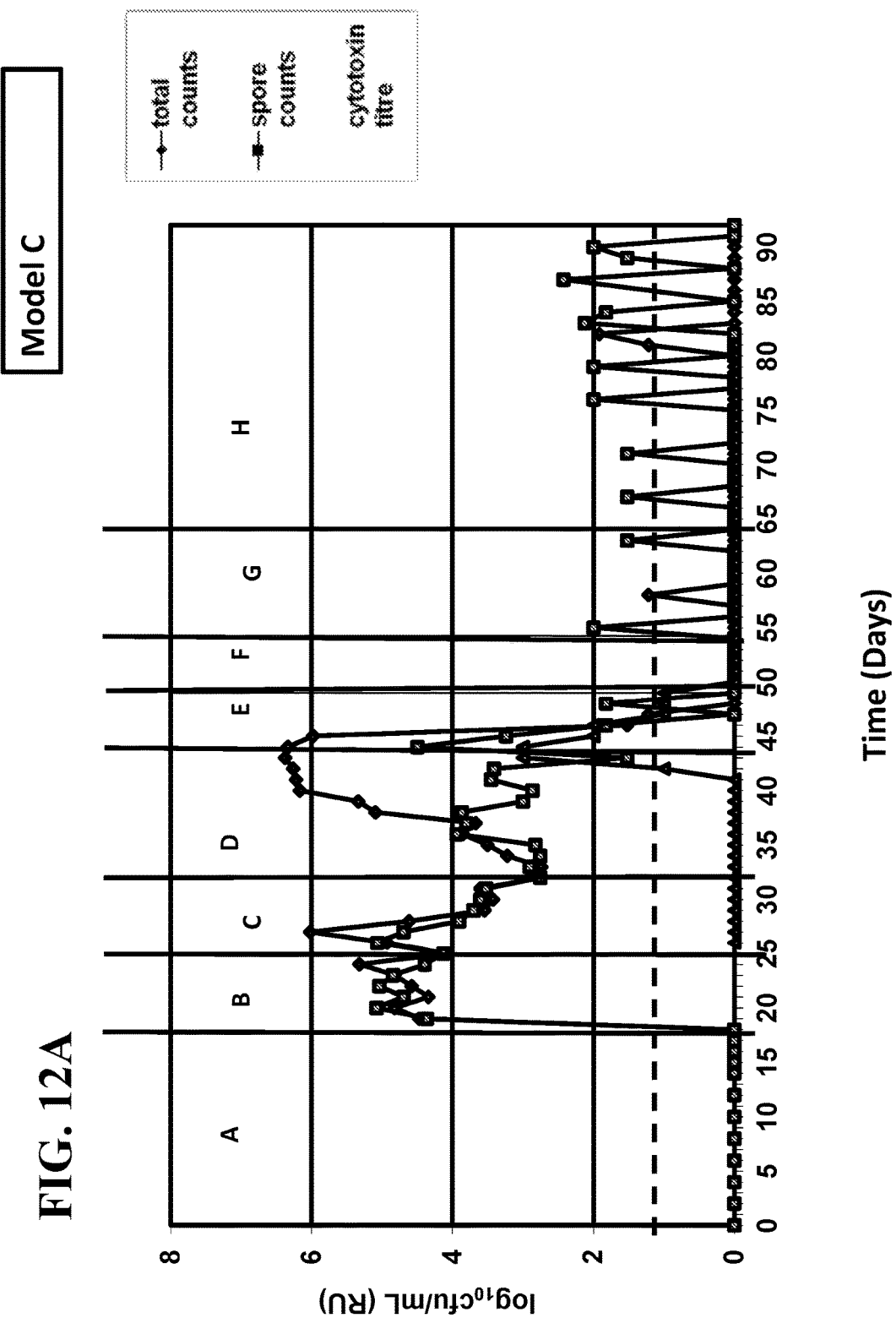
FIG. 12A shows mean *C. difficile* PCR ribotype 027 total viable counts (diamonds/*rhombi*) and spore counts ($\log_{10}$ cfu/mL) (squares) and cytotoxin titres (relative units, RU) (triangles) in vessel 3 of Model C (dosing regimen i). Horizontal dotted line indicates the limit of detection. Letters A-H refer to the different stages in the treatment as shown in FIG. 8B.
Figure 12B:
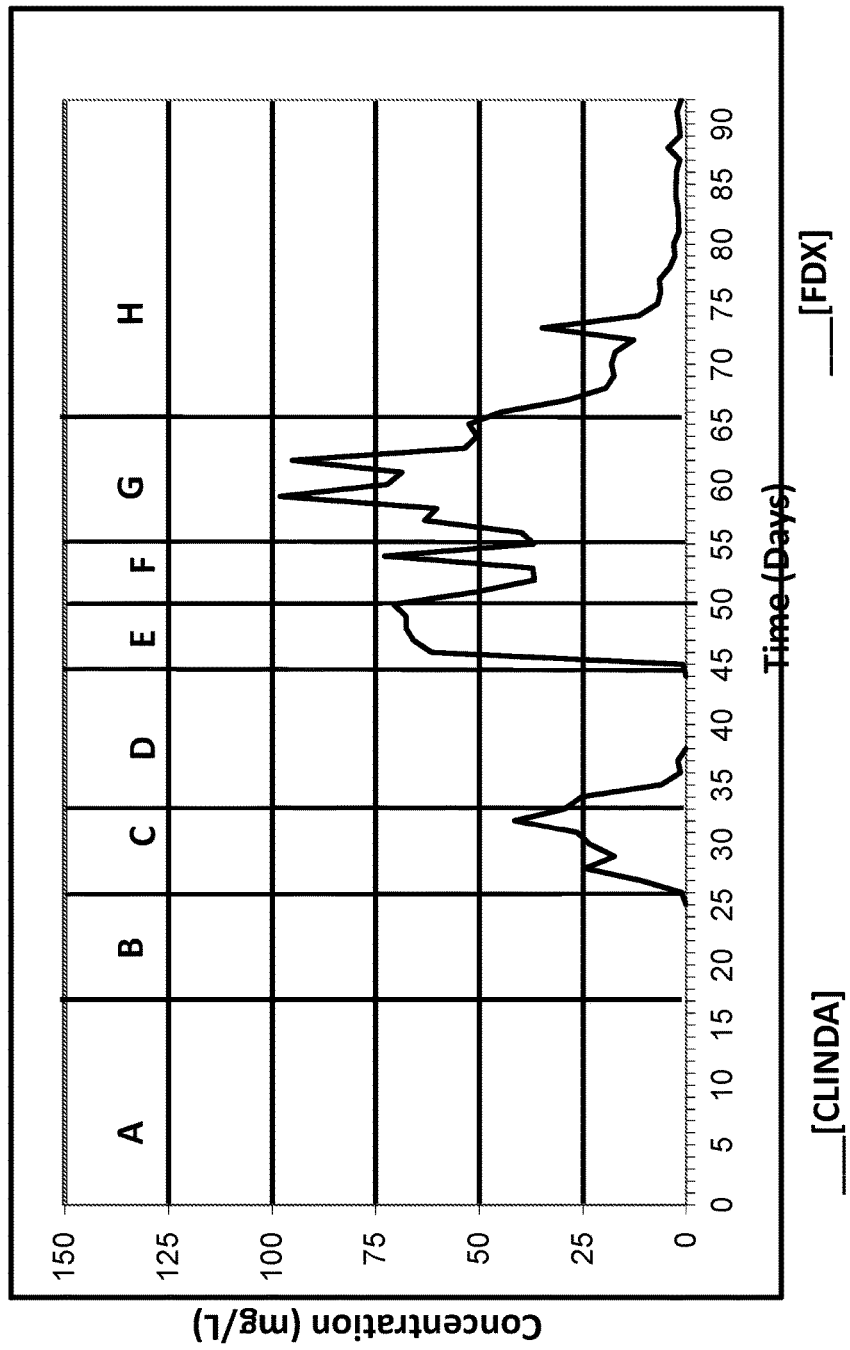
FIG. 12B shows the antimicrobial concentration (mg/L) in vessel 3 of Model C (dosing regimen i).
Figure 12C:
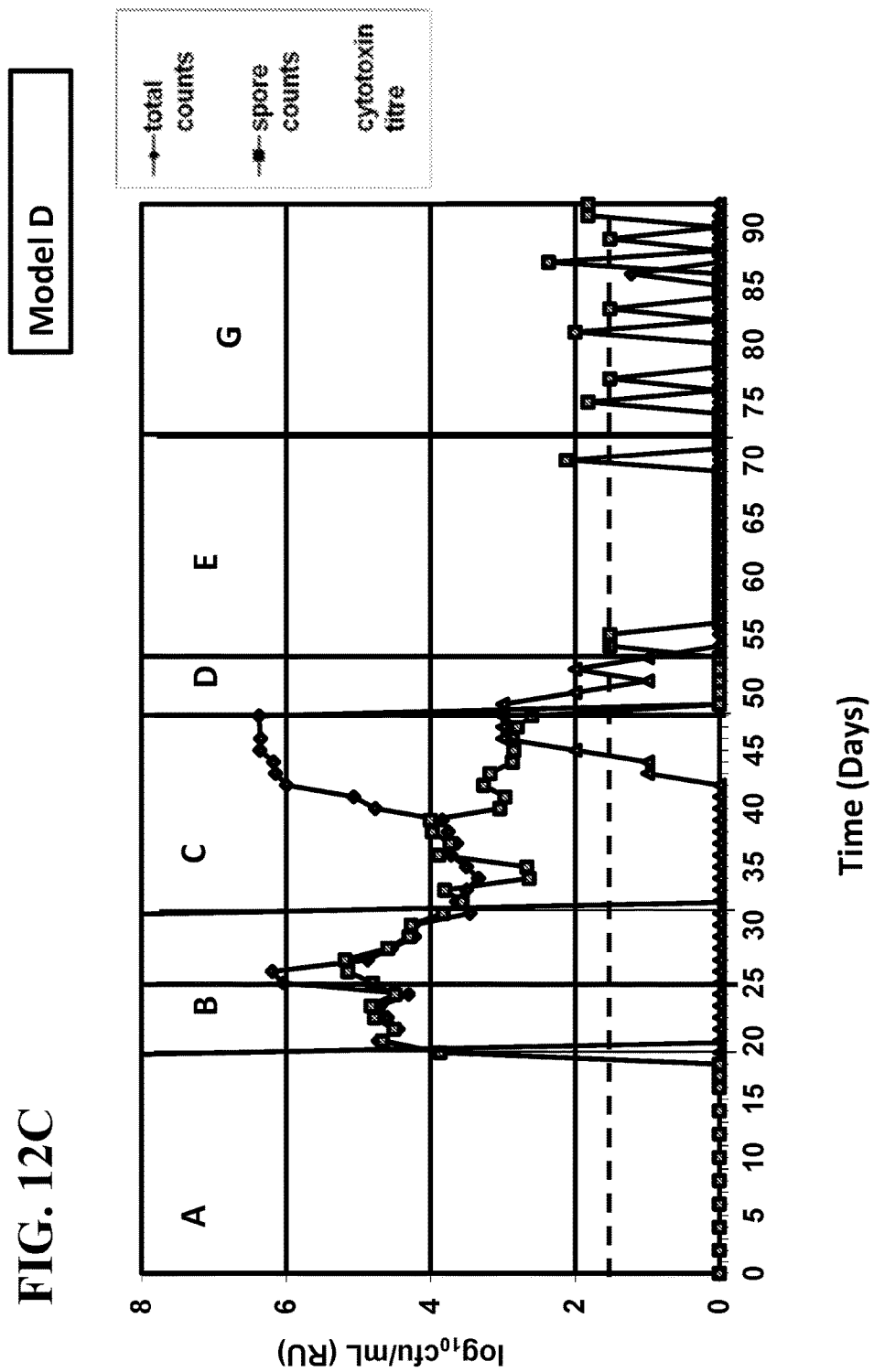
FIG. 12C shows mean *C. difficile* PCR ribotype 027 total viable counts (diamonds/*rhombi*) and spore counts ($\log_{10}$ cfu/mL) (squares) and cytotoxin titres (relative units, RU) (triangles) in vessel 3 of Model D (dosing regimen ii). Horizontal dotted line indicates the limit of detection. Letters A-G refer to the different stages in the treatment as shown in FIG. 8B.
Figure 12D:
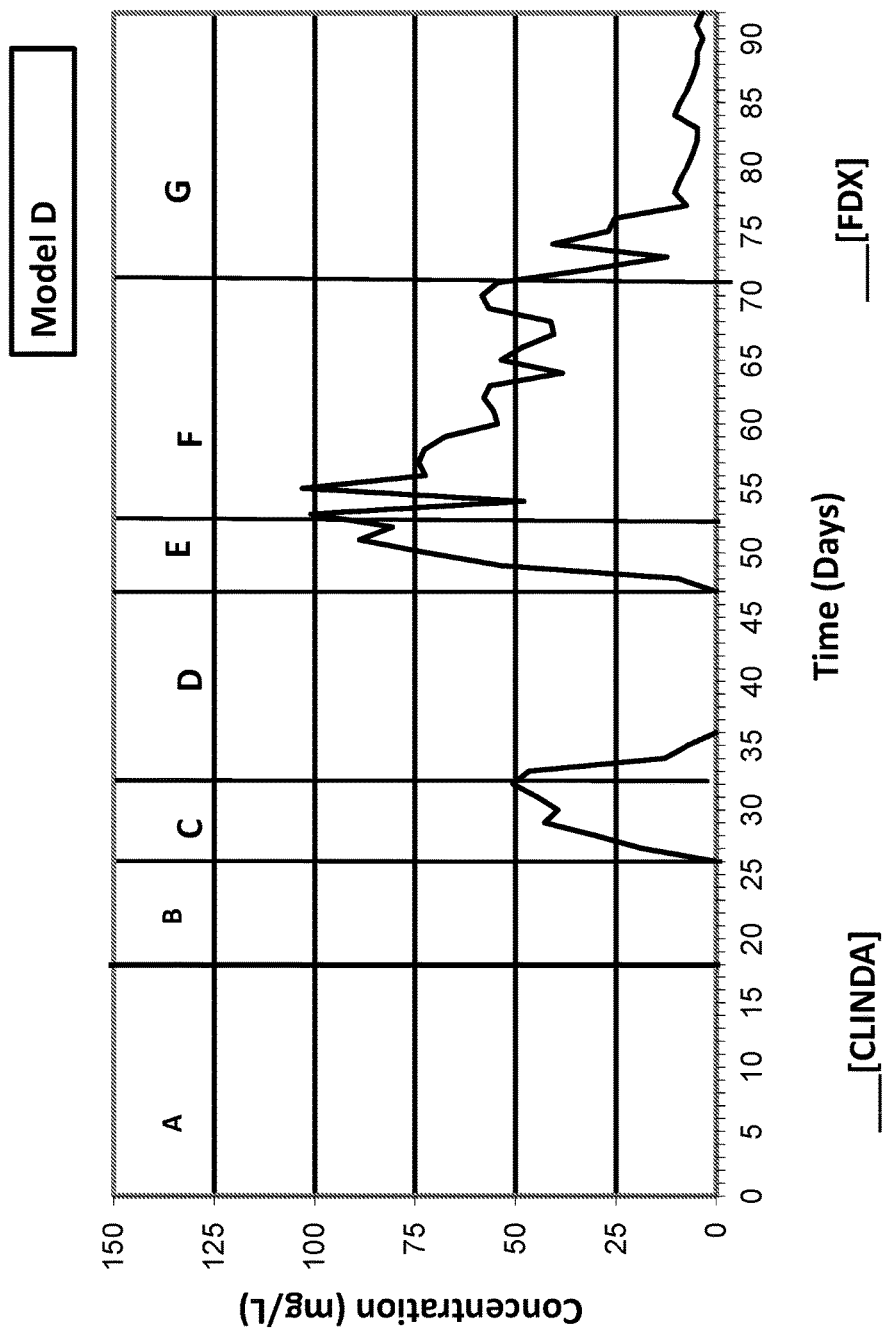
FIG. 12D shows the antimicrobial concentration (mg/L) in vessel 3 of Model D (dosing regimen ii).

Both tapered dosing regimens rapidly (<3 days) reduced *C. difficile* viable counts (~6 $\log_{10}$ cfu/mL), spore counts (~4 $\log_{10}$ cfu/mL) and toxin titres (3 RU) to below the level of detection. Vegetative cells and toxin remained below the level of detection for the remainder of the experiment. Spores were detected sporadically, at the limit of detection, in all three vessels of model C, but only intermittently from vessel 3 in model D. Fidaxomicin concentrations peaked at ~100 mg/L in both models. Persistence of fidaxomicin activity was slightly greater in model D (5 mg/L) (see FIG. 11B) than model C (2-5 mg/L) (see FIG. 11A), and remained at supra-MIC (0.25 mg/L) level for the duration of the experiment in both models. The effects of both dosing regimen on gut microflora were similarly limited, with declines in enterococci (2-5 $\log_{10}$ cfu/mL) and Bifidobacteria (6-8 $\log_{10}$ cfu/mL to limit of detection).

Bifidobacteria populations recovered to close to pre-fidaxomicin levels in both models by the end of the experiment.

5 days fidaxomicin sufficient to end toxin production
  but, less effective than Model A or model 7 at reducing *C. difficile* total counts and spores
  however, a further pulse of 5 days fidaxomicin reduced *C. difficile* counts further (comparable to model A or model 7)
  Effects of fidaxomicin pulse vs extended dosing on gut flora similarly modest
  Persistence of active fidaxomicin greater in extended and pulsed dosing regimens
  Pulsed dosing regimen may increase fidaxomicin persistence
  Further studies required to determine optimal dosing regimen to minimise recurrence.

Conclusions

Both evaluated tapered dosing regimens were effective for rapid resolution of simulated CDI in an in vitro gut model, and were comparable to previously evaluated standard and pulsed dosing regimen. Persistence of antimicrobial activity and some suppression of *C. difficile* spore recovery was observed. Tapered dosing regimens may help to suppress *C. difficile* spore germination for long periods of time, whilst allowing recovery of the indigenous gut microflora.

INDUSTRIAL APPLICABILITY

The treatment regimens with fidaxomicin compositions according to the present invention shows many advantages. The extension of the treatment duration period out from 10 to 20 or 25 days allows additional time for recovery of the patients colonic microflora which provides colonisation resistance against subsequent CDI relapse/recurrence without using additional medication. Therefore the clear benefit of the dosing regimens according to the present invention over the 20 day twice daily regimen is that it provides equivalent efficacy in terms of reduction of *C. difficile* cells, spores and toxin while allowing recovery of the bowel flora which is expected to translate into a further reduction in the recurrence rate over the existing dose (200 mg BID during 10 days), but it does this using the standard 10 day pack of fidaxomicin tablets (DIFICLIR™) rather than having to use 2 packs.

Therefore by changing the dosing frequency it is expected that the sustained clinical cure achieved using 1 pack of fidaxomicin tablets (DIFICLIR™) may be increased from around 14% to <5%. However also other fidaxomicin-containing compositions, such as a suspension, will have the same effect.

If the proposed clinical study based on the results of the in vitro test will be successful then it will be obvious that where possible, the recommended dosing regimen will be changed from the twice daily 200 mg for 10 days regimen to the dosing regimens according to the present invention. The expected benefit to patients, doctors and society would be that reducing the recurrence to below 5% would significantly alter the cost effectiveness argument in fidaxomicin's favour.

The invention claimed is:

1. A method of treating a *Clostridium difficile* infection (CDI) or *Clostridium difficile* associated diarrhea or disease (CDAD) in a patient according to a dosage regimen selected from the group consisting of:
   i. administering orally to the patient 200 mg of a tiacumicin compound, a stereoisomer thereof, a polymorph thereof or a pharmaceutically acceptable solvate thereof BID for 5 days followed by 5 days of rest and then 200 mg once daily for a further 10 days and
   ii. administering orally to the patient 200 mg of a tiacumicin compound, a stereoisomer thereof, a polymorph thereof or a pharmaceutically acceptable solvate thereof orally BID for 5 days followed by a single 200 mg every other day for 20 days.

2. The method according to claim 1, wherein the tiacumicin compound is selected from the group consisting of tiacumicin A, tiacumicin B, tiacumicin C, tiacumicin D, tiacumicin E, tiacumicin F and lipiarmycin.

3. The method according to claim 1, wherein the tiacumicin compound is lipiarmycin or tiacumicin B or a stereoisomer thereof.

4. The method according to claim 1, wherein the tiacumicin compound is tiacumicin B or a polymorph thereof.

5. The method according to claim 1, wherein the tiacumicin compound is fidaxomicin.

6. The method according to claim 1, wherein the tiacumicin compound, stereo-isomer thereof, polymorph thereof or pharmaceutically acceptable solvate thereof is present in a tablet, a suspension, a dry powder for aqueous suspension, a dry granulate for aqueous suspension, a film-coated tablet or a dispersible tablet.

7. The method according to claim 6, wherein the tablet is a film-coated tablet.

8. A method of treating *Clostridium difficile* infection (CDI) or *Clostridium difficile* associated diarrhea or disease (CDAD) in a patient according to a dosage regimen selected from the group consisting of:

i. administering orally to the patient 200 mg of a pharmaceutical composition comprising a tiacumicin compound, a stereoisomer thereof, a polymorph thereof or a pharmaceutically acceptable solvate thereof BID for 5 days followed by 5 days of rest and then 200 mg once daily for a further 10 days and ii. administering orally to the patient 200 mg of a tiacumicin compound, a stereoisomer thereof, a polymorph thereof or a pharmaceutically acceptable solvate thereof BID for 5 days followed by a single 200 mg every other day for 20 days.

9. The method according to claim 8, wherein the tiacumicin compound is selected from the group consisting of tiacumicin A, tiacumicin B, tiacumicin C, tiacumicin D, tiacumicin E, tiacumicin F and lipiarmycin.

10. The method according to claim 8, wherein the tiacumicin compound is lipiarmycin or tiacumicin B or a stereoisomer thereof.

11. The method according to claim 8, wherein the tiacumicin compound is tiacumicin B or a polymorph thereof.

12. The method according to claim 8, wherein the tiacumicin compound is fidaxomicin.

13. The method according to claim 8, wherein the pharmaceutical composition is a tablet, a suspension, a dry powder for an aqueous suspension, a dry granulate for aqueous suspension, a film-coated tablet or a dispersible tablet.

14. The method according to claim 13, wherein the tablet is a film-coated tablet.

15. A method of recovering gut Bifidobacteria population in $\log^{10}$ cfu/mL in a patient suffering from a *Clostridium difficile* infection (CDI) or *Clostridium difficile* associated diarrhea or disease (CDAD) and receiving oral treatment with a tiacumicin compound, a stereo-isomer thereof, a polymorph thereof or a pharmaceutically acceptable solvate thereof, to 50 to 90% of the gut Bifidobacteria population in $\log^{10}$ cfu/ml prior to administering the tiacumicin compound during days 15-45 after start of the treatment, by orally administering the tiacumicin compound to the patient according to a dosage regimen, which is selected from the group consisting of:

i. administering 200 mg of the tiacumicin compound BID for 5 days followed by 5 days of rest and then 200 mg once daily for a further 10 days and ii. administering 200 mg of the tiacumicin compound BID for 5 days followed by a single 200 mg every other day for 20 days.

16. The method according to claim 15, wherein the tiacumicin compound is selected from the group consisting of tiacumicin A, tiacumicin B, tiacumicin C, tiacumicin D, tiacumicin E, tiacumicin F and lipiarmycin.

17. The method according to claim 15, wherein the tiacumicin compound is lipiarmycin or tiacumicin B or a stereo-isomer thereof.

18. The method according to claim 15, wherein the tiacumicin compound is tiacumicin B or a polymorph thereof.

19. The method according to claim 15, wherein the tiacumicin compound is fidaxomicin.

20. The method according to claim 15, wherein the tiacumicin compound, a stereo-isomer thereof, a polymorph thereof or a pharmaceutically acceptable solvate thereof is present in a tablet, a suspension, a dry powder for an aqueous suspension, a dry granulate for an aqueous suspension, a film-coated tablet or a dispersible tablet.

21. The method according to claim 20, wherein the tablet is a film-coated tablet.

* * * * *